(12) United States Patent
Parker, Jr. et al.

(10) Patent No.: US 7,087,599 B2
(45) Date of Patent: Aug. 8, 2006

(54) ESTROGEN RECEPTOR MODULATORS

(75) Inventors: Dann LeRoy Parker, Jr., Cranford, NJ (US); Ronald W. Ratcliffe, Matawan, NJ (US); Robert R. Wilkening, Maplewood, NJ (US); Kenneth J. Wildonger, Bridgewater, NJ (US)

(73) Assignee: Merck & Co., Inc., Rahway, NJ (US)

( * ) Notice: Subject to any disclaimer, the term of this patent is extended or adjusted under 35 U.S.C. 154(b) by 862 days.

(21) Appl. No.: 09/782,855

(22) Filed: Feb. 14, 2001

(65) Prior Publication Data

US 2003/0027840 A1 Feb. 6, 2003

Related U.S. Application Data

(60) Provisional application No. 60/182,372, filed on Feb. 14, 2000.

(51) Int. Cl.
| A61K 31/535 | (2006.01) |
| A61K 31/12 | (2006.01) |
| C07D 295/00 | (2006.01) |
| C07C 251/18 | (2006.01) |
| C07C 49/225 | (2006.01) |

(52) U.S. Cl. .................... 514/231.2; 514/247; 514/256; 514/319; 514/365; 514/372; 514/374; 514/378; 514/385; 514/396; 514/438; 514/461; 514/640; 514/680; 544/154; 544/268; 544/294; 544/381; 546/196; 546/204; 546/285; 546/302; 548/196; 548/206; 548/215; 548/300.1; 548/347.1; 548/529; 549/78; 549/80; 549/497; 564/226; 564/267; 568/326; 568/733

(58) Field of Classification Search ................ 544/154, 544/268, 294, 381; 546/196, 204, 285, 302; 548/146, 206, 215, 300.1, 347.1, 539; 549/78, 549/80, 497; 564/226, 267; 568/326, 733; 514/231.2, 247, 256, 319, 365, 372, 324, 514/378, 385, 396, 438, 690, 680, 732, 761, 514/236

See application file for complete search history.

(56) References Cited

U.S. PATENT DOCUMENTS

| 4,316,043 A | 2/1982 | Cragoe, Jr. et al. |
| 4,317,922 A | 3/1982 | Cragoe, Jr. et al. |
| 4,356,313 A | 10/1982 | Cragoe, Jr. et al. |
| 4,356,314 A | 10/1982 | Cragoe, Jr. et al. |
| 4,377,354 A | 3/1983 | Morton |
| 4,604,396 A * | 8/1986 | Cragoe et al. ............... 514/256 |
| 4,675,341 A | 6/1987 | Cragoe, Jr. |
| 4,704,472 A | 11/1987 | Conn et al. |
| 4,731,470 A | 3/1988 | Pietruszkiewicz et al. |
| 4,731,471 A | 3/1988 | Cragoe, Jr. et al. |
| 4,731,472 A | 3/1988 | Pietruszkiewicz et al. |
| 4,797,391 A | 1/1989 | Woltersdorf, Jr. et al. |
| 4,835,313 A | 5/1989 | Pietruszkiewicz et al. |
| 6,251,898 B1 * | 6/2001 | Cragoe et al. ........... 514/228.8 |

* cited by examiner

*Primary Examiner*—Cecilia J. Tsang
*Assistant Examiner*—Raymond Covington
(74) *Attorney, Agent, or Firm*—Nicole M. Beeler; Mark R. Daniel

(57) ABSTRACT

The present invention relates to compounds and derivatives thereof, their synthesis, and their use as estrogen receptor modulators. The compounds of the instant invention are ligands for estrogen receptors and as such may be useful for treatment or prevention of a variety of conditions related to estrogen functioning including: bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restinosis, gynacomastia, vascular smooth muscle cell proliferation, obesity, incontinence, and cancer, in particular of the breast, uterus and prostate.

27 Claims, No Drawings

ESTROGEN RECEPTOR MODULATORS

This application claims the benefit of provisional application 60/182,372 filed on Feb. 14, 2000.

BACKGROUND OF THE INVENTION

Naturally occurring and synthetic estrogens have broad therapeutic utility, including: relief of menopausal symptoms, treatment of acne, treatment of dysmenorrhea and dysfunctional uterine bleeding, treatment of osteoporosis, treatment of hirsutism, treatment of prostatic cancer, treatment of hot flashes and prevention of cardiovascular disease. Because estrogen is very therapeutically valuable, there has been great interest in discovering compounds that mimic estrogen-like behavior in estrogen responsive tissues.

For example, estrogen-like compounds would be beneficial in the as treatment and prevention of bone loss. Bone loss occurs in a wide range of subjects, including women that are post-menopausal or have had a hysterectomy, patients who were or are currently being treated with corticosteroids, and patient's having gonadal dysgenesis. The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the U.S., there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Osteoporosis affects approximately 20 to 25 million post-menopausal women in the U.S. alone. It has been theorized that the rapid loss of bone mass in these women is due to the cessation of estrogen production of the ovaries. Since studies have shown that estrogen slows the reduction of bone mass due to osteoporosis, estrogen replacement therapy is a recognized treatment for post-menopausal osteoporosis.

In addition to bone mass, estrogen appears to have an effect on the biosynthesis of cholesterol and cardiovascular health. Statistically, the rate of occurrence of cardiovascular disease is roughly equal in postmenopausal women and men; however, premenopausal women have a much lower incidence of cardiovascular disease than men. Because post-menopausal women are estrogen deficient, it is believed that estrogen plays a beneficial role in preventing cardiovascular disease. The mechanism is not well understood, but evidence indicates that estrogen can upregulate the low density lipid (LDL) cholesterol receptors in the liver to remove excess cholesterol.

Postmenopausal women given estrogen replacement therapy experience a return of lipid levels to concentrations comparable to levels associated with the premenopausal state. Thus, estrogen replacement therapy could be an effective treatment for such disease. However, the side effects associated with long term estrogen use limit the use of this alternative.

In models, estrogen has been shown to have beneficial effects on cognitive functioning, such as relieveing anxiety and depression and treating and/or preventing Alzheimer's disease. Estrogen affects the central nervous system by increasing cholinergic functioning, neurotrophin and neurotrophin receptor expression. Estrogen also increases glutamergic synaptic transmission, alters amyloid precursor protein processing and provides neuroprotection. Thus, the estrogen receptor modulators of the present invention could be beneficial for improving cognitive functioning.

Other disease states that affect postmenopausal women include estrogen-dependent breast cancer and uterine cancer. Anti-estrogen compounds, such as tamoxifen, have commonly been used as chemotherapy to treat breast cancer patients. Tamoxifen, a dual antagonist and agonist of estrogen receptors, is beneficial in treating estrogen-dependent breast cancer. However, treatment with tamoxifen is less than ideal because tamoxifen's agonist behavior enhances its unwanted estrogenic side effects. For example, tamoxifen and other compounds that agonize estrogen receptors tend to increase cancer cell production in the uterus. A better therapy for such cancers would be an anti-estrogen compound that has negligible or nonexistent agonist properties.

Although estrogen can be beneficial for treating pathologies such as bone loss, increased lipid levels, and cancer, long-term estrogen therapy has been implicated in a variety of disorders, including an increase in the risk of uterine and endometrial cancers. These and other side effects of estrogen replacement therapy are not acceptable to many women, thus limiting its use.

Alternative regimens, such as a combined progestogen and estrogen dose, have been suggested in an attempt to lessen the risk of cancer. However, such regimens cause the patient to experience withdrawal bleeding, which is unacceptable to many older women. Furthermore, combining estrogen with progestogen reduces the beneficial cholesterol-lowering effect of estrogen therapy. In addition, the long term effects of progestogen treatment are unknown.

In addition to post-menopausal women, men suffering from prostatic cancer can also benefit from anti-estrogen compounds. Prostatic cancer is often endocrine-sensitive; androgen stimulation fosters tumor growth, while androgen suppression retards tumor growth. The administration of estrogen is helpful in the treatment and control of prostatic cancer because estrogen administration lowers the level of gonadotropin and, consequently, androgen levels.

The estrogen receptor has been found to have two forms: ERα and ERβ. Ligands bind differently to these two forms, and each form has a different tissue specificity to binding ligands. Thus, it is possible to have compounds that are selective for ERα or ERβ, and therefore confer a degree of tissue specificity to a particular ligand.

What is needed in the art are compounds that can produce the same positive responses as estrogen replacement therapy without the negative side effects. Also needed are estrogen-like compounds that exert selective effects on different tissues of the body.

The compounds of the instant invention are ligands for estrogen receptors and as such may be useful for treatment or prevention of a variety of conditions related to estrogen functioning including: bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restinosis, gynacomastia, vascular smooth muscle cell proliferation, obesity, incontinence, and cancer, in particular of the breast, uterus and prostate.

SUMMARY OF THE INVENTION

The present invention relates to compounds of the following chemical formula:

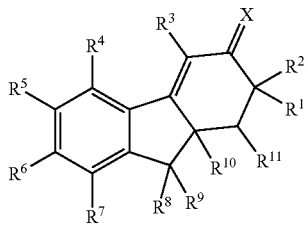

wherein X is selected from the group consisting of: O, N—$OR^a$, N—$NR^aR^b$ and $C_{1-6}$ alkylidene, wherein said alkylidene group is unsubstituted or substituted with a group selected from hydroxy, amino, $O(C_{1-4}alkyl)$, $NH(C_{1-4}alkyl)$, or $N(C_{1-4}alkyl)_2$;

$R^1$ is selected from the group consisting of hydrogen, $C_{1-6}$alkyl, $C_{2-6}$alkenyl, and $C_{2-6}$alkynyl, wherein said alkyl, alkenyl and alkynyl groups are either unsubstituted or substituted with a group selected from $OR^c$, $SR^c$, $NR^bR^c$, $C(=O)R^c$, $C(=O)CH_2OH$, or phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

$R^2$ is selected from the group consisting of hydrogen, hydroxy, iodo, $O(C=O)R^c$, $C(=O)R^c$, $CO_2R^c$, $C_{1-6}$alkyl, $C_{2-6}$alkenyl, and $C_{2-6}$alkynyl, wherein said alkyl, alkenyl and alkynyl groups are either unsubstituted or substituted with a group selected from $OR^c$, $SR^c$, $NR^bR^c$, $C(=O)R^c$, $C(=O)CH_2OH$, or phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

or $R^1$ and $R^2$, when taken together with the carbon atom to which they are attached, form a carbonyl group;

or $R^1$ and $R^2$, when taken together, form a $C_{1-6}$ alkylidene group, wherein said alkylidene group is either unsubstituted or substituted with a group selected from the group consisting of hydroxy, $O(C_{1-4}alkyl)$, $N(C_{1-4}alkyl)_2$, and phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

$R^3$ is selected from the group consisting of hydrogen, fluoro, chloro, bromo, iodo, cyano, $NR^aR^c$, $OR^a$, $C(=O)R^a$, $CO_2R^c$, $CONR^aR^c$, $SR^a$, $S(=O)R^a$, $SO_2R^a$, $C_{1-10}$alkyl, $C_{2-10}$alkenyl, $C_{2-10}$alkynyl, $C_{3-7}$cycloalkyl, 4–7 membered heterocycloalkyl, cycloalkylalkyl, aryl, heteroaryl, arylalkyl, and heteroarylalkyl, wherein said alkyl, alkenyl, alkynyl, cycloalkyl, aryl and heteroaryl groups are either unsubstituted or independently substituted with 1, 2 or 3 groups selected from fluoro, chloro, bromo, iodo, cyano, $OR^a$, $NR^aR^c$, $O(C=O)R^a$, $O(C=O)NR^aR^c$, $NR^a(C=O)R^c$, $NR^a(C=O)OR^c$, $C(=O)R^a$, $CO_2R^a$, $CONR^aR^c$, $CSNR^aR^c$, $SR^a$, $S(O)R^a$, $SO_2R^a$, $SO_2NR^aR^c$, $YR^d$, and $ZYR^d$;

$R^4$ is selected from the group consisting of hydrogen, hydroxy, amino, methyl, $CF_3$, fluoro, chloro, and bromo;

$R^5$ and $R^6$ are each independently selected from the group consisting of hydrogen, fluoro, chloro, bromo, methyl, amino, $OR^b$, $OR^a$, $O(C=O)R^c$, $O(C=O)OR^c$, and $NH(C=O)R^c$;

$R^7$ is selected from the group consisting of hydrogen, $OR^b$, $NR^bR^c$, fluoro, chloro, bromo, iodo, cyano, nitro, $C_{1-6}$alkyl, $C_{2-6}$alkenyl, $CF_3$, and $CHF_2$;

$R^8$ and $R^9$ are each independently selected from the group consisting of hydrogen, $C_{1-6}$alkyl, $C_{2-6}$alkenyl, and $C_{2-6}$alkynyl, or $R^8$ and $R^9$, when taken together with the carbon atom to which they are attached, form a 3–5 membered cycloalkyl ring, or $R^8$ and $R^9$, when taken together with the carbon atom to which they are attached, form a carbonyl group;

$R^{10}$ is selected from the group consisting of hydrogen, $C_{1-10}$alkyl, $C_{2-10}$alkenyl, $C_{2-10}$alkynyl, $C_{3-6}$cycloalkyl, cycloalkylalkyl, aryl, heteroaryl, arylalkyl and heteroarylalkyl, wherein said alkyl, alkenyl, alkynyl, cycloalkyl, cycloalkylalkyl, aryl, heteroaryl, arylalkyl and heteroarylalkyl groups can be optionally substituted with a group selected from chloro, bromo, iodo, $OR^b$, $SR^b$, $C(=O)R^b$, or 1–5 fluoro, or $R^{10}$ and $R^1$, when taken together with the three intervening carbon atoms to which they are attached, form a 5–6 membered cycloalkyl or cycloalkenyl ring which can be optionally substituted with 1 or 2 groups selected from oxo, hydroxy, or $C_{1-6}$alkyl;

$R^{11}$ is selected from the group consisting of hydrogen and $C_{1-4}$alkyl;

$R^a$ is selected from the group consisting of hydrogen, $C_{1-10}$alkyl, and phenyl, wherein said alkyl group can be optionally substituted with a group selected from hydroxy, amino, $O(C_{1-4}alkyl)$, $NH(C_{1-4}alkyl)$, $N(C_{1-4}alkyl)_2$, phenyl, or 1–5 fluoro, and wherein said phenyl groups can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

$R^b$ is selected from the group consisting of hydrogen, $C_{1-10}$alkyl, benzyl and phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

$R^c$ is selected from the group consisting of hydrogen, $C_{1-10}$alkyl and phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

or $R^a$ and $R^c$, whether or not on the same atom, can be taken together with any attached and intervening atoms to form a 4–7 membered ring;

$R^d$ is selected from the group consisting of $NR^bR^c$, $OR^a$, $CO_2R^a$, $O(C=O)R^a$, CN, $NR^c(C=O)R^b$, $CONR^aR^c$, $SO_2NR^aR^c$, and a 4–7 membered N-heterocycloalkyl ring that can be optionally interrupted by O, S, $NR^c$, or C=O;

Y is selected from the group consisting of $CR^bR^c$, $C_{2-6}$ alkylene and $C_{2-6}$ alkenylene, wherein said alkylene and alkenylene linkers can be optionally interrupted by O, S, or $NR^c$;

Z is selected from the group consisting of O, S, $NR^c$, C=O, O(C=O), (C=O)O, $NR^c(C=O)$ or $(C=O)NR^c$;

and the pharmaceutically acceptable salts thereof.

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an estrogen receptor modulating effect in a mammal in need thereof by administering the compounds and pharmaceutical compositions of the present invention.

The present invention also relates to methods for eliciting an estrogen receptor antagonizing effect in a mammal in need thereof by administering the compounds and pharmaceutical compositions of the present invention.

The present invention also relates to methods for eliciting an estrogen receptor agonizing effect in a mammal in need thereof by administering the compounds and pharmaceutical compositions of the present invention.

The present invention also relates to methods for treating or preventing disorders related to estrogen functioning, bone loss, bone fractures, osteoporosis, cartilage degeneration, endometriosis, uterine fibroid disease, cancer of the breast, uterus or prostate, hot flashes, cardiovascular disease, impairment of cognitive function, cerebral degenerative disorders, restenosis, gynacomastia, vascular smooth muscle cell proliferation, obesity and incontinence in a mammal in need thereof by administering the compounds and pharmaceutical compositions of the present invention.

The present invention also relates to methods for reducing bone loss, lowering LDL cholesterol levels and eliciting a vasodilatory effect, in a mammal in need thereof by administering the compounds and pharmaceutical compositions of the present invention.

DETAILED DESCRIPTION OF THE INVENTION

The present invention relates to compounds useful as estrogen receptor modulators. Compounds of the present invention are described by the following chemical formula:

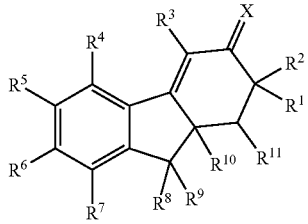

wherein X is selected from the group consisting of: O, N—$OR^a$, N—$NR^aR^b$ and $C_{1-6}$ alkylidene, wherein said alkylidene group is unsubstituted or substituted with a group selected from hydroxy, amino, $O(C_{1-4}alkyl)$, $NH(C_{1-4}alkyl)$, or $N(C_{1-4}alkyl)_2$;

$R^1$ is selected from the group consisting of hydrogen, $C_{1-6}$alkyl, $C_{2-6}$alkenyl, and $C_{2-6}$alkynyl, wherein said alkyl, alkenyl and alkynyl groups are either unsubstituted or substituted with a group selected from $OR^c$, $SR^c$, $NR^bR^c$, $C(=O)R^c$, $C(=O)CH_2OH$, or phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

$R^2$ is selected from the group consisting of hydrogen, hydroxy, iodo, $O(C=O)R^c$, $C(=O)R^c$, $CO_2R^c$, $C_{1-6}$alkyl, $C_{2-6}$alkenyl, and $C_{2-6}$alkynyl, wherein said alkyl, alkenyl and alkynyl groups are either unsubstituted or substituted with a group selected from $OR^c$, $SR^c$, $NR^bR^c$, $C(=O)R^c$, $C(=O)CH_2OH$, or phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

or $R^1$ and $R^2$, when taken together with the carbon atom to which they are attached, form a carbonyl group;

or $R^1$ and $R^2$, when taken together, form a $C_{1-6}$ alkylidene group, wherein said alkylidene group is either unsubstituted or substituted with a group selected from the group consisting of hydroxy, $O(C_{1-4}alkyl)$, $N(C_{1-4}alkyl)_2$, and phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

$R^3$ is selected from the group consisting of hydrogen, fluoro, chloro, bromo, iodo, cyano, $NR^aR^c$, $OR^a$, $C(=O)R^a$, $CO_2R^c$, $CONR^aR^c$, $SR^a$, $S(=O)R^a$, $SO_2R^a$, $C_{1-10}$alkyl, $C_{2-10}$alkenyl, $C_{2-10}$alkynyl, $C_{3-7}$cycloalkyl, 4–7 membered heterocycloalkyl, cycloalkylalkyl, aryl, heteroaryl, arylalkyl, and heteroarylalkyl, wherein said alkyl, alkenyl, alkynyl, cycloalkyl, aryl and heteroaryl groups are either unsubstituted or independently substituted with 1, 2 or 3 groups selected from fluoro, chloro, bromo, iodo, cyano, $OR^a$, $NR^aR^c$, $O(C=O)R^a$, $O(C=O)NR^aR^c$, $NR^a(C=O)R^c$, $NR^a(C=O)OR^c$, $C(=O)R^a$, $CO_2R^a$, $CONR^aR^c$, $CSNR^aR^c$, $SR^a$, $S(O)R^a$, $SO_2R^a$, $SO_2NR^aR^c$, $YR^d$, and $ZYR^d$;

$R^4$ is selected from the group consisting of hydrogen, hydroxy, amino, methyl, $CF_3$, fluoro, chloro, and bromo;

$R^5$ and $R^6$ are each independently selected from the group consisting of hydrogen, fluoro, chloro, bromo, methyl, amino, $OR^b$, $OR^a$, $O(C=O)R^c$, $O(C=O)OR^c$, and $NH(C=O)R^c$;

$R^7$ is selected from the group consisting of hydrogen, $OR^b$, $NR^bR^c$, fluoro, chloro, bromo, iodo, cyano, nitro, $C_{1-6}$alkyl, $C_{2-6}$alkenyl, $CF_3$, and $CHF_2$;

$R^8$ and $R^9$ are each independently selected from the group consisting of hydrogen, $C_{1-6}$alkyl, $C_{2-6}$alkenyl, and $C_{2-6}$alkynyl, or $R^8$ and $R^9$, when taken together with the carbon atom to which they are attached, form a 3–5 membered cycloalkyl ring, or $R^8$ and $R^9$, when taken together with the carbon atom to which they are attached, form a carbonyl group;

$R^{10}$ is selected from the group consisting of hydrogen, $C_{1-10}$alkyl, $C_{2-10}$alkenyl, $C_{2-10}$alkynyl, $C_{3-6}$cycloalkyl, cycloalkylalkyl, aryl, heteroaryl, arylalkyl and heteroarylalkyl, wherein said alkyl, alkenyl, alkynyl, cycloalkyl, cycloalkylalkyl, aryl, heteroaryl, arylalkyl and heteroarylalkyl groups can be optionally substituted with a group selected from chloro, bromo, iodo, $OR^b$, $SR^b$, $C(=O)R^b$, or 1–5 fluoro, or $R^{10}$ and $R^1$, when taken together with the three intervening carbon atoms to which they are attached, form a 5–6 membered cycloalkyl or cycloalkenyl ring which can be optionally substituted with 1 or 2 groups selected from oxo, hydroxy, or $C_{1-6}$alkyl;

$R^{11}$ is selected from the group consisting of hydrogen and $C_{1-4}$alkyl;

$R^a$ is selected from the group consisting of hydrogen, $C_{1-10}$alkyl, and phenyl, wherein said alkyl group can be optionally substituted with a group selected from hydroxy, amino, $O(C_{1-4}alkyl)$, $NH(C_{1-4}alkyl)$, $N(C_{1-4}alkyl)_2$, phenyl, or 1–5 fluoro, and wherein said phenyl groups can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

$R^b$ is selected from the group consisting of hydrogen, $C_{1-10}$alkyl, benzyl and phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

$R^c$ is selected from the group consisting of hydrogen, $C_{1-10}$alkyl and phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, C(O)H, and $C(O)(C_{1-4}alkyl)$;

or $R^a$ and $R^c$, whether or not on the same atom, can be taken together with any attached and intervening atoms to form a 4–7 membered ring;

$R^d$ is selected from the group consisting of $NR^bR^c$, $OR^a$, $CO_2R^a$, $O(C=O)R^a$, CN, $NR^c(C=O)R^b$, $CONR^aR^c$, $SO_2NR^aR^c$, and a 4–7 membered N-heterocycloalkyl ring that can be optionally interrupted by O, S, $NR^c$, or C=O;

Y is selected from the group consisting of $CR^bR^c$, $C_{2-6}$ alkylene and $C_{2-6}$ alkenylene, wherein said alkylene and alkenylene linkers can be optionally interrupted by O, S, or $NR^c$;

Z is selected from the group consisting of O, S, $NR^c$, C=O, O(C=O), (C=O)O, $NR^c(C=O)$ or $(C=O)NR^c$;

and the pharmaceutically acceptable salts thereof.

In the compounds of the present invention, X is preferably selected from the group consisting of O and N—$OR^a$. More preferably, X is selected from the group consisting of O, N—OH and N—$OCH_3$.

In the compounds of the present invention, $R^1$ is preferably selected from the group consisting of hydrogen and $C_{1-6}$alkyl, wherein said alkyl group is either unsubstituted or substituted with a group selected from $OR^c$ or $C(=O)R^c$.

In the compounds of the present invention, $R^2$ is preferably selected from the group consisting of hydrogen, hydroxy, iodo, and $C_{1-6}$alkyl, wherein said alkyl group is either unsubstituted or substituted with a group selected from $OR^c$ or $C(=O)R^c$.

In the compounds of the present invention, $R^3$ is preferably selected from the group consisting of hydrogen, chloro, bromo, iodo, cyano, $C_{1-10}$alkyl, $C_{2-10}$alkenyl, aryl and heteroaryl, wherein said alkyl, alkenyl, aryl and heteroaryl groups are either unsubstituted or independently substituted with 1, 2 or 3 groups selected from fluoro, chloro, bromo, iodo, cyano, $OR^a$, $NR^aR^c$, $C(=O)R^a$, $CO_2R^c$, $NR^aC(=O)R^c$, $CONR^aR^c$, $CSNR^aR^c$, $SR^a$, $YR^d$, and $ZYR^d$.

In the compounds of the present invention, $R^3$ is more preferably selected from the group consisting of hydrogen, chloro, bromo, iodo, cyano, $C_{1-10}$alkyl and aryl, wherein said alkyl and aryl groups are either unsubstituted or independently substituted with 1, 2 or 3 groups selected from fluoro, $NR^aR^c$, $OR^a$, $YR^d$, and $ZYR^d$.

In the compounds of the present invention, $R^4$ is preferably selected from the group consisting of hydrogen, fluoro, hydroxy and methyl;

In the compounds of the present invention, $R^5$ and $R^6$ are each independently preferably selected from the group consisting of hydrogen, fluoro, $O(C=O)R^c$ and $OR^a$.

In the compounds of the present invention, $R^5$ is more preferably selected from the group consisting of hydrogen and fluoro.

In the compounds of the present invention, $R^6$ is more preferably selected from the group consisting of $OR^a$ and $O(C=O)R^c$.

In the compounds of the present invention, $R^7$ is preferably selected from the group consisting of hydrogen, $NR^bR^c$, chloro, bromo, nitro and $C_{1-6}$alkyl.

In the compounds of the present invention, $R^8$ and $R^9$ are each independently preferably selected from the group consisting of hydrogen and $C_{1-6}$alkyl, or $R^8$ and $R^9$, when taken together with the carbon atom to which they are attached, form a carbonyl group.

In the compounds of the present invention, $R^{10}$ is preferably selected from the group consisting of hydrogen, $C_{1-10}$alkyl, $C_{2-10}$alkenyl, $C_{3-6}$cycloalkyl, and cycloalkylalkyl, wherein said alkyl, alkenyl, cycloalkyl and cycloalkylalkyl groups can be optionally substituted with a group selected from $OR^b$, $SR^b$, $C(=O)R^b$, or 1–5 fluoro, or $R^{10}$ and $R^1$, when taken together with three intervening carbon atoms to which they are attached, form a 5–6 membered cycloalkyl ring which can be optionally substituted with $C_{1-6}$alkyl.

In the compounds of the present invention, $R^{11}$ is preferably selected from the group consisting of hydrogen and $C_{1-4}$alkyl.

An embodiment of the invention is a method of eliciting an estrogen receptor modulating effect in a mammal in need thereof, comprising administering to the mammal a therapeutically effective amount of any of the compounds or any of the above pharmaceutical compositions described above.

A class of the embodiment is the method wherein the estrogen receptor modulating effect is an antagonizing effect.

A subclass of the embodiment is the method wherein the estrogen receptor is an ERα receptor.

A second subclass of the embodiment is the method wherein the estrogen receptor is an ERβ receptor.

A third subclass of the embodiment is the method wherein the estrogen receptor modulating effect is a mixed ERα and ERβ receptor antagonizing effect.

A second class of the embodiment is the method wherein the estrogen receptor modulating effect is an agonizing effect.

A subclass of the embodiment is the method wherein the estrogen receptor is an ERα receptor.

A second subclass of the embodiment is the method wherein the estrogen receptor is an ERβ receptor.

A third subclass of the embodiment is the method wherein the estrogen receptor modulating effect is a mixed ERα and ERβ receptor agonizing effect.

A third class of the embodiment is the method wherein the ERα receptor is an agonizing and antogonizing effect.

A fourth class of the embodiment is the method wherein the ERβ receptor is an agonizing and antagonizing effect.

A fifth class of the embodiment is the method wherein the estrogen receptor modulating effect is a mixed ERα and ERβ receptor agonizing and antagonizing effect.

Another embodiment of the invention is a method of treating or preventing hot flashes in a mammal in need thereof by administering to the mammal a therapeutically effective amount of any of the compounds or pharmaceutical compositions described above.

Another embodiment of the invention is a method of treating or preventing anxiety in a mammal in need thereof by administering to the mammal a therapeutically effective amount of any of the compounds or pharmaceutical compositions described above.

Another embodiment of the invention is a method of treating or preventing depression in a mammal in need thereof by administering to the mammal a therapeutically effective amount of any of the compounds or pharmaceutical compositions described above.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Further exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, cartilage degeneration, endometriosis, uterine fibroid disease, breast cancer, uterine cancer, prostate cancer, hot flashes, cardiovascular disease, impairment of congnitive functioning, cerebral degenerative disorder, restenosis, vascular smooth muscle cell proliferation, incontinence, and/or disorders related to estrogen functioning.

The present invention is also directed to combinations of any of the compounds or any of the pharmaceutical compositions described above with one or more agents useful in the prevention or treatment of osteoporosis. For example, the compounds of the instant invention may be effectively administered in combination with effective amounts of other agents such as an organic bisphosphonate or a cathepsin K inhibitor. Nonlimiting examples of said organic bisphosphonates include alendronate, clodronate, etidronate, ibandronate, incadronate, minodronate, neridronate, risedronate, piridronate, pamidronate, tiludronate, zoledronate, pharmaceutically acceptable salts or esters thereof, and mixtures thereof. Preferred organic bisphosphonates include alendronate and pharmaceutically acceptable salts and mixtures thereof. Most preferred is alendronate monosodium trihydrate.

The precise dosage of the bisphonate will vary with the dosing schedule, the oral potency of the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 μg/kg body weight and preferably about 10 to about 2000 μg/kg of body weight.

For human oral compositions comprising alendronate, pharmaceutically acceptable salts thereof, or pharmaceutically acceptable derivatives thereof, a unit dosage typically comprises from about 8.75 mg to about 140 mg of the alendronate compound, on an alendronic acid active weight basis, i.e. on the basis of the corresponding acid.

For use in medicine, the salts of the compounds of this invention refer to non-toxic "pharmaceutically acceptable salts." Other salts may, however, be useful in the preparation of the compounds according to the invention or of their pharmaceutically acceptable salts. When the compounds of the present invention contain a basic group, salts encompassed within the term "pharmaceutically acceptable salts" refer to non-toxic salts which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention can have chiral centers and occur as racemates, racemic mixtures, diastereomeric mixtures, and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs, hydrates and solvates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "bone resorption," as used herein, refers to the process by which osteoclasts degrade bone.

The term "alkyl" shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, etc.).

The term "alkenyl" shall mean a substituting univalent group derived by conceptual removal of one hydrogen atom from a straight or branched-chain acyclic unsaturated hydrocarbon containing at least one double bond (i.e., —$CH=CH_2$, —$CH_2CH=CH_2$, —$CH=CHCH_3$, —$CH_2CH=C(CH_3)_2$, etc.).

The term "alkynyl" shall mean a substituting univalent group derived by conceptual removal of one hydrogen atom from a straight or branched-chain acyclic unsaturated hydrocarbon containing at least one triple bond (i.e., —$C\equiv CH$, —$CH_2C\equiv H$, —$C\equiv CCH_3$, —$CH_2C\equiv CCH_2(CH_3)_2$, etc.).

The term "alkylene" shall mean a substituting bivalent group derived from a straight or branched-chain acyclic saturated hydrocarbon by conceptual removal of two hydrogen atoms from different carbon atoms (i.e., —$CH_2CH_2$—, —$CH_2CH_2CH_2CH_2$—, —$CH_2C(CH_3)_2CH_2$—, etc.).

The term "alkylidene" shall mean a substituting bivalent group derived from a straight or branched-chain acyclic saturated hydrocarbon by conceptual removal of two hydrogen atoms from the same carbon atom (i.e., =$CH_2$, =$CHCH_3$, =$C(CH_3)_2$, etc.).

The term "alkenylene" shall mean a substituting bivalent group derived from a straight or branched-chain acyclic unsaturated hydrocarbon by conceptual removal of two hydrogen atoms from different carbon atoms (i.e., —$CH=CH$—, —$CH_2CH=CH$—, $CH_2CH=CHCH_2$—, —$C(CH_3)=C(CH_3)$—, etc.).

The term "cycloalkyl" shall mean a substituting univalent group derived by conceptual removal of one hydrogen atom from a saturated monocyclic hydrocarbon (i.e., cyclopropyl, cyclobutyl, cyclopentyl, cyclohexyl, or cycloheptyl).

The term "cycloalkenyl" shall mean a substituting univalent group derived by conceptual removal of one hydrogen atom from an unsaturated monocyclic hydrocarbon containing a double bond (i.e., cyclopentenyl or cyclohexenyl).

The term "heterocycloalkyl" shall mean a substituting univalent group derived by conceptual removal of one hydrogen atom from a heterocycloalkane wherein said heterocycloalkane is derived from the corresponding saturated monocyclic hydrocarbon by replacing one or two carbon atoms with atoms selected from N, O or S. Examples of heterocycloalkyl groups include, but are not limited to, oxiranyl, azetidinyl, pyrrolidinyl, piperidinyl, piperazinyl, and morpholinyl. Heterocycloalkyl substituents can be attached at a carbon atom. If the substituent is a nitrogen containing heterocycloalkyl substituent, it can be attached at the nitrogen atom.

The term "aryl" as used herein refers to a substituting univalent group derived by conceptual removal of one hydrogen atom from a monocyclic or bicyclic aromatic hydrocarbon. Examples of aryl groups are phenyl, indenyl, and naphthyl.

The term "heteroaryl" as used herein refers to a substituting univalent group derived by the conceptual removal of one hydrogen atom from a monocyclic or bicyclic aromatic ring system containing 1, 2, 3, or 4 heteroatoms selected from N, O, or S. Examples of heteroaryl groups include, but are not limited to, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, and purinyl. Heteraryl substituents can be attached at a carbon atom or through the heteroatom.

In the compounds of the present invention, alkyl, alkenyl, alkynyl, alkylidene, alkenylene, cycloalkyl, cycloalkenyl, heterocycloalkyl, aryl and heteroaryl groups can be further substituted by replacing one or more hydrogen atoms by alternative non-hydrogen groups. These include, but are not limited to, halo, hydroxy, mercapto, amino, carboxy, cyano and carbamoyl.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluyl, ethylphenyl, and propylphenyl.

The term "heteroarylalkyl," as used herein, shall refer to a system that includes a heteroaryl portion, where heteroaryl is as defined above, and contains an alkyl portion. Examples of heteroarylalkyl include, but are limited to, pyridylmethyl, pyridylethyl and imidazoylmethyl.

The term "cycloalkylalkyl," as used herein, shall refer to a system that includes a 3- to 8-membered fully saturated cyclic ring portion and also includes an alkyl portion, wherein cycloalkyl and alkyl are as defined above.

In the compounds of the present invention, $R^1$ and $R^2$ can be taken together with the carbon atom to which they are attached to form a 3–6 membered ring.

In the compounds of the present invention, $R^a$ and $R^b$ can be taken together with any of the atoms to which they may be attached or are between them to form a 4–6 membered ring system.

The term "halo" shall include iodo, bromo, chloro and fluoro.

The term "oxy" means an oxygen (O) atom. The term "thio" means a sulfur (S) atom. The term "oxo" means =O. The term "oximino" means the =N—O group.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

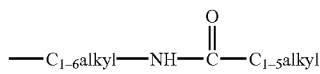

In choosing compounds of the present invention, one of ordinary skill in the art will recognize that the various substituents, i.e. $R^1$, $R^2$, $R^3$, $R^4$, $R^5$, $R^6$, $R^7$, $R^8$, $R^9$, $R^a$, $R^b$, $R^c$, $YR^d$ and $ZYR^d$ are to be chosen in conformity with well-known principles of chemical structure connectivity.

Representative compounds of the present invention typically display submicromolar affinity for alpha and/or beta estrogen receptors. Compounds of this invention are therefore useful in treating mammals suffering from disorders related to estrogen functioning. Pharmacologically effective amounts of the compound, including the pharmaceutically effective salts thereof, are administered to the mammal, to treat disorders related to estrogen functioning, such as bone loss, hot flashes and cardiovascular disease.

The compounds of the present invention are available in racemic form or as individual enantiomers. For convenience, some structures are graphically represented as a single enantiomer but, unless otherwise indicated, is meant to include both racemic and enantiomeric forms.

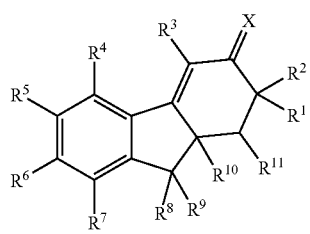

It is generally preferable to administer compounds of structure (I) as enantiomerically pure formulations since most or all of the desired bioactivity resides with a single enantiomer. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The compounds of the present invention can be used in combination with other agents useful for treating estrogen-mediated conditions. The individual components of such combinations can be administered separately at different times during the (course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixers, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The novel compounds of the present invention can be prepared according to the procedure of the following schemes and examples, using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The compounds of the present invention are prepared according to the general methods outlined in Schemes I–VIII. In these schemes, $R^I$ represents one or more of $R^4$, $R^5$, $R^6$, and $R^7$, or precursors thereof; $R^{Ia}$ and $R^{Ib}$ represent non-hydrogen values of $R^4$, $R^5$, $R^6$, or $R^7$, or precursors thereof; $CHR^{II}R^{III}$ and $CR^{III}$=$CR^{IIa}R^{IIb}$ represent non-hydrogen values of $R^{10}$, or precursors thereof; $R^{IV}$ represents $R^3$ or a precursor thereof; $R^{IVa}$ and $R^{IVb}$ represent non-hydrogen values of $R^3$, or precursors thereof; $R^{Va}$, $R^{Vb}$ and $CH(OH)R^{Vc}$ represent non-hydrogen values of $R^1$ and $R^2$, or precursors thereof; $R^{VI}$ represents non-hydrogen $R^{11}$; $R^{VII}$ represents a non-hydrogen value of $R^8$ or $R^9$; $R^{VIII}$ represents $OR^a$ and $NR^aR^b$; and $R^{IX}$ represents hydrogen or a $C_{1-5}$ alkyl group.

The fundamental methods for construction of 9a-substituted 1,2,9,9a-tetrahydro-3H-fluoren-3-one compounds are illustrated in Scheme I, and are based on chemistry described by Cragoe, et al., *J. Med. Chem.* 1986, 29, 825–841. In step 1 of Scheme I, a 2-substituted-1-indanone (1b) is reacted with a vinyl ketone in the presence of base to provide the diketone (2). The diketone is then cyclized (step 2) under basic or acidic conditions to provide the tetrahydrofluorenone product (3a). Alternatively, a 2-alkylidene-1-indanone of type (1a), wherein $R^{II}$ is a carbon atom substituted with at least one hydrogen atom, reacts with a vinyl ketone in the presence of base to give the diketone (4). Cyclization of this intermediate affords a 9a-vinyl substituted tetrahydrofluorenone (5). In step 1, if one of $R^I$ is NHAc, it also reacts with the vinyl ketone to form an N—$CH_2CH_2COCH_2R^{IV}$ derivative. This group, as well as the acetyl group, can be removed at a later stage using excess sodium hydroxide in ethanol.

Representative reagents and reaction conditions indicated in Scheme I as steps 1 and 2 are as follows:

| Step 1 | $CH_2$=$CHC(O)CH_2R^{IV}$, DBN, THF, rt to 60° C. or $CH_2$=$CHC(O)CH_2R^{IV}$, NaOMe, MeOH, rt to 60° C. |
|---|---|
| Step 2 | NaOH, $H_2O$, MeOH or EtOH, rt to 85° C. or pyrrolidine, HOAc, THF or PhMe, 60–85° C. or 6N HCl, HOAc, 90–100° C. |

SCHEME I

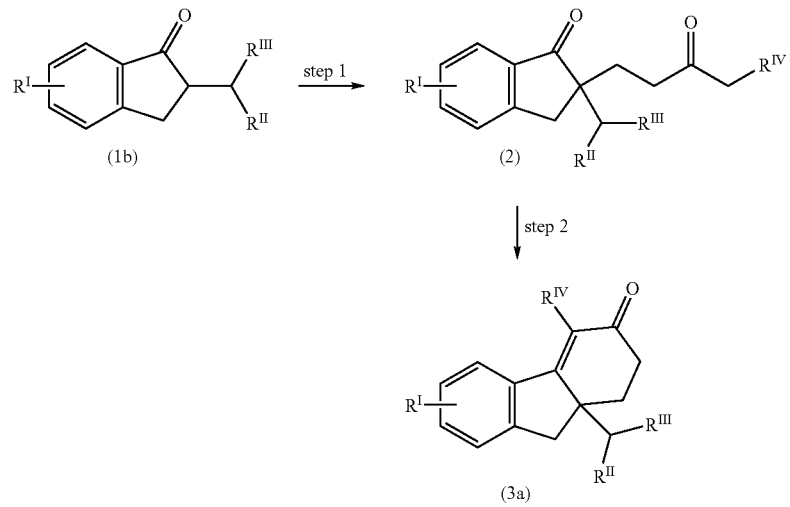

-continued

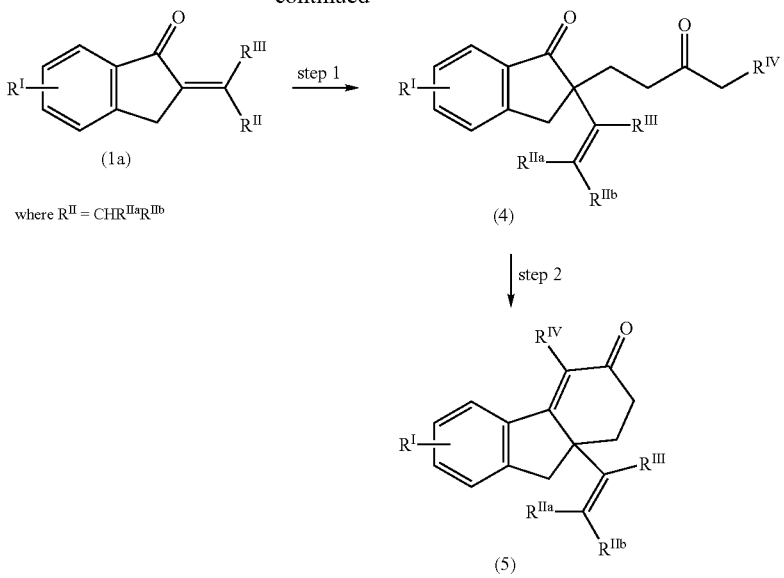

The indanone starting materials (1a) and (1b) of Scheme I are either known compounds or they can be prepared by conventional methods as outlined in Scheme II. Steps 1–3 of Scheme II, which produce the 2-substituted-1-indanones (1b), are described in Cragoe, et al., *J. Med. Chem.* 1982, 25, 567–579 and references cited therein, and in Cragoe, et al., *J. Med. Chem.* 1986, 29, 825–841. The 2-alkylidene-1-indanones (1a) are prepared by reacting 2-unsubstituted indanones (9) with aldehydes or ketones under basic conditions. Reduction of the double bond (step 5) affords the indanone (1b). Steps 4 and 5 of Scheme II can be combined to to provide (1b) directly from (9). Alternatively, 2-substituted indanones (1b) are obtained by reacting indanones (9) with suitable alkylating agents in the presence of a base (step 6, Scheme II). Numerous 2-unsubstituted-1-indanone starting materials of type (9) are known and other examples can be prepared by procedures analogous to those used to prepare the known compounds.

Representative reagents and reaction conditions indicated in Scheme II as steps 1–6 are as follows:

| | |
|---|---|
| Step 1 | $R^{III}R^{II}CHCH_2COCl$, $AlCl_3$, $CH_2Cl_2$, 0° C. to rt |
| Step 2 | $CH_2(NMe_2)_2$, $Ac_2O$, 95° C. or HCHO, $K_2CO_3$, MeOH, rt |
| Step 3 | $H_2SO_4$, 0° C. to 50° C. |
| Step 4 | $R^{II}COR^{III}$, KOH or NaOMe, EtOH, 0° C. to rt or LDA, THF, −78° C. then $R^{II}COR^{III}$, −78° C. to rt when $R^{II}COR^{III}$ is an aldehyde |
| | $R^{II}COR^{III}$, LiN(iPr)$_2$, HMPA, −78° C. to rt when $R^{II}COR^{III}$ is a ketone |
| Step 5 | $H_2$, 10% Pd/C or 20% Pd(OH)$_2$/C, EtOH or EtOAc, rt |
| Steps 4 and 5 can be combined | $R^{II}COR^{III}$, KOH, $H_2$, 10% Pd/C, EtOH, rt or $R^{II}COR^{III}$, NaOMe, $H_2$, 20% Pd(OH)$_2$/C, EtOH, rt |
| Step 6 | $R^{III}R^{II}CHX$, NaH, DMF, 0° C. to rt where X is Br, I, or $OSO_2CF_3$ |

SCHEME II

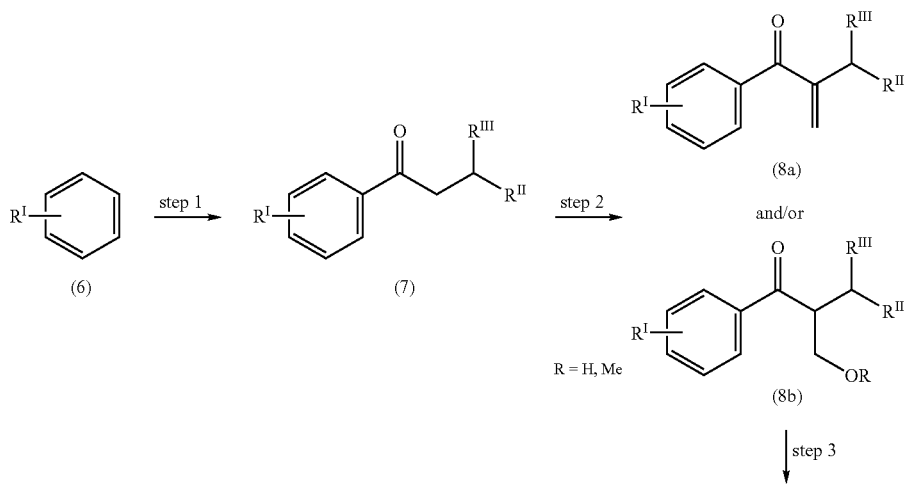

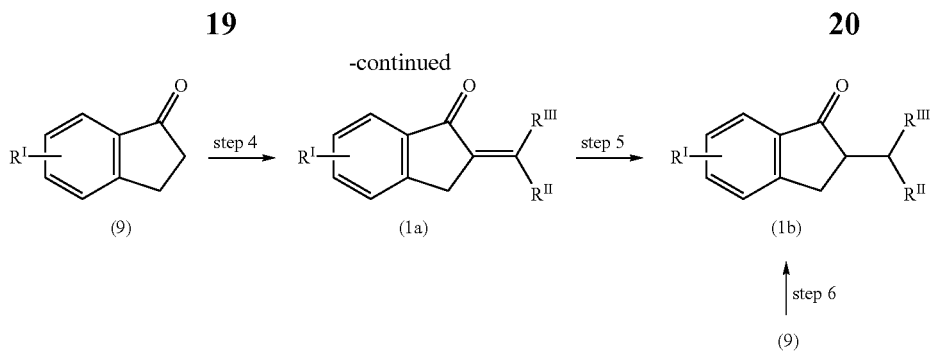

When the indanones (9) and (1b) contain one or two open sites adjacent to an electron donating $R^I$ group such as $OCH_3$ or NHAc, the aromatic ring can be further functionalized as outlined in Scheme III. Electrophilic aromatic substitution (step 1 of Scheme III) introduces one or two new substituents $R^{Ia}$ ortho to the $R^I$ group. Certain $R^{Ia}$ groups can be further transformed (step 2 of Scheme III) to a wide variety of new substituents $R^{Ib}$ using well established methods. For example, intermediate (11a) wherein $R^{Ia}$ is bromo is converted to derivatives (11b) wherein $R^{Ib}$ is alkyl or alkenyl using Stille or Suzuki coupling procedures. If $R^{Ia}$ of (11a) is a nitro group, catalytic hydrogenation provides the corresponding amino derivative which can be acetylated to provide intermediate (11b) wherein $R^{Ib}$ is NHAc. The substituted indanones (11a) and (11b) are converted into the tetrahydrofluorenones (3b) and (3c) by the procedures previously described in Scheme I. Certain $R^{Ib}$ groups can be further manipulated. For example, reduction of a vinyl group affords an alkyl group, and an amino group can be acylated or diazotized and converted to other $R^{Ib}$ groups such as $OR^a$.

Representative reagents and reaction conditions indicated in Scheme III as steps 1 and 2 are as follows:

| Step 1 | NCS, MeCN or DMF, rt to 60° C. or | $R^{Ia}$ = Cl |
|---|---|---|
|  | NBS, MeCN or DMF, rt to 60° C. or | $R^{Ia}$ = Br |
|  | $HNO_3$, $H_2SO_4$, −20° C. or 90% $HNO_3$, 0° C. | $R^{Ia}$ = $NO_2$ |
| Step 2 | Stille and Suzuki couplings on $R^{Ia}$ = Br |  |
|  | $Me_4Sn$, $PdCl_2(PPh_3)_2$, LiCl, DMF, 100° C. or | $R^{Ib}$ = Me |
|  | $Bu_3SnCH=CH_2$, $Pd(PPh_3)_4$, PhMe, 100° C. or | $R^{Ib}$ = $CH=CH_2$ |
|  | $PhB(OH)_2$, $Pd(PPh_3)_4$, $Cs_2CO_3$, DMF, 100° C. | $R^{Ib}$ = Ph |
|  | Reduction of $R^{Ia}$ = $NO_2$ |  |
|  | $H_2$, 10% Pd/C, EtOH or EtOAc, rt | $R^{Ib}$ = $NH_2$ |

SCHEME III

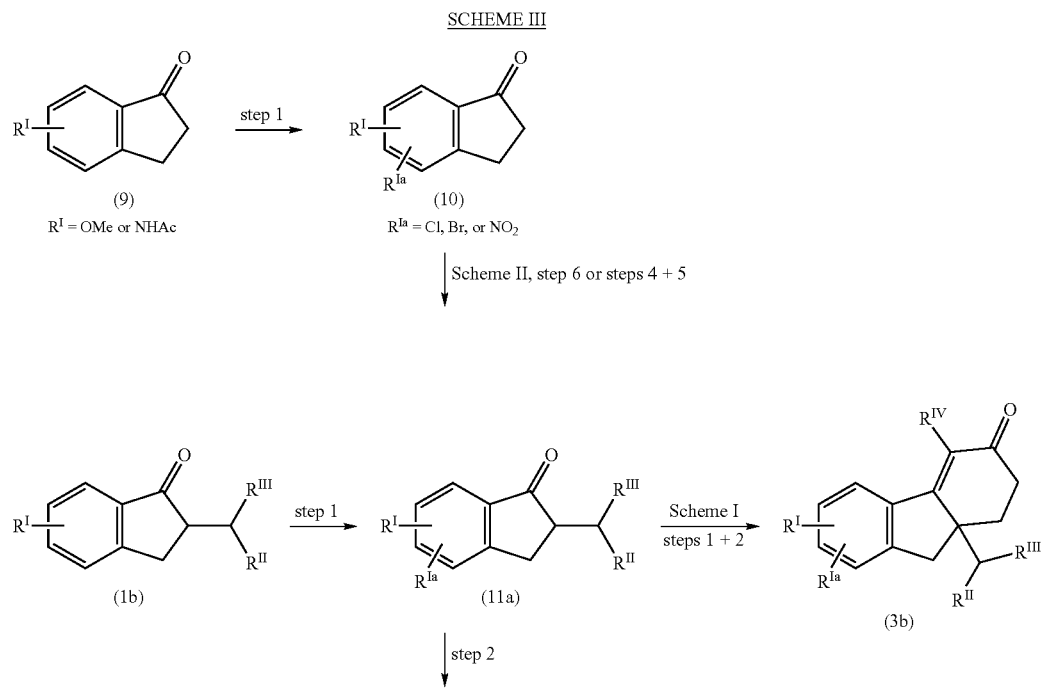

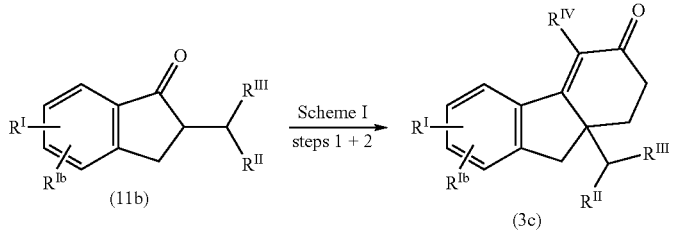

Tetrahydrofluorenones of types (3a), (3b) and (3c) wherein $R^{IV}$ is hydrogen can be functionalized at the 4-position by the methods illustrated in Scheme IV for compound (3a). Bromination or iodination (step 1) affords the 4-halo intermediates (3d). These compounds can be converted (step 2) by known methods into a variety of new derivatives (3e) wherein $R^{IVb}$ is alkyl, alkenyl, alkynyl, aryl, heteroaryl, CN, $OR^a$, $NR^aNR^b$, and $SR^a$. If the group $R^{IVb}$ is, or contains, a functional group capable of further modification, this can be carried out to produce additional derivatives. For example, a $R^{IVb}$ cyano group can be hydrolyzed to a carboxyl group which in turn can be converted to carbamoyl groups.

Representative reagents and reaction conditions indicated in Scheme IV as steps 1 and 2 are as follows:

| Step 1 | NCS, CCl$_4$, rt | $R^{IVa}$ = Cl |
|---|---|---|
| | Br$_2$, NaHCO$_3$, CH$_2$Cl$_2$ or CCl$_4$, 0° C. to rt or | $R^{IVa}$ = Br |
| | I$_2$, NaHCO$_3$, H$_2$O, CH$_2$Cl$_2$, rt | $R^{IVa}$ = I |
| Step 2 | $R^{IVb}$SnBu$_3$, PdCl$_2$(PPh$_3$)$_2$, PhMe, 100–110° C. or $R^{IVb}$SnBu$_3$, Pd(PPh$_3$)$_4$, PhMe, 100° C. or $R^{IVb}$B(OH)$_2$, PdCl$_2$(PPh$_3$)$_2$, Cs$_2$CO$_3$, DMF, 100° C. or $R^{IVb}$B(OH)$_2$, Pd(PPh$_3$)$_4$, aq Na$_2$CO$_3$, PhMe, 80° C. | $R^{IVb}$ = alkenyl, aryl, or heteroaryl |
| | ($R^{IVb}$)$_3$B, PdCl$_2$(dppf).CH$_2$Cl$_2$, | $R^{IVb}$ = alkyl |
| | Ph$_3$As, Cs$_2$CO$_3$, H$_2$O, THF, DMF, 60° C. $R^{IVb}$Sn(CH$_2$CH$_2$CH$_2$)$_3$N, Pd(PPh$_3$)$_4$, PhMe, 100° C. | $R^{IVb}$ = alkenyl, alkyl, or arylalkyl |
| | CuCN, NMP, 160° C. | $R^{IVb}$ = CN |

SCHEME IV

Methods for introduction of substituents at the 2-position are illustrated in Scheme V for the tetrahydrofluorenone derivative (3a). These methods apply equally well to other tetrahydrofluorenones such as (3b), (3c), (3d), (3e), and (5). In general terms, the 2-unsubstituted tetrahydrofluorenone is treated with a strong base and the resulting ketone enolate is trapped with an appropriate electrophilic reagent (step 1). If the electrophile is an alkylating agent of the type $R^{Va}X$, then both monoalkylated (12) and dialkylated products (13a) are obtained, depending on the specifics of the reaction conditions. The monoalkylated derivatives (12) can be converted to disubstituted products (13b) by repeating the procedure (step 2) using the same or a different electrophilic reagent. This well known methodology leads to a variety of products wherein $R^{Va}$ and $R^{Vb}$ are, inter alia, alkyl, alkenyl, hydroxy, bromo, and iodo. The ketone enolate can also be trapped with aldehydes (step 3) to afford 2-alkylidene derivatives (14) and 2-hydroxyalkyl derivatives (15). Where appropriate, the newly introduced 2-substituent can be further manipulated to produce additional derivatives. For example, an $R^{Va}$ allyl group can be oxidized to $CH_2CHO$ which is reduced in a subsequent step to $CH_2CH_2OH$.

Scheme V also illustrates a special case of C-2 functionalization that provides for 2,9a-bridged products of type (13c). In this case, $R^{Vd}$ of (12a) is hydrogen or $R^{Va}$ and $R^{III}$ of (12a) is an alkyl group containing an electrophilic moiety such as an iodo, bromo, aldehyde, or keto group. Enol generation at C-2 (step 4) is followed by intramolecular reaction at the $R^{III}$ electrophilic center to afford a bridged

| | -continued |
|---|---|
| Step 4 | LDA, THF, 0° C. then $R^{Vc}$CHO, −78° C. to rt or EtOCHO, NaH, PhH, rt (gives 14, $R^{Vc}$ = OH) LDA, THF, −78° C. to rt or NaH, DMF, 0° C. to rt |

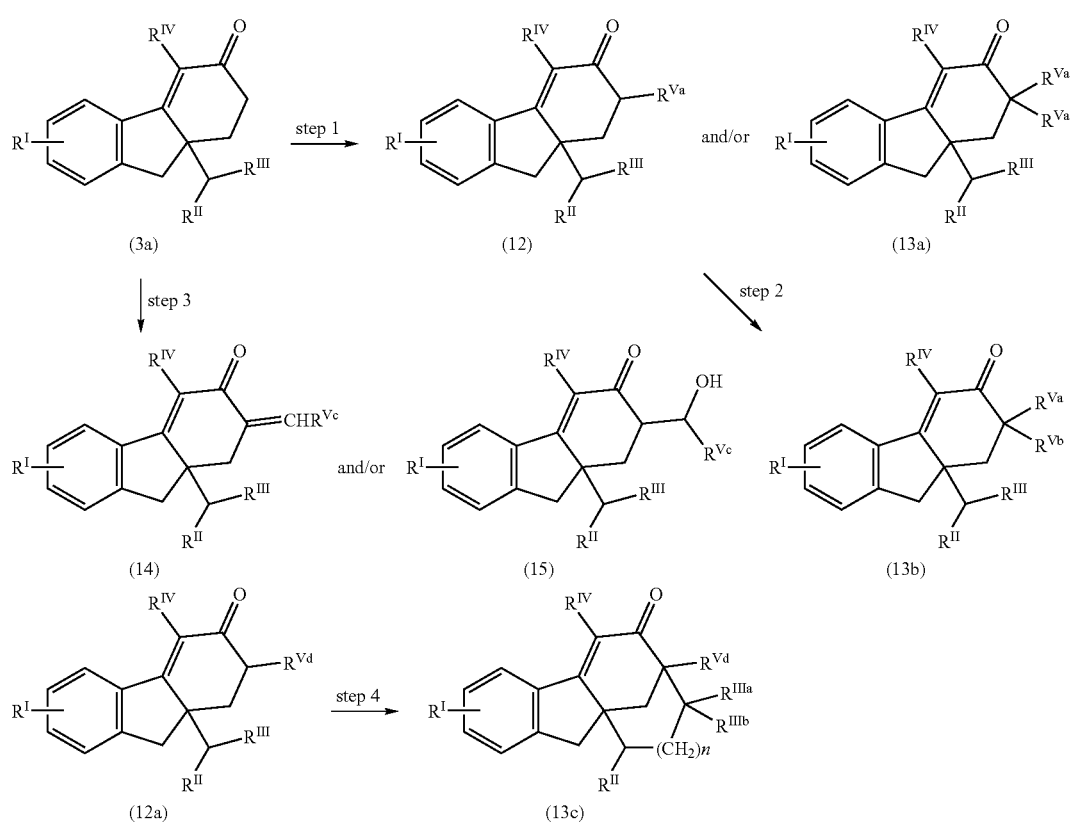

SCHEME V product of type (13c). This compound can be deblocked or modified and then deblocked to provide the final product. For example, if $R^{IIIa}$ is a hydroxy group, modifications include acylation, oxidation, dehydration, and dehydration followed by reduction.

Representative reagents and reaction conditions indicated in Scheme V as steps 1–3 are as follows:

| Step 1 | $R^{Va}$X, NaH, DMF, 0° C. to rt (X = Br, I) or LDA, THF, 0° C. then $R^{Va}$X, −78° C. to rt | $R^{Va}$ = alkyl, alkenyl |
| | i) LDA, THF, 0° C. then TMSCl, −78° C. to rt ii) MCPBA, NaHCO$_3$, CH$_2$Cl$_2$, rt | $R^{Va}$ = OH |
| | I$_2$, pyridine, CH$_2$Cl$_2$, rt to 60° C. or LDA, THF, 0° C. then I$_2$, −78° C. to rt | $R^{Va}$ = I |
| Step 2 | same as step 1 except use $R^{Vb}$X to introduce a different alkyl or alkenyl group | |
| Step 3 | $R^{Vc}$CHO, KOH, MeOH or EtOH, rt or | |

Alkyl substituents are introduced at the 1-position of the tetrahydrofluorenone platform as outlined in Scheme VI for the derivative (3a). In step 1, oxidation of the cyclohexenone ring provides the cyclohexadienone (16). Alternatively, (16) is prepared by base treatment of the 2-bromo or 2-iodo derivatives (12). Treatment of the dienone intermediate with an appropriate organometallic species serves to install the C-1 substituent $R^{VI}$.

Representative reagents and reaction conditions indicated in Scheme VI as steps 1–3 are as follows:

| Step 1 | DDQ, dioxane, 80–100° C. |
|---|---|
| Step 2 | DBN, DMSO, 80–100° C. |
| Step 3 | $R^{VI}$MgBr. CuBr.SMe$_2$, THF, −78° C. to rt or $R^{VI}_2$CuLi, Et$_2$O or THF, −50° C. to 0° C. |

SCHEME VI

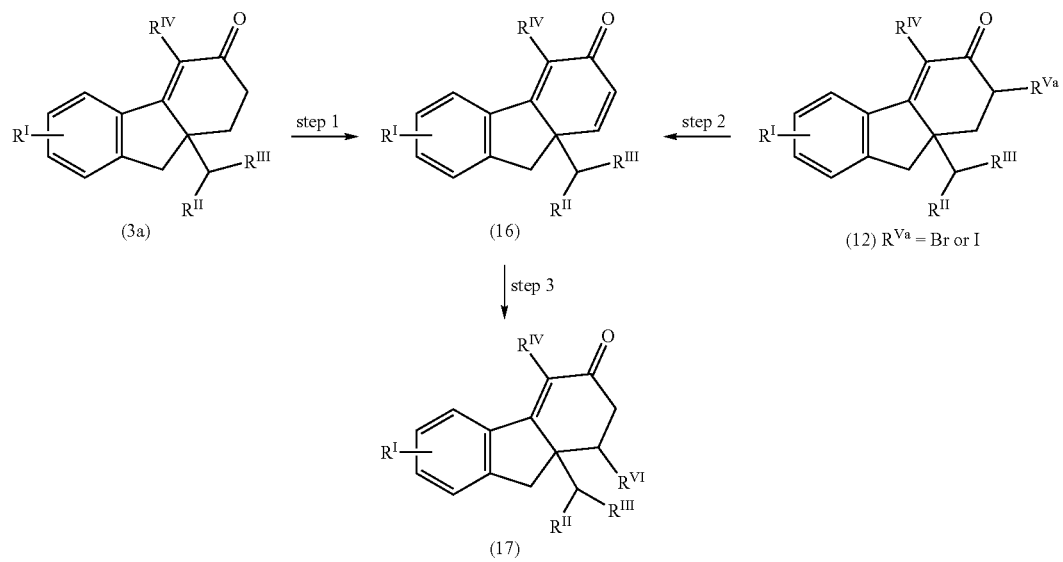

3-Substituted-1-indanones of type (18), which are known or can be prepared by the route described in *J. Med. Chem.* 1981, 24, 457–462, are converted to 9-substituted tetrahydrofluorenones of types (20a) and (20b) by the methods outlined in Scheme VII. Reductive alkylation (step 1) of (18) with the appropriate aldehyde affords intermediate (19) which is deblocked and cyclized under acidic conditions (step 2) to afford the product (20b). Alternatively, compound (18) can be converted to the 9-substituted tetrahydrofluorenone product (20a) using procedures previously described in Schemes I and II. This methodology is also used to prepare 9,9a-unsubstituted derivatives (20b) wherein $R^{VII}$ is hydrogen and, by extension to 3,3-disubstituted-1-indanones, 9,9-disubstituted tetrahydrofluorenone derivatives. Also shown in Scheme VII is a method for preparing 9-oxo tetrahydrofluorenones (23) from indan-1,3-diones (22), which are available by condensation of phthalates (21) with the appropriate ketone.

Representative reagents and reaction conditions indicated in Scheme VII as steps 1–3 are as follows:

| | |
|---|---|
| Step 1 | OHCCH$_2$C(OCH$_2$CH$_2$O)CH$_2$R$^{IV}$, KOH, EtOH, rt, then H$_2$, 10% Pd/C, EtOH, rt |
| Step 2 | 6N HCl, HOAc, 125° C. |
| Step 3 | (R$^{III}$R$^{II}$CHCH$_2$)$_2$CO, NaH, DMF, rt |

SCHEME VII

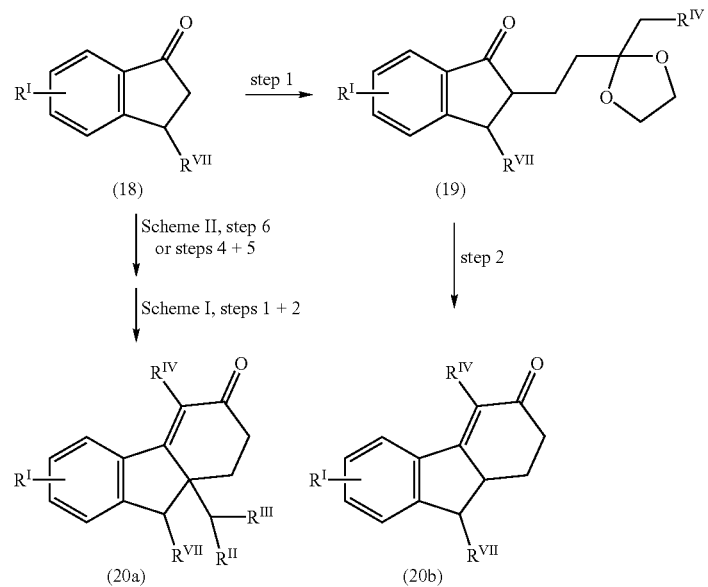

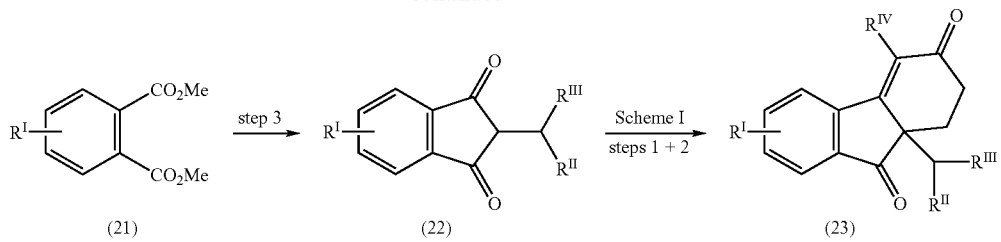

Modifications to the C-3 ketone are outlined in Scheme VIII for the tetrahydrofluorenone derivative (3a). The methodology also applies to the other tetrahydrofluorenone products prepared according to Schemes III–VII. In step 1, the ketone is reacted with a hydroxyl amine, alkoxyamine, or hydrazine reagent to yield the 3-imino product (24). Products are typically obtained as separable mixtures of E- and Z-isomers about the imino double bond. Ketone (3a) also reacts with ylide reagents (step 2) to afford 3-alkylidene derivatives (25).

Representative reagents and reaction conditions indicated in Scheme VIII as steps 1 and 2 are as follows:

| Step 1 | NH$_2$OR$^a$.HCl, pyridine, rt to 60° C. or NH$_2$NR$^a$R$^b$, EtOH, rt |
|---|---|
| Step 2 | Ph$_3$P$^+$CH$_2$R$^{IX}$ Br$^-$, BuLi, THF, 0 to 50° C. |

In Schemes I–VIII, the various R groups often contain protected functional groups which are deblocked by conventional methods. The deblocking procedure can occur at the last step or at an intermediate stage in the synthetic sequence. For example, if one of R$^I$ is a methoxyl group, it can be converted to a hydroxyl group by any of a number of methods. These include exposure to BBr$_3$ in CH$_2$Cl$_2$ at −78° C. to room temperature, heating with pyridine hydrochloride at 190–200° C., or treatment with EtSH and AlCl$_3$ in CH$_2$Cl$_2$ at 0° C. to room temperature. Another example involves the use of methoxymethyl (MOM) protection of alcohols and phenols. The MOM group is conveniently removed by exposure to hydrochloric acid in aqueous methanol. Other well known protection-deprotection schemes can be used to prevent unwanted reactions of various functional groups contained in the various R substituents.

The following specific examples, while not limiting, serve to illustrate the methods of preparation of the 1,2,9,9a-tetrahydro-3H-fluoren-3-one compounds of the present

SCHEME VIII

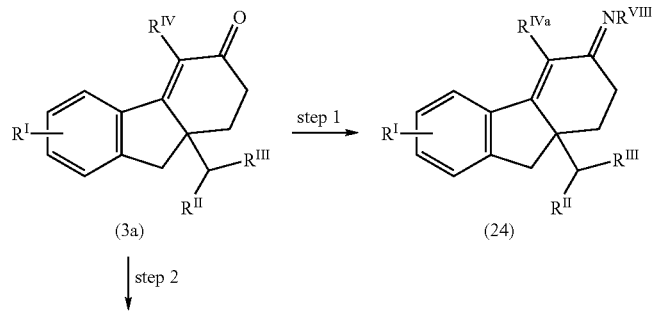

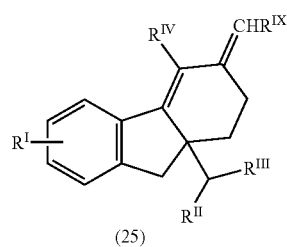

EXAMPLE 1

SYNTHESIS OF 4-BROMO-7-HYDROXY-9a-METHYL-1,2,9,9a-TETRAHYDRO-3H-FLUOREN-3-ONE

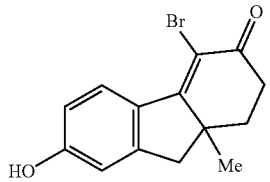

Step 1: 3-hydroxy-2-methyl-1-[4-(methoxy)phenyl]-1-propanone and 2-methyl-1-[4-(methoxy)phenyl]-2-propen-1-one A mixture of 1-[4-(methoxy)phenyl]-1-propanone (2.0 g, 12.2 mmol), 37% formaldehyde in water (1.1 mL, 14.6 mmol), and $K_2CO_3$ (1.68 g, 12.2 mmol) in methanol (12 mL) was stirred at room temperature for 4 days, treated with more $K_2CO_3$ (1.7 g), and stirred at room temperature for an additional 3 days. The mixture was diluted with EtOAc (50 mL), washed with water (50 mL) and brine (20 mL), dried over $MgSO_4$, filtered, and evaporated under vacuum to a clear oil (2.43 g). Proton NMR revealed a mixture of 3-hydroxy-2-methyl-1-[4-(methoxy)phenyl]-1-propanone (major), 2-methyl-1-[4-(methoxy)phenyl]-2-propen-1-one (minor), and starting material (minor).

$^1$H NMR (CDCl$_3$, 500 MHz) δ 1.21 (d, CH$_3$), 3.45 (m, COCH), 3.76 (m, CH$_2$OH), 3.89 (s, OCH$_3$), 6.96 and 7.99(two m, aryl-H).

Step 2: 5-methoxy-2-methyl-1-indanone

The crude product from step 1 (2.4 g) was added in portions over 10 minutes to ice-cold, conc. H$_2$SO$_4$. The resulting yellow-brown solution was stirred at 0° C. for 1.5 hours, then at room temperature for 1 hour, and finally at 50° C. for 12 hours. After cooling to room temperature, the mixture was partitioned between cold EtOAc (200 mL) and cold water (200 mL). The organic phase was washed with water (200 mL) and brine (100 mL), dried over MgSO$_4$, filtered, and evaporated under vacuum to afford 5-methoxy-2-methyl-1-indanone (1.5 g) as a solid.

$^1$H NMR (CDCl$_3$, 500 MHz) δ 1.31 (d, CH$_3$), 2.69 and 3.36 (two dd, 3-CH$_2$), 2.73 (m, H-2), 3.90 (s, OCH$_3$), 6.89 (br s, H-4), 6.92 (dd, H-6), and 7.71 (d, H-7).

Step 3: 5-methoxy-2-methyl-2-(3-oxo-butyl)-1-indanone

A solution of 5-methoxy-2-methyl-1-indanone (0.5 g, 2.84 mmol) in anhydrous tetrahydrofuran (3 mL) was treated with 1,8-diazabicyclo[5.4.0]undec-7-ene (0.085 mL, 0.57 mmol) and methyl vinyl ketone (0.473 mL, 5.68 mmol). The resulting solution was placed under a nitrogen atmosphere and stirred at room temperature overnight. The mixture was diluted with EtOAc (25 mL), washed with 0.2N HCl (25 mL) and brine (10 mL), dried over MgSO$_4$, filtered, and evaporated under vacuum to a yellow oil (800 mg). The oil was dissolved in CH$_2$Cl$_2$ (10 mL) and the solution added to a small column of EM silica gel 60 (8 mL). The column was eluted with CH$_2$Cl$_2$ (30 ml) and the eluant evaporated under vacuum to afford 5-methoxy-2-methyl-2-(3-oxobutyl)-1-indanone (467 mg) as an oil.

$^1$H NMR (CDCl$_3$, 500 MHz) δ 1.24 (s, CH$_3$), 1.90 (m, CH$_2$CH$_2$CO), 2.11 (s, COCH$_3$), 2.38 (m, CH$_2$CH$_2$CO), 2.89 and 3.00 (two d, 3-CH$_2$), 3.90 (s, OCH$_3$), 6.87 (d, H-4), 6.93 (dd, H-6), and 7.70 (d, H-7).

Step 4: 7-methoxy-9a-methyl-1,2,9,9a-tetrahydro-3H-fluoren-3-one

Pyrrolidine (0.159 mL, 1.9 mmol) and acetic acid (0.109 mL, 1.9 mmol) were added to a solution of 5-methoxy-2-methyl-2-(3-oxo-butyl)-1-indanone (467 mg, 1.9 mmol) in toluene (5 mL) and the resulting solution was heated in an oil bath at 85° C. for 2.5 hours. After cooling to room temperature, the reaction mixture was diluted with EtOAc (20 mL), washed with water (20 mL), 5% NaHCO$_3$ (20 mL), and brine (10 mL), dried over MgSO$_4$, filtered, and evaporated under vacuum to yield 7-methoxy-9a-methyl-1,2,9,9a-tetrahydro-3H-fluoren-3-one (430 mg) as a light brown solid.

$^1$H NMR (CDCl$_3$, 500 MHz) δ 1.31 (s, CH$_3$), 2.11 and 2.17 (two m, 1-CH$_2$), 2.51 and 2.65 (two m, 2-CH$_2$), 2.88 (s, 9-CH$_2$), 3.87 (s, OCH$_3$), 6.15 (s, H-4), 6.85–6.89 (m, H-6 and H-8), and 7.52 (d, H-5).

Step 5: 4-bromo-7-methoxy-9a-methyl-1,2,9,9a-tetrahydro-3H-fluoren-3-one

A mixture of 7-methoxy-9a-methyl-1,2,9,9a-tetrahydro-3H-fluoren-3-one (32 mg, 0.14 mmol) and NaHCO$_3$ (60 mg, 0.7 mmol) in CH$_2$Cl$_2$ (0.5 ml) was treated with bromine (0.008 mL, 0.154 mmol), and the resulting mixture was stirred at room temperature for 22 hours. The mixture was diluted with EtOAc (8 ml), washed with dilute aqueous Na$_2$S$_2$O$_3$ (4 mL) and brine (4 ml), dried over MgSO$_4$, filtered, and evaporated under vacuum to a yellow oil (43 mg). This material was purified by preparative layer chromatography on a 0.05×20×20 cm silica gel GF plate, developing twice with CH$_2$Cl$_2$, to afford 4-bromo-7-methoxy-9a-methyl-1,2,9,9a-tetrahydro-3H-fluoren-3-one (20 mg) as a gum. The product was contaminated with a trace of 4,6-dibromo-7-methoxy-9a-methyl-1,2,9,9a-tetrahydro-3H-fluoren-3-one.

$^1$H NMR (CDCl$_3$, 500 MHz) δ 1.33 (s, CH$_3$), 2.13 and 2.21 (two m, 1-CH$_2$), 2.77 and 2.84 (two m, 2-CH$_2$), 2.86 and 2.97 (two d, 9-CH$_2$), 3.89 (s, OCH$_3$), 6.88 (d, H-8), 6.93 (dd, H-6), and 8.49 (d, H-5).

Step 6: 4-bromo-7-hydroxy-9a-methyl-1,2,9,9a-tetrahydro-3H-fluoren-3-one

1M BBr$_3$ in CH$_2$Cl$_2$ (0.200 mL, 0.2 mmol) was added to an ice-cold solution of 4-bromo-7-methoxy-9a-methyl-1,2,9,9a-tetrahydro-3H-fluoren-3-one (10 mg, 0.033 mmol) in CH$_2$CL$_2$ (0.5 mL). The cooling bath was removed and the solution was stirred at room temperature for 30 minutes, then treated with more BBr$_3$ in CH$_2$CL$_2$ (0.5 mL, 0.5 mmol) and stirred at room temperature for an additional 60 minutes. The solution was diluted with EtOAc (10 mL), washed with water (10 mL), 1N HCl (2 mL), and brine (10 ml), dried over MgSO$_4$, filtered, and evaporated under vacuum to an oil. The crude product was purified by preparative layer chromatography on a 0.05×20×20 cm silica gel GF plate, developing with 5% CH$_3$OH in CH$_2$Cl$_2$, to afford 4-bromo-7-hydroxy-9a-methyl-1,2,9,9a-tetrahydro-3H-fluoren-3-one as a gum.

$^1$H NMR (DMSO-d$_6$, 500 MHz) δ 1.21 (s, CH$_3$), 2.02 and 2.12 (two m, 1-CH$_2$), 2.56 and 2.79 (two m, 2-CH$_2$), 2.78 and 2.88 (two d, 9-CH$_2$), 6.79–6.82 (m, H-6 and H-8), and 8.25 (m, H-5).

EXAMPLE 2

SYNTHESIS OF 9a-BUTYL-7-HYDROXY-4-METHYL-1,2,9,9a-TETRAHYDRO-3H-FLUOREN-3-ONE

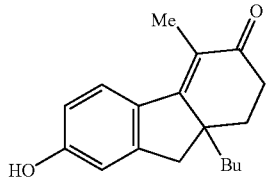

Step 1: 2-butyl-5-methoxy-1-indanone

Potassium hydroxide (0.44 g, 85% weight pure, 6.67 mmol) and 10% palladium on activated carbon (0.42 g) were added to a mixture of 5-methoxy-1-indanone (5.0 g, 30.8 mmol) and butyraldehyde (3.3 mL, 37 mmol) in ethanol (30 mL). The resulting mixture was stirred under an atmosphere of hydrogen at room temperature for 2 hours. The mixture was filtered and the filtrate evaporated under vacuum. The residue was partitioned between EtOAc (200 mL) and water (200 mL) containing 2N HCl (5 mL). The organic phase was washed with brine (100 mL), dried over $MgSO_4$, filtered, and evaporated under vacuum to afford crude 2-butyl-5-methoxy-1-indanone (7.0 g) as an oil.

$^1$H NMR ($CDCl_3$, 500 MHz) δ 0.93 (t, $CH_3$), 1.40 (m, $CH_2CH_2$), 1.47 and 1.96 (two m, $CH_2$), 2.66 (m, H-2), 2.78 and 3.28 (two dd, 3-$CH_2$), 3.90 (s, $OCH_3$), 6.88–6.94 (m, H-4 and H-6), and 7.70 (d, H-7).

Step 2: 2-butyl-5-methoxy-2-(3-oxo-pentyl)-1-indanone

A solution of crude 2-butyl-5-methoxy-1-indanone (218 mg, 1 mmol) in tetrahydrofuran (THF, 2 mL) was treated with 1,8-diazabicyclo[5.4.0]undec-7-ene (DBU, 0.030 mL, 0.2 mmol) and ethyl vinyl ketone (EVK, 0.200 mL, 2 mmol). The resulting solution was stirred under a nitrogen atmosphere at room temperature for 16 hours, followed by heating in an oil bath at 60° C. for 24 hours. Evaporation of the solvent under vacuum left a residue that was shown by NMR to be approximately a 1:1 mixture of starting material and product. The residue was purified by preparative layer chromatography on three 0.1×20×20 cm silica gel GF plates using 5% EtOAc in $CH_2Cl_2$ as developing solvent. The product band was eluted with EtOAc to provide 2-butyl-5-methoxy-2-(3-oxo-pentyl)-1-indanone (84 mg) as an oil.

$^1$H NMR ($CDCl_3$, 500 MHz) δ 0.82 (t, $CH_2CH_2CH_2CH_3$), 0.98 (t, $COCH_2CH_3$), 1.05 and 1.16 (two m, $CH_2CH_2CH_2CH_3$), 1.23 (m, $CH_2CH_2CH_2CH_3$), 1.57 (m, $CH_2CH_2CH_2CH_3$), 1.87 (m, $CH_2CH_2CO$), 2.28 (t, $CH_2CH_2CO$), 2.33 (m, $COCH_2CH_3$), 2.85 and 3.00 (two d, 3-$CH_2$), 3.87 (s, $OCH_3$), 6.86 (d, H-4), 6.89 (dd, H-6), and 7.65 (d, H-7).

Step 3: 9a-butyl-7-methoxy-4-methyl-1,2,9,9a-tetrahydro-3H-fluoren-3-one

A solution of 2-butyl-5-methoxy-2-(3-oxo-pentyl)-1-indanone (84 mg, 0.28 mmol) in acetic acid (0.5 mL) and 6N HCl (0.5 mL) was stirred and heated in an oil bath at 100° C. for 21 hours. After cooling to room temperature, the reaction mixture was partitioned between EtOAc (20 mL) and water (20 mL). The organic phase was washed with water (10 mL), 5% $NaHCO_3$ (20 mL), and brine (10 mL), dried over $MgSO_4$, filtered, and evaporated under vacuum to afford 9a-butyl-7-methoxy-4-methyl-1,2,9,9a-tetrahydro-3H-fluoren-3-one (76 mg) as a gum.

$^1$H NMR ($CDCl_3$, 500 MHz) δ 0.86 (t, $CH_3$), 1.16–1.33 (m, $CH_2CH_2$), 1.39 and 1.61 (two m, $CH_2$), 1.99 and 2.24 (two m, 1-$CH_2$), 2.48 and 2.59 (two m, 2-$CH_2$), 2.73 and 2.98 (two d, 9-$CH_2$), 3.88 (s, $OCH_3$), 6.85–6.89 (m, H-6 and H-8), and 7.67 (d, H-5).

Step 4: 9a-butyl-7-hydroxy-4-methyl-1,2,9,9a-tetrahydro-3H-fluoren-3-one

A solution of 9a-butyl-7-methoxy-4-methyl-1,2,9,9a-tetrahydro-3H-fluoren-3-one (76 mg, 0.267 mmol) in anhydrous $CH_2Cl_2$ (2 mL) was placed under a nitrogen atmosphere, cooled in an ice bath, and stirred while 1M $BBr_3$ in $CH_2Cl_2$ (0.80 mL, 0.80 mmol) was added by syringe. The cooling bath was removed and the mixture was stirred at room temperature for 2 hours. The mixture was partitioned between EtOAc (20 mL) and water (20 mL) containing 2N HCl (2 mL). The organic phase was washed with brine (10 mL), dried over $MgSO_4$, filtered, and evaporated under vacuum to an oil. This material was purified by preparative layer chromatography on a 0.1×20×20 cm silica gel GF plate using 5% MeOH in $CH_2Cl_2$ as the developing solvent. The product band was eluted with 10% MeOH in $CH_2Cl_2$ and the eluant evaporated under vacuum to give an oil which was lyophilized from benzene to afford 9a-butyl-7-hydroxy-4-methyl-1,2,9,9a-tetrahydro-3H-fluoren-3-one as an amorphous solid.

$^1$H NMR (DMSO-$d_6$, 500 MHz) δ 0.77 (t, $CH_3$), 1.05–1.28 (m, $CH_2CH_2$ and CHaHb), 1.49 (m, CHaHb), 1.89 and 2.11 (two m, 1-$CH_2$), 1.91 (s, 4-$CH_3$), 2.27 and 2.46 (two m, 2-$CH_2$), 2.61 and 2.87 (two d, 9-$CH_2$), 6.72 (dd, H-6), 6.75 (d, H-8), and 7.53 (d, H-5).

EXAMPLE 3

SYNTHESIS OF (3E)-9a-BUTYL-7-HYDROXY-4-METHYL-1,2,9,9a-TETRAHYDRO-3H-FLUOREN-3-ONE OXIME

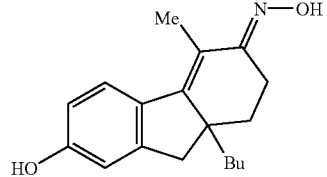

A solution of 9a-butyl-7-hydroxy-4-methyl-1,2,9,9a-tetrahydro-3H-fluoren-3-one (60 mg, 0.22 mmol) and hydroxyl amine hydrochloride (77 mg, 1.11 mmol) in anhydrous pyridine (0.5 mL) was stirred under a nitrogen atmosphere at room temperature for 4.3 hours and then heated in an oil bath at 60° C. for 30 minutes. The reaction mixture was evaporated under vacuum to an oil which was taken up in EtOAc (10 mL), washed with 1N HCl (2×6 ml), water (6 mL) and brine (6 ml), dried over $MgSO_4$, filtered, and evaporated under vacuum. The residue was lyophilized from benzene (3 mL) to afford (3E)-9a-butyl-7-hydroxy-4-methyl-1,2,9,9a-tetrahydro-3H-fluoren-3-one oxime as an amorphous solid.

$^1$H NMR (DMSO-$d_6$, 500 MHz) δ 0.76 (t, $CH_3$), 1.03–1.32 (m, $CH_2CH_2CH_2$), 1.47 and 1.99 (two m, 1-$CH_2$), 2.03 (s, 4-$CH_3$), 2.19 and 2.75 (two m, 2-$CH_2$), 2.52 and 2.79 (two d, 9-$CH_2$), 6.63 (dd, H-6), 6.67 (br s, H-8), 7.39 (d, H-5), 9.52 (br s, OH), and 10.75 (s, OH).

EXAMPLE 4

SYNTHESIS OF 9a-[(1E)-1-BUTENYL]-7-HYDROXY-4-METHYL-1,2,9,9a-TETRAHYDRO-3H-FLUOREN-3-ONE

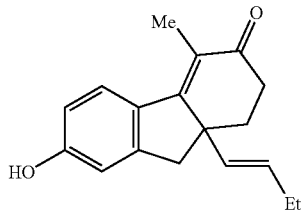

Step 1: 2-butylidene-5-methoxy-1-indanone

A solution of diisopropylamine (0.227 mL, 1.62 mmol) in anhydrous tetrahydrofuran (THF, 15 mL) was placed under a nitrogen atmosphere, cooled in an ice bath, and stirred while a 2.0M solution of butyllithium in pentane (0.771 mL, 1.54 mmol) was added dropwise over 2 minutes. The solution was stirred at room temperature for 15 minutes, then cooled in a dry ice-acetone bath and treated dropwise over 3 minutes with a solution of 5-methoxy-1-indanone (250 mg, 1.54 mmol) in THF (2 mL). After stirring at −78° C. for 20 minutes, the reaction mixture was treated with butyraldehyde (0.167 mL, 1.85 mmol). After stirring an additional 26 minutes at −78° C., the reaction mixture was removed from the cooling bath and stirred at room temperature for 90 hours. The reaction mixture was treated with saturated aqueous $NH_4Cl$ solution (10 mL) and extracted with EtOAc (15 mL). The organic phase was washed with brine (25 ml), dried over $MgSO_4$, filtered, and evaporated under vacuum to an oil (353 mg). The crude product was purified by silica gel chromatography on a Biotage FLASH 12M column (1.2×15 cm), eluting with 7:1 hexanes-EtOAc, to afford 2-butylidene-5-methoxy-1-indanone (205 mg) as a solid.

$^1$H NMR ($CDCl_3$, 400 MHz) δ 1.00 (t, $CH_2CH_2CH_3$), 1.59 (m, $CH_2CH_2CH_3$), 2.30 (m, $CH_2CH_2CH_3$), 3.63 (br s, 3-$CH_2$), 3.91 (s, $OCH_3$), 6.82 (m, =CH), 6.92–6.96 (m, H-4 and H-6), and 7.82 (d, H-7).

Step 2: 2-[(1E)-1-butenyl]-5-methoxy-2-(3-oxo-pentyl)-1-indanone

A solution of 2-butylidene-5-methoxy-1-indanone (202 mg, 0.934 mmol) in anhydrous tetrahydrofuran (THF, 3.7 mL) was placed under a nitrogen atmosphere and treated with ethyl vinyl ketone (EVK, 0.187 mL, 1.87 mmol) followed by 1,8-diazabicyclo[5.4.0]undec-7-ene (DBU, 0.028 mL, 0.187 mmol). The resulting solution was stirred and heated in an oil bath at 60° C. for 5 hours. After cooling to room temperature, the mixture was diluted with EtOAc (15 mL), washed with 0.2N HCl (10 mL), water (10 mL) and brine (10 mL), dried over $MgSO_4$, filtered, and evaporated under vacuum to an oil (270 mg). Proton NMR of this material showed a 1:1 mixture of product and starting material. The reaction was rerun using the mixture (270 mg), EVK (0.187 mL), DBU (0.028 mL), and THF (1.8 mL) with heating at 60° C. for 27 hours. Workup as above gave an oil (448 mg) which contained no starting material. The crude product was purified by silica gel chromatography on a Biotage FLASH 12M column (1.2×15 cm), eluting with 4:1 hexanes-EtOAc, to afford 2-[(1E)-1-butenyl]-5-methoxy-2-(3-oxopentyl)-1-indanone (199 mg) as an oil. The product contained a minor amount of the (Z)-butenyl isomer as evidenced by proton NMR.

$^1$H NMR ($CDCl_3$, 400 MHz) δ 0.96 (t, $CH_3$), 1.03 (t, $CH_3$), 1.88–2.08 (m, two $CH_2$), 2.29–2.52 (m, two $CH_2$), 2.99 and 3.21 (two d, 3-$CH_2$), 3.90 (s, $OCH_3$), 5.54 (m, CH=CHCH$_2$), 5.60 (td, CH=CHCH$_2$), 6.88 (d, H-4), 6.92 (dd, H-6), and 7.69 (d, H-7).

Step 3: 9a-[(1E)-1-butenyl]-7-methoxy-4-methyl-1,2,9,9a-tetrahydro-3H-fluoren-3-one A solution of 2-[(1E)-1-butenyl]-5-methoxy-2-(3-oxopentyl)-1-indanone (199 mg, 0.663 mmol) in methanol (5 mL) was treated with 2N aqueous NaOH (1.6 mL) and the resulting mixture was stirred and heated in an oil bath at 85° C. for 7 hours. After cooling to room temperature, the brown solution was partitioned between EtOAc (20 mL) and 0.4N HCl (10 mL). The organic phase was separated, washed with brine (15 ml), dried over $MgSO_4$, filtered, and evaporated under vacuum to a brown oil (208 mg). The crude product was purified by silica gel chromatography on a Biotage FLASH 12S column (1.2×7.5 cm), eluting with 5:1 hexanes:EtOAc, to afford 9a-[(1E)-1-butenyl]-7-methoxy-4-methyl-1,2,9,9a-tetrahydro-3H-fluoren-3-one (67 mg) as an oil.

$^1$H NMR ($CDCl_3$, 400 MHz) δ 0.87 (t, $CH_3$), 1.92 (m, =CHCH$_2$CH$_3$), 2.08–2.19 (m, 1-$CH_2$), 2.14 (s, 4-$CH_3$), 2.43 and 2.57 (two m, 2-$CH_2$), 2.95 (m, 9-$CH_2$), 3.86 (s, $OCH_3$), 5.29 (td, CH=CHCH$_2$), 5.42 (td, CH=CHCH$_2$), 6.82–6.88 (m, H-6 and H-8), and 7.67 (d, H-5).

Step 4: 9a-[(1E)-1-butenyl]-7-hydroxy-4-methyl-1,2,9,9a-tetrahydro-3H-fluoren-3-one A mixture of 9a-[(1E)-1-butenyl]-7-methoxy-4-methyl-1,2,9,9a-tetrahydro-3H-fluoren-3-one (31.7 mg, 0.112 mmol) and pyridine hydrochloride (384 mg, 3.32 mmol) was placed under a nitrogen atmosphere and heated in an oil bath at 190° C. for 65 minutes. After cooling to room temperature, the reaction mixture was partitioned between water (4 ml) and EtOAc (10 mL). The organic phase was recovered, washed with brine (5 mL), dried over $MgSO_4$, filtered, and evaporated under vacuum to an oil (30 mg). The crude product was purified by silica gel chromatography on a Biotage FLASH 12S column (1.2×7.5 cm), eluting with 3:1 hexanes-EtOAc. The product containing fractions were concentrated under vacuum and the residue lyophilized from benzene to provide 9a-[(1E)-1-butenyl]-7-hydroxy-4-methyl-1,2,9,9a-tetrahydro-3H-fluoren-3-one as a yellow, amorphous solid.

$^1$H NMR (9:1 $CDCl_3$-$CD_3CN$, 500 MHz) δ 0.85 (t, $CH_3$), 1.90 (m, =CHCH$_2$CH$_3$), 2.04–2.16 (m, 1-$CH_2$), 2.12 (s, 4-$CH_3$), 2.42 and 2.55 (two m, 2-$CH_2$), 2.91 (m, 9-$CH_2$), 5.27 (td, CH=CHCH$_2$), 5.40 (td, CH=CHCH$_2$), 6.68 (br s, OH), 6.77–6.82 (m, H-6 and H-8), and 7.61 (d, H-5).

EXAMPLE 5

SYNTHESIS OF 4-BROMO-9a-BUTYL-7-HYDROXY-1,2,9,9a-TETRAHYDRO-3H-FLUOREN-3-ONE

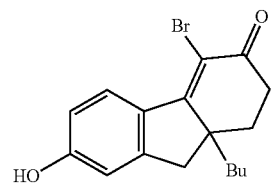

Step 1: 2-butyl-5-methoxy-1-indanone

A mixture of 5-methoxy-1-indanone (25.0 g, 154 mmol), 85% KOH (2.03 g, 30.8 mmol), 10% palladium on activated carbon (2 g), and ethanol (150 mL) was placed under a hydrogen atmosphere and stirred while butyraldehyde (16.7 mL, 185 mmol) was added over 2 minutes. The mixture warmed during the addition. The resulting mixture was hydrogenated at room temperature for 3 hours, then filtered to remove the catalyst. The filtrate was acidified with 2N HCl (15.4 mL, 30.8 mmol) and evaporated under vacuum. The residue was partitioned between EtOAc (500 mL) and water (500 mL). The organic phase was washed with water (500 mL) and brine (100 mL), dried over $MgSO_4$, filtered, and evaporated under vacuum to an oil (33.5 g). The crude product was purified by column chromatography on EM silica gel 60 (230–400 mesh, 670 g), eluting first with $CH_2Cl_2$ and then with 5% EtOAc in $CH_2Cl_2$, to afford 2-butyl-5-methoxy-1-indanone (17.9 g) as an oil.

Step 2: 2-butyl-5-methoxy-2-(3-oxo-butyl)-1-indanone

A mixture of 2-butyl-5-methoxy-1-indanone (17.9 g, 82 mmol), methyl vinyl ketone (MVK, 8.5 mL, 102 mmol), and 1,8-diazabicylco[5.4.0]undec-7-ene (2.5 mL, 16.4 mmol) in anhydrous tetrahydrofuran (45 mL) was stirred under a nitrogen atmosphere at room temperature for 42 hours. Additional MVK (1.7 mL, 20.5 mmol) was added and the mixture was stirred and heated in an oil bath at 60° C. for 55 minutes. The resulting solution of crude 2-butyl-5-methoxy-2-(3-oxo-butyl)-1-indanone was used in the next step.

Step 3: 9a-butyl-7-methoxy-1,2,9,9a-tetrahydro-3H-fluoren-3-one

The solution from step 2 was treated with pyrrolidine (6.9 mL, 82 mmol) and acetic acid (4.7 mL, 82 mmol), placed under a nitrogen atmosphere, and stirred with heating in a 60° C. bath for 22 hours. After cooling to room temperature, the reaction mixture was partitioned between EtOAc (500 mL) and water (500 mL). The EtOAc phase was washed with 0.8N HCl (500 mL), water (500 mL), 5% $NaHCO_3$ (500 mL), and brine (200 mL), dried with $MgSO_4$, filtered, and evaporated under vacuum to a brown oil (22.8 g). This material was purified by column chromatography on EM silica gel 60 (230–400 mesh, 684 g), using 5% EtOAc in $CH_2Cl_2$ as eluting solvent, to afford 9a-butyl-7-methoxy-1,2,9,9a-tetrahydro-3H-fluoren-3-one (11.2 g) as a solid.

$^1$H NMR ($CDCl_3$, 500 MHz) δ 0.87 (t, $CH_3$), 1.17–1.35 (m, $CH_2CH_2$), 1.47 and 1.65 (two m, $CH_2$), 1.99 and 2.29 (two m, 1-$CH_2$), 2.47 and 2.58 (two m, 2-$CH_2$), 2.72 and 3.03 (two d, 9-$CH_2$), 3.87 (s, $OCH_3$), 6.16 (s, H-4), 6.83–6.89 (m, H-6 and H-8), and 7.51 (d, H-5).

Step 4: 4-bromo-9a-butyl-7-methoxy-1,2,9,9a-tetrahydro-3H-fluoren-3-one

A solution of 9a-butyl-7-methoxy-1,2,9,9a-tetrahydro-3H-fluoren-3-one (11.2 g, 41.4 mmol) in $CCl_4$ (80 mL) was treated with solid $NaHCO_3$ (17.4 g, 207 mmol). The mixture was cooled in an ice bath and rapidly swirled by hand while bromine (2.13 mL, 41.4 mmol) was added over 6 minutes. After swirling a total of 30 minutes at 0° C., the mixture was diluted with $CH_2Cl_2$ (100 mL) and water (200 mL), treated with a small scoop of $Na_2SO_3$, and shaken. The aqueous phase was re-extracted with more $CH_2Cl_2$ (50 mL). The combined $CH_2Cl_2$ extracts were dried over $MgSO_4$, filtered, and evaporated under vacuum. The residue in $CH_2Cl_2$ (30 mL) was added to a plug of EM silica gel 60 (230–400 mesh, 50 g) which was eluted with $CH_2Cl_2$ to give the product (13.7 g) as a solid. This material was dissolved in hot 2-propanol (350 mL) and the solution concentrated under vacuum to a suspension (ca. 100 mL volume). The solid was collected, washed with 2-propanol (20 mL), and dried under a nitrogen stream to afford 4-bromo-9a-butyl-7-methoxy-1,2,9,9a-tetrahydro-3H-fluoren-3-one (10.4 g).

$^1$H NMR ($CDCl_3$, 500 MHz) δ 0.86 (t, $CH_3$), 1.14–1.32 (m, $CH_2CH_2$), 1.48 and 1.67 (two m, $CH_2$), 2.08 and 2.27 (two m, 1-$CH_2$), 2.68–2.80 (m, 2-$CH_2$), 2.80 and 3.03 (two d, 9-$CH_2$), 3.89 (s, $OCH_3$), 6.86 (d, H-8), 6.92 (dd, H-6), and 8.51 (d, H-5).

Step 5: 4-bromo-9a-butyl-7-hydroxy-1,2,9,9a-tetrahydro-3H-fluoren-3-one

A solution of 4-bromo-9a-butyl-7-methoxy-1,2,9,9a-tetrahydro-3H-fluoren-3-one (1.00 g, 2.75 mmol) in anhydrous $CH_2Cl_2$ (27.5 mL) was cooled in a dry ice-acetone bath and stirred under a nitrogen atmosphere while 1M $BBr_3$ in $CH_2Cl_2$ (8.26 mL, 8.26 mmol) was added dropwise over 14 minutes. The cooling bath was removed and the solution was stirred at room temperature for 3 hours, during which time it darkened considerably. The mixture was diluted with EtOAc (150 mL) and shaken with water (150 mL) containing 2N HCl (10 mL). The organic phase was washed with water (150 mL) and brine (150 mL), dried with $MgSO_4$, filtered, and evaporated under vacuum to a dark green solid (1.1 g). The solid was dissolved in 10% EtOAc/$CH_2Cl_2$ (10 mL) and added to a small column of EM silica gel 60 (230–400 mesh, 12 g). The column was eluted with 10% EtOAc/$CH_2Cl_2$. The first 100 mL of eluant was evaporated under vacuum to a green solid (1.0 g). This material was further purified by column chromatography on EM silica gel 60 (230–400 mesh, 30 g) using 5% EtOAc/$CH_2Cl_2$ as eluting solvent. The product containing fractions were evaporated under vacuum to provide a solid (730 mg). This material was treated with benzene (7 mL) and the mixture heated to reflux. The suspension was sonicated while cooling to room temperature. The solid was collected, rinsed with benzene (5 mL), and dried under a nitrogen stream to afford 4-bromo-9a-butyl-7-hydroxy-1,2,9,9a-tetrahydro-3H-fluoren-3-one as a pale green powder.

$^1$H NMR (DMSO-$d_6$, 500 MHz) δ 0.77 (t, $CH_3$), 1.04–1.25 (m, $CH_2CH_2$), 1.33 and 1.58 (two m, $CH_2$), 2.01 and 2.12 (two m, 1-$CH_2$), 2.52 and 2.70 (two m, 2-$CH_2$), 2.73 and 2.94 (two d, 9-$CH_2$), 6.78–6.81 (m, H-6 and H-8), 8.26 (m, H-5), and 10.35 (s, OH).

EXAMPLE 6

SYNTHESIS OF 4-BROMO-9a-BUTYL-3-METHYENE-2,3,9,9a-TETRAHYDRO-1H-FLUOREN-7-OL

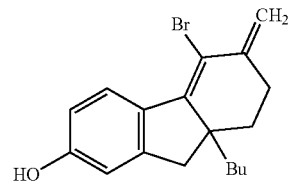

A suspension of methyltriphenylphosphonium bromide (373 mg, 1.04 mmol) in anhydrous tetrahydrofuran (2 mL) was cooled in an ice bath and stirred under a nitrogen atmosphere while 2.5 N nBuLi in hexane (0.36 mL, 0.90 mmol) was added by syringe. The mixture was stirred at 0° C. for 10 minutes to complete formation of the methylenetriphenylphosporane reagent. A solution of 4-bromo-9a-butyl-7-hydroxy-1,2,9,9a-tetrahydro-fluoren-3-one (50 mg, 0.15 mmol) in tetrahydrofuran (1 mL) was added to the reaction mixture and the ice bath was removed. The resulting mixture was stirred at room temperature for 3.2 hours, then at 50° C. for 1.5 hour, and finally at room temperature for an additional 17 hours. The mixture was partitioned between saturated aqueous $NH_4Cl$ (5 mL) and EtOAc (9 mL). The organic phase was acidified with 2N HCl (0.2 mL), washed with brine (4 mL), dried over $MgSO_4$, filtered, and evaporated under vacuum to an oil (90. mg). The crude product was purified by preparative layer chromatography on a 0.1×20×20 cm silica gel GF plate using 3:1 hexanes-EtOAc as developing solvent. The UV visible band at $R_f$ 0.50–0.63 was eluted with EtOAc. The eluant was concentrated under vacuum to a residue which was lyophilized from benzene to afford 4-bromo-9a-butyl-3-methylene-2,3,9,9a-tetrahydro-1H-fluoren-7-ol.

$^1$H NMR (CDCl$_3$, 500 MHz) δ 0.85 (t, CH$_3$), 1.1–1.3 (m, CH$_2$CH$_2$), 1.36 and 1.55 (two m, CH$_2$), 1.70 and 2.06 (two m, 1-CH$_2$), 2.67 and 2.76 (two m, 2-CH$_2$), 2.67 and 2.88 (two d, 9-CH$_2$), 5.02 (s, OH), 5.07 and 5.56 (two m, =CH$_2$), 6.75 (m, H-6 and H-8), and 8.25 (d, H-5).

EXAMPLE 7

SYNTHESIS OF 9a-BUTYL-4-CYANO-7-HYDROXY-1,2,9,9a-TETRAHYDRO-3H-FLUOREN-3-ONE

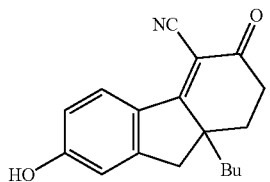

Step 1: 9a-butyl-4-cyano-7-methoxy-1,2,9,9a-tetrahydro-3H-fluoren-3-one

A solution of 4-bromo-9a-butyl-7-methoxy-1,2,9,9a-tetrahydro-3H-fluoren-3-one (50 mg, 0.138 mmol) in anhydrous 1-methyl-2-pyrrolidinone (0.276 mL) was treated with copper(I) cyanide (25 mg, 0.275 mmol). The resulting mixture was stirred under a nitrogen atmosphere and heated in an oil bath at 160° C. for 40 minutes. The mixture was partitioned between EtOAc (20 mL) and water (20 ml). The organic phase was washed with water (2×20 mL) and brine (10 mL), dried over MgSO$_4$, filtered, and evaporated under vacuum. The residue was purified by preparative layer chromatography on a 0.1×20×20 cm silica gel GF plate, developing with 5% EtOAc in CH$_2$Cl$_2$, to afford 9a-butyl-4-cyano-7-methoxy-1,2,9,9a-tetrahydro-3H-fluoren-3-one (33 mg) as an oil.

$^1$H NMR (CDCl$_3$, 500 MHz) δ 0.87 (t, CH$_3$), 1.13–1.35 (m, CH$_2$CH$_2$), 1.44 and 1.66 (two m, CH$_2$), 2.02 and 2.32 (two m, 1-CH$_2$), 2.61 (m, 2-CH$_2$), 2.78 and 3.09 (two d, 9-CH$_2$), 3.92 (s, OCH$_3$), 6.91 (br s, H-8), 6.97 (dd, H-6), and 8.33 (d, H-5).

Step 2: 9a-butyl-4-cyano-7-hydroxy-1,2,9,9a-tetrahydro-3H-fluoren-3-one

A mixture of 9a-butyl-4-cyano-7-methoxy-1,2,9,9a-tetrahydro-3H-fluoren-3-one (17 mg) and pyridine hydrochloride (2 g) was placed under a nitrogen atmosphere and heated in an oil bath at 190–195° C. for 1 hour. After cooling to room temperature, the mixture was partitioned between EtOAc (20 ml) and water (30 mL). The organic portion was washed with brine (10 mL), dried over MgSO$_4$, filtered, and evaporated under vacuum to an oil (16 mg). The crude product was purified by preparative layer chromatography on a 0.05×20×20 cm silica gel GF plate using 5% CH$_3$OH n CH$_2$Cl$_2$ as the developing solvent. The UV visible product band was eluted with 10% CH$_3$OH in CH$_2$Cl$_2$, the solvent evaporated under vacuum, and the residue lyophilized from benzene-methanol to afford 9a-butyl-4-cyano-7-hydroxy-1,2,9,9a-tetrahydro-3H-fluoren-3-one as an amorphous solid.

$^1$H NMR (DMSO-d$_6$, 500 MHz) δ 0.78 (t, CH$_3$), 1.01–1.33 (m, CH$_2$CH$_2$ and CHaHb), 1.61 (m, CHaHb), 1.99 and 2.15 (two m, 1-CH$_2$), 2.40 and 2.58 (two m, 2-CH$_2$), 2.71 and 3.01 (two d, 9-CH$_2$), 6.87 (s, H-8), 6.89 (d, H-6), and 8.04 (d, H-5).

IR (KBr) 2223, 1648, 1611, 1558, 1467, 1356, 1316, 1296, 1278, 1107, 1066 cm$^{-1}$.

EXAMPLE 8

SYNTHESIS OF 4-BENZYL-9a-BUTYL-7-HYDROXY-1,2,9,9a-TETRAHYDRO-3H-FLUOREN-3-ONE

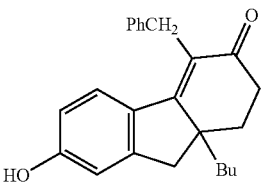

Step 1: 4-benzyl-9a-butyl-7-methoxy-1,2,9,9a-tetrahydro-3H-fluoren-3-one

A mixture of 4-bromo-9a-butyl-7-methoxy-1,2,9,9a-tetrahydro-3H-fluoren-3-one (29.6 mg, 0.0847 mmol), 5-benzyl-1-aza-5-stanna-bicyclo[3.3.3]undecane (38.5 mg, 85% weight pure, 0.0935 mmol), and Pd(PPh$_3$)$_4$ (9.8 mg, 0.00848 mmol) in anhydrous toluene (1.3 mL) was degassed, placed under a nitrogen atmosphere, stirred, and heated in an oil bath at 100° C. After heating 4 hours, the cloudy, dark brown reaction mixture was cooled in an ice bath and filtered through a pad of celite. The filtrate was evaporated under vacuum to an orange gum (57 mg). The crude product was purified by preparative layer chromatography on a 0.1×20×20 cm silica gel GF plate, using 9:1 hexanes-EtOAc as developing solvent. The major UV visible band at $R_f$ 0.18–0.26 was removed and eluted with EtOAc to afford 4-benzyl-9a-butyl-7-methoxy-1,2,9,9a-tetrahydro-3H-fluoren-3-one (29 mg) as a pale yellow gum.

$^1$H NMR (CDCl$_3$, 500 MHz) δ 0.87 (t, CH$_3$), 1.19–1.36 (m, CH$_2$CH$_2$), 1.51 and 1.72 (two m, CH$_2$), 2.07 and 2.29 (two m, 1-CH$_2$), 2.52 and 2.64 (two m, 2-CH$_2$), 2.77 and 3.01 (two d, 9-CH$_2$), 3.76 and 4.16 (two d, CH$_2$Ph), 3.82 (s, OCH$_3$), 6.71 (dd, H-6), 6.84 (d, H-8), 7.13–7.27 (m, phenyl-H), and 7.42 (d, H-5).

Step 2: 4-benzyl-9a-butyl-7-hydroxy-1,2,9,9a-tetrahydro-3H-fluoren-3-one

A solution of 4-benzyl-9a-butyl-7-methoxy-1,2,9,9a-tetrahydrofluoren-3-one (25.9 mg, 0.718 mmol) in anhydrous CH$_2$Cl$_2$ (1.2 mL) was cooled in a dry ice-acetone bath and stirred under a nitrogen atmosphere while 1M BBr$_3$ in CH$_2$Cl$_2$ (0.215 mL, 0.215 mmol) was added dropwise by syringe. The cooling bath was removed and the mixture was stirred at room temperature for 3.5 hours, after which it was diluted with EtOAc (8 mL), water (3 mL) and 2N HCl (1 mL) and shaken vigorously. The organic phase was separated, washed with water (3 mL), 1M pH 3 phosphate (3 mL) and brine (3 mL), dried over MgSO$_4$, filtered and evaporated under vacuum to a solid (25 mg). The crude product was purified by preparative layer chromatography on a 0.1×20×20 cm silica gel GF plate, using 5% MeOH in CH$_2$Cl$_2$ as developing solvent. The major UV visible band at $R_f$ 0.40–0.53 gave 4-benzyl-9a-butyl-7-hydroxy-1,2,9,9a-tetrahydro-3H-fluoren-3-one as a yellow solid.

$^1$H NMR (CDCl$_3$, 500 MHz) δ 0.87 (t, CH$_3$), 1.18–1.36 (m, CH$_2$CH$_2$), 1.51 and 1.71 (two m, CH$_2$), 2.06 and 2.28 (two m, 1-CH$_2$), 2.52 and 2.65 (two m, 2-CH$_2$), 2.74 and 2.98 (two d, 9-CH$_2$), 3.75 and 4.15 (two d, CH$_2$Ph), 6.62 (dd, H-6), 6.78 (d, H-8), 7.13–7.27 (m, phenyl-H), and 7.36 (d, H-5).

IR (neat film) 3138, 2929, 1625, 1572, 1468, 1359, 1329, 1299, 1272, 1184, 1104, 1077, 724, and 695 cm$^{-1}$.

EXAMPLE 9

SYNTHESIS OF 9a-BUTYL-7-HYDROXY-4-(2-THIENY)-1,2,9,9a-TETRAHYDRO-3H-FLUOREN-3-ONE

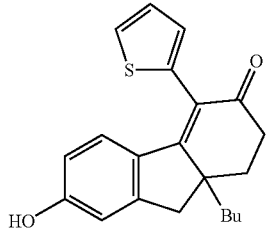

Step 1: 9a butyl-7-methoxy-4-(2-thienyl)-1,2,9,9a-tetrahydro-3H-fluoren-3-ene

A mixture of 4-bromo-9a-butyl-7-methoxy-1,2,9,9a-tetrahydro-3H-fluoren-3-one (30 mg, 0.086 mmol), 2-(tributylstannyl)-thiophene (0.055 mL, 0.172 mmol), tris (dibenzylideneacetone)dipalladium(0) (Pd$_2$(dba)$_3$, 16 mg, 0.0172 mmol), and anhydrous toluene (0.5 mL) was placed under a nitrogen atmosphere, stirred, and heated in an oil bath at 100–110° C. Three additional Pd$_2$(dba)$_3$ portions (20–30 mg each) were added at 7, 8, and 23 hours. An aliquot of the reaction that was removed after heating for 23.5 hours showed approximately a 1:1 mixture of starting material and product. The mixture was treated with bis (triphenylphosphine)-palladium(II) chloride (30 mg) and heating was continued for 55 minutes to complete the conversion to product. After cooling to room temperature, the reaction mixture was purified by preparative layer chromatography on a 0.1×20×20 cm silica gel GF plate, developing with CH$_2$Cl$_2$, to afford 9a butyl-7-methoxy-4-(2-thienyl)-1,2,9,9a-tetrahydro-3H-fluoren-3-ene (16.5 mg) as an oil.

$^1$H NMR (CDCl$_3$, 500 MHz) δ 0.89 (t, CH$_3$), 1.23–1.37 (m, CH$_2$CH$_2$), 1.53 and 1.75 (two m, CH$_2$), 2.14 and 2.33 (two m, 1-CH$_2$), 2.62 and 2.71 (two m, 2-CH$_2$), 2.80 and 3.04 (two d, 9-CH$_2$), 3.81 (s, OCH$_3$), 6.51 (d, H-5), 6.58 (dd, H-6), 6.81 (d, H-8), 6.87 (dd, thienyl H-3), 7.13 (dd, thienyl H-4), and 7.43 (dd, thienyl H-5).

Step 2: 9a butyl-7-hydroxy-4-(2-thienyl)-1,2,9,9a-tetrahydro-3H-fluoren-3-ene

A solution of 9a butyl-7-methoxy-4-(2-thienyl)-1,2,9,9a-tetrahydro-3H-fluoren-3-ene (16.5 mg, 0.048 mmol) in anhydrous CH$_2$Cl$_2$ was placed under nitrogen, cooled in an ice bath, stirred, and treated with 1M BBr$_3$ in CH$_2$Cl$_2$ (0.145 mL, 0.145 mmol). The cooling bath was removed and the solution was stirred at room temperature. The demethylation was slow. After 50 minutes, more BBr$_3$ in CH$_2$Cl$_2$ (1.5 mL) was added and the solution was stirred at room temperature for an additional 50 minutes. The mixture was diluted with EtOAc (10 mL) and washed with water (8 mL) containing 2N HCl (2 mL). The organic phase was washed with brine (5 mL), dried over MgSO$_4$, filtered, and evaporated under vacuum. The residue was purified by preparative layer chromatography on two successive 0.025×20×20 cm silica gel GF plates, developing the first with 5% CH$_3$OH in CH$_2$Cl$_2$ and the second with 2% CH$_3$OH in CH$_2$Cl$_2$. The product band was eluted with 10% CH$_3$OH in CH$_2$Cl$_2$, the eluant concentrated under vacuum, and the residue lyophilized from benzene to afford 9a butyl-7-hydroxy-4-(2-thienyl)-1,2,9,9a-tetrahydro-3H-fluoren-3-ene as yellow, amorphous solid.

$^1$H NMR (DMSO-d$_6$, 500 MHz) δ 0.81 (t, CH$_3$), 1.11–1.31 (m, CH$_2$CH$_2$), 1.37 and 1.64 (two m, CH$_2$), 2.04 and 2.18 (two m, 1-CH$_2$), 2.39 and 2.58 (two m, 2-CH$_2$), 2.70 and 2.94 (two d, 9-CH$_2$), 6.25 (d, H-5), 6.41 (dd, H-6), 6.71 (d, H-8), 6.76 (dd, thienyl H-3), 7.09 (dd, thienyl H-4), and 7.59 (dd, thienyl H-5).

EXAMPLE 10

SYNTHESIS OF 9a-BUTYL-7-HYDROXY-4-{4-[2-(1-PIPERIDINYL)ETHOXY]-PHENYL}-1,2,9,9a-TETRAHYDRO-3H-FLUOREN-3-ONE

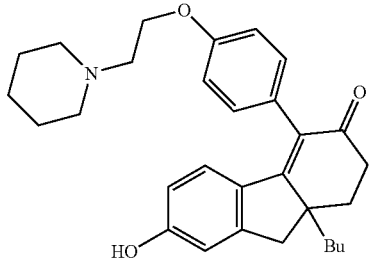

Step 1: 9a-butyl-7-methoxy-4-(4-methoxymethoxyphenyl)-1,2,9,9a-tetrahydro-3H-fluoren-3-one A mixture of 4-bromo-9a-butyl-7-methoxy-1,2,9,9a-tetrahydro-3H-fluoren-3-one (800 mg, 2.29 mmol), Pd(PPh$_3$)$_4$ (132 mg, 0.114 mmol), and tributyl-(4-methoxymethoxy-phenyl)-stannane (1.174 g, 2.75 mmol) in anhydrous toluene (11.5 mL) was placed under a nitrogen atmosphere and heated with stirring in an oil bath at 100° C. After 22 hours, the mixture was cooled to room temperature and evaporated under vacuum to a dark oil (2.208 g). This material was purified by chromatography on EM silica gel 60 (230–400 mesh, 115 mL dry), using 4:1 hexanes-EtOAc as eluting solvent, to afford 9a-butyl-7-methoxy-4-(4-methoxymethoxy-phenyl)-1,2,9,9a-tetrahydro-3H-fluoren-3-one (787 mg) as a yellow gum.

$^1$H NMR (CDCl$_3$, 500 MHz) δ 0.88 (t, CH$_3$), 1.21–1.38 (m, CH$_2$CH$_2$), 1.52 and 1.74 (two m, CH$_2$), 2.12 and 2.31 (two m, 1-CH$_2$), 2.57 and 2.68 (two m, 2-CH$_2$), 2.77 and 3.01 (two d, 9-CH$_2$), 3.52 (s, OCH$_3$), 3.78 (s, OCH$_3$), 5.22 (m, OCH$_2$O), 6.40 (d, H-5), 6.49 (dd, H-6), 6.78 (d, H-8), and 6.9–7.2 (br m, phenyl-H).

Step 2: 9a-butyl-4-(4-hydroxyphenyl)-7-methoxy-1,2,9,9a-tetrahydro-3H-fluoren-3-one A suspension of 9a-butyl-7-methoxy-4-(4-methoxymethoxy-phenyl)-1,2,9,9a-tetrahydro-3H-fluoren-3-one (813 mg, 2 mmol) in methanol (12 mL) was warmed in an oil bath at 60° C. and treated with aqueous 2N HCl (4 mL). The resulting mixture was stirred and heated at 60° C. for two hours, then cooled to room temperature and evaporated under vacuum to leave a yellow semi-solid. The residue was dissolved in EtOAc, washed with water and brine, dried over MgSO$_4$, filtered, evaporated under vacuum, and stripped with toluene to afford 9a-butyl-4-(4-hydroxyphenyl)-7-methoxy-1,2,9,9a-tetrahydro-3H-fluoren-3-one (787 mg, ca. 92% weight pure) as a yellow foam.

$^1$H NMR (CDCl$_3$, 500 MHz) δ 0.88 (t, CH$_3$), 1.21–1.38 (m, CH$_2$CH$_2$), 1.52 and 1.73 (two m, CH$_2$), 2.11 and 2.32 (two m, 1-CH$_2$), 2.58 and 2.69 (two m, 2-CH$_2$), 2.77 and 3.01 (two d, 9-CH$_2$), 3.78 (s, OCH$_3$), 6.40 (d, H-5), 6.49 (dd, H-6), 6.77 (d, H-8), and 6.8–7.1 (br m, phenyl-H).

Step 3: 9a-butyl-7-methoxy-4-{4-[2-(1-piperidinyl)ethoxy] phenyl}-1,2,9,9a-tetrahydro-3H-fluoren-3-one A mixture of crude 9a-butyl-4-(4-hydroxyphenyl)-7-methoxy-1,2,9,9a-tetrahydro-3H-fluoren-3-one (787 mg, approx. 2 mmol), cesium carbonate (1.564 g, 4.8 mmol), and 1-(2-chloroethyl)-piperidine monohydrochloride (442 mg, 2.4 mmol) in acetone (5 mL) was stirred and heated in an oil bath at 60° C. for 4 hours. After cooling to room temperature, the mixture was diluted with EtOAc and filtered to remove salts. The filtrate was washed with water and brine, dried over MgSO$_4$, filtered, and evaporated under vacuum to a yellow gum (0.95 g). The crude product was purified by chromatography on EM silica gel 60 (230–400 mesh, 50 mL dry) using 2% MeOH+1% Et$_3$N in EtOAc as eluting solvent. The product containing fractions were evaporated under vacuum and the residue stripped with toluene to provide 9a-butyl-7-methoxy-4-{4-[2-(1-piperidinyl)ethoxy]phenyl}-1,2,9,9a-tetrahydro-3H-fluoren-3-one (912 mg, 96% weight pure) as a pale yellow gum.

$^1$H NMR (CDCl$_3$, 500 MHz) δ 0.88 (t, CH$_3$), 1.21–1.38 (m, CH$_2$CH$_2$), 1.46 (m, 4-CH$_2$ of piperidine), 1.52 and 1.73 (two m, CH$_2$), 1.62 (m, 3-CH$_2$ and 5-CH$_2$ of piperidine), 2.11 and 2.31 (two m, 1-CH$_2$), 2.53 (m, 2-CH$_2$ and 6-CH$_2$ of piperidine), 2.57 and 2.68 (two m, 2-CH$_2$), 2.76 and 3.00 (two d, 9-CH$_2$), 2.80 (t, NCH$_2$CH$_2$O), 3.77 (s, OCH$_3$), 4.15 (t, NCH$_2$CH$_2$O), 6.38 (d, H-5), 6.49 (dd, H-6), 6.77 (d, H-8), and 6.8–7.2 (br m, phenyl-H).

Step 4: 9a-butyl-7-hydroxy-4-{4-[2-(1-piperidinyl)ethoxy]phenyl}-1,2,9,9a-tetrahydro-3H-fluoren-3-one and 9a-butyl-7-hydroxy-4-{4-[2-(1-piperidinyl)ethoxy]phenyl}-1,2,9,9a-tetrahydro-3H-fluoren-3-one hydrochloride An ice-cold solution of 9a-butyl-7-methoxy-4-{4-[2-(1-piperidinyl)-ethoxy]phenyl}-1,2,9,9a-tetrahydro-3H-fluoren-3-one (85 mg, 96% weight pure, 0.172 mmol) in anhydrous CH$_2$Cl$_2$ (1.2 mL) was placed under a nitrogen atmosphere and treated with EtSH (0.055 mL, 0.743 mmol). The resulting solution was added by syringe to AlCl$_3$ (115.2 mg, 0.864 mmol) contained in an ice-cold flask and kept under nitrogen. The resulting solution was stirred at 0° C. for 3 minutes, then at room temperature for 35 minutes. The mixture was cooled in an ice bath, treated with 0.5N HCl (1.6 mL) and tetrahydrofuran (1.0 mL), and stirred at 0° C. for 10 minutes. The resulting mixture was diluted with EtOAc (20 mL) and water (15 mL) and stirred while basifying with solid NaHCO$_3$. The layers were separated and the aqueous portion extracted with EtOAc. The combined organics were washed with brine, dried over MgSO$_4$, filtered, and evaporated under vacuum to afford 9a-butyl-7-hydroxy-4-{4-[2-(1-piperidinyl)ethoxy]phenyl}-1,2,9,9a-tetrahydro-3H-fluoren-3-one as a yellow semi-solid.

$^1$H NMR (DMSO-d$_6$, 500 MHz) δ 0.82 (t, CH$_3$), 1.14–1.32 (m, CH$_2$CH$_2$), 1.38 (m, 4-CH$_2$ of piperidine), 1.40 and 1.66 (two m, CH$_2$), 1.50 (m, 3-CH$_2$ and 5-CH$_2$ of piperidine), 2.05 and 2.19 (two m, 1-CH$_2$), 2.36 and 2.57 (two m, 2-CH$_2$), 2.44 (br m, 2-CH$_2$ and 6-CH$_2$ of piperidine), 2.66 (t, NCH$_2$CH$_2$O), 2.68 and 2.92 (two d, 9-CH$_2$), 4.08 (t, NCH$_2$CH$_2$O), 6.18 (d, H-5), 6.35 (dd, H-6), 6.69 (d, H-8), 6.8–7.0 (br m, phenyl-H), and 9.96 (s, OH).

The product was converted to the hydrochloride salt as follows. The free base from above was dissolved in EtOAc, diluted with Et$_2$O, and treated with 1N HCl in Et$_2$O (0.2 mL). The resulting precipitate was collected, washed with Et$_2$O, and dried under vacuum to afford 9a-butyl-7-hydroxy-4-{4-[2-(1-piperidinyl)ethoxy]phenyl}-1,2,9,9a-tetrahydro-3H-fluoren-3-one hydrochloride as a pale orange solid.

$^1$H NMR (DMSO-d$_6$, 500 MHz) δ 0.82 (t, CH$_3$), 1.13–1.33 (m, CH$_2$CH$_2$), 1.40 (m, 2H's), 1.67 (m, 2H's), 1.80 (m, 4H's), 2.05 and 2.20 (two m, 1-CH$_2$), 2.36 and 2.57 (two m, 2-CH$_2$), 2.69 and 2.93 (two d, 9-CH$_2$), 3.01 (br s, 2H's), 3.50 (br m, 4H's), 4.42 (t, NCH$_2$CH$_2$O), 6.18 (d, H-5), 6.36 (dd, H-6), 6.72 (d, H-8), 6.85–7.1 (br m, phenyl-H), 10.07 (s, OH or NH), and 10.20 (br s, NH or OH).

IR (nujol mull) 1644, 1606, 1580, 1509, 1459, 1355, 1330, 1296, 1274, 1240, 1176, 1100, 999, 955, 870, 822, 723, 590, and 534 cm$^{-1}$.

Mass Spectrum, m/e 460.3.

EXAMPLE 11

SYNTHESIS OF 9a-BUTYL-7-HYDROXY-4-(4-HYDROXYPHENYL)-1,2,9,9a-TETRAHYDRO-3H-FLUOREN-3-ONE

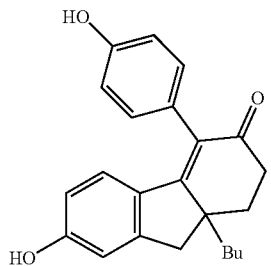

An ice-cold solution of 9a-butyl-4-(4-hydroxy-phenyl)-7-methoxy-1,2,9,9a-tetrahydro-3H-fluoren-3-one (29 mg, 0.08 mmol) in anhydrous CH$_2$Cl$_2$ (1 mL) was added to AlCl$_3$ (96 mg, 0.72 mmol) contained in an ice cooled flask. The mixture was stirred at 0° C. under a nitrogen atmosphere and treated with 2-propanethiol (0.056 mL, 0.6 mmol). The resulting mixture was stirred at 0° C. for 5 minutes and at room temperature for 3.25 hours, then treated with ice (approx. 2 mL), 2N HCl (2 mL) and EtOAc (4 mL) and stirred for 15 minutes at room temperature. The EtOAc layer was separated, washed with 1N HCl and brine, dried over MgSO$_4$, filtered, and evaporated under vacuum to give a yellow gum. This material was triturated with benzene to give, after filtration and drying under vacuum, 9a-butyl-7-hydroxy-4-(4-hydroxyphenyl)-1,2,9,9a-tetrahydro-3H-fluoren-3-one as an off-white solid.

$^1$H NMR (DMSO-d$_6$, 500 MHz) δ 0.82 (t, CH$_3$), 1.12–1.32 (m, CH$_2$CH$_2$), 1.39 and 1.64 (two m, CH$_2$), 2.03 and 2.18 (two m, 1-CH$_2$), 2.35 and 2.55 (two m, 2-CH$_2$), 2.67 and 2.91 (two d, 9-CH$_2$), 6.19 (d, H-5), 6.35 (dd, H-6), 6.68 (d, H-8), 6.7–7.9 (br m, phenyl-H), 9.41 (s, OH), and 9.97 (s, OH).

IR (nujol mull) 1608, 1572, 1512, 1480, 1359, 1333, 1300, 1270, 1239, 1207, 1101, 821, and 674 cm$^{-1}$.

Mass spectrum, m/e 349.1 (M+1).

EXAMPLE 12

SYNTHESIS OF (2E)-3-[4-(9a-BUTYL-7-HYDROXY-3-OXO-2,3,9,9a-TETRAHYDRO-1H-FLUOREN-4-YL)PHENYL]-2-PROPENOIC ACID

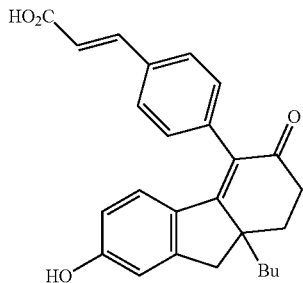

Step 1: 9a-butyl-7-methoxy-4-(4-trifluoromethanesulfonyloxy-phenyl)-1,2,9,9a-tetrahydro-3H-fluoren-3-one A solution of 9a-butyl-4-(4-hydroxyphenyl)-7-methoxy-1,2,9,9a-tetrahydro-3H-fluoren-3-one (303 mg, 91% weight pure, 0.76 mmol) and pyridine (0.307 mL, 3.8 mmol) in anhydrous CH$_2$Cl$_2$ (1.2 mL) was cooled in an ice bath and stirred under a nitrogen atmosphere while trifluoromethanesulfonic anhydride (0.147 mL, 0.87 mmol) was added dropwise by syringe. After stirring at 0° C. for 45 minutes, the reaction mixture was diluted with CH$_2$Cl$_2$ (20 mL) and shaken with water (10 ml) containing 1N NaOH (5 mL). The organic phase was separated, washed with water (10 mL), 1M pH 3 phosphate buffer (10 mL), water (10 mL), and brine (10 mL), dried over MgSO$_4$, filtered, and evaporated under vacuum to an orange solid (394 mg). The crude product was purified by flash chromatography on EM silica gel 60 (230–400 mesh, 25 mL dry, packed under 4:1 hexanes-EtOAc) using 4:1 hexanes-EtOAc as eluting solvent. The product containing fractions were evaporated under vacuum to a yellow solid (345 mg). This material was triturated with petroleum ether and dried under vacuum to afford 9a-butyl-7-methoxy-4-[4-(trifluoromethanesulfonyloxy)-phenyl]-1,2,9,9a-tetrahydro-3H-fluoren-3-one (313 mg) as a pale yellow solid.

$^1$H NMR (CDCl$_3$, 500 MHz) δ 0.88 (t, CH$_3$), 1.20–1.38 (m, CH$_2$CH$_2$), 1.51 and 1.73 (two m, CH$_2$), 2.13 and 2.34 (two m, 1-CH$_2$), 2.58 and 2.69 (two m, 2-CH$_2$), 2.79 and 3.03 (two d, 9-CH$_2$), 3.79 (s, OCH$_3$), 6.21 (d, H-5), 6.48 (dd, H-6), 6.79 (d, H-8), and 7.10–7.45 (br m, phenyl-H).

Step 2: methyl (2E)-3-[4-(9a-butyl-7-methoxy-3-oxo-2,3,9,9a-tetrahydro-1H-fluoren-4-yl)phenyl]-2-propenoate A mixture of 9a-butyl-7-methoxy-4-[4-(trifluoromethanesulfonyloxy)-phenyl]-1,2,9,9a-tetrahydro-3H-fluoren-3-one (98.9 mg, 0.2 mmol), methyl (E)-3-tributylstannyl-acrylate (112.5 mg, 0.3 mmol) and lithium chloride (25.4 mg, 0.6 mmol) in anhydrous dimethylformamide (1.0 mL) was purged with nitrogen and treated with bis(triphenylphosphine)palladium(II) chloride (7.0 mg, 0.01 mmol). The resulting mixture was purged with nitrogen then stirred under a nitrogen atmosphere with heating in an oil bath at 90° C. for 60 minutes. After cooling, the solvent was evaporated under vacuum. The residue in EtOAc (10 mL) was washed with water (2×5 mL) and brine (5 ml), dried over MgSO$_4$, filtered, and evaporated under vacuum to a gum (194 mg). The crude product was purified by preparative layer chromatography (PLC) on two 0.1×20×20 cm silica gel GF plates, developing with 4:1-hexanes-EtOAc. The major UV visible band at R$_f$ 0.15–0.25 was eluted with EtOAc and the solvent evaporated under vacuum to afford methyl (2E)-3-[4-(9a-butyl-7-methoxy-3-oxo-2,3,9,9a-tetrahydro-1H-fluoren-4-yl)phenyl]-2-propenoate (83 mg) as a pale yellow solid. NMR showed approximately 7–8% of a Bu$_3$SnX impurity.

$^1$H NMR (CDCl$_3$, 500 MHz) δ 0.89 (t, CH$_3$), 1.21–1.39 (m, CH$_2$CH$_2$), 1.53 and 1.74 (two m, CH$_2$), 2.13 and 2.33 (two m, 1-CH$_2$), 2.58 and 2.69 (two m, 2-CH$_2$), 2.79 and 3.03 (two d, 9-CH$_2$), 3.78 (s, OCH$_3$), 3.82 (s, OCH$_3$), 6.36 (d, H-5), 6.48 (dd, H-6), 6.48 and 7.75 (two d, CH═CH), 6.79 (d, H-8), 7.05–7.25 (br m, two phenyl-H), and 7.5–7.66 (br m, two phenyl-H).

Step 3: (2E)-3-[4-(9a-butyl-7-hydroxy-3-oxo-2,3,9,9a-tetrahydro-1H-fluoren-4-yl)phenyl]-2-propenoic acid A mixture of methyl (2E)-3-[4-(9a-butyl-7-methoxy-3-oxo-2,3,9,9a-tetrahydro-1H-fluoren-4-yl)phenyl]-2-propenoate (60 mg, 92% weight pure, 0.128 mmol) and pyridine hydrochloride (741 mg, 6.41 mmol) was placed under a nitrogen atmosphere, heated in an oil bath at 190° C., and stirred. The reaction flask was periodically dipped deeper into the heating bath in order to melt the pyridine hydrochloride that condensed on the sides of the flask. After 2 hours at 190° C., the reaction mixture was cooled to room temperature and partitioned between EtOAc (10 mL) and water (10 mL). The aqueous phase was extracted with more EtOAc (2×5 mL). The combined EtOAc extracts were washed with brine, dried over MgSO$_4$, filtered, and evaporated under vacuum to a yellow solid (55 mg). The crude product was suspended in EtOAc (10 mL) and extracted with 5% NaHCO$_3$ (5 mL). The NaHCO$_3$ solution was acidified with 2N HCl (2.5 mL) and extracted with EtOAc (2×5 mL). The latter EtOAc extracts were combined, washed with brine, dried over MgSO$_4$, filtered, and evaporated under vacuum to a yellow solid (39.4 mg). This material was triturated with diethyl ether and dried under vacuum to afford (2E)-3-[4-(9a-butyl-7-hydroxy-3-oxo-2,3,9,9a-tetrahydro-1H-fluoren-4-yl)phenyl]-2-propenoic acid as a pale yellow solid.

$^1$H NMR (CD$_3$OD, 500 MHz) δ 0.89 (t, CH$_3$), 1.21–1.41 (m, CH$_2$CH$_2$), 1.55 and 1.76 (two m, CH$_2$), 2.15 and 2.34 (two m, 1-CH$_2$), 2.51 and 2.71 (two m, 2-CH$_2$), 2.76 and 3.01 (two d, 9-CH$_2$), 6.24 (d, H-5), 6.34 (dd, H-6), 6.53 and 7.73 (two d, CH═CH), 6.71 (d, H-8), 7.0–7.3 (br m, two phenyl-H), and 7.6–7.72 (br m, two phenyl-H).

Mass spectrum, m/e 403.3 (M+1).

EXAMPLE 13

SYNTHESIS OF 9a-BUTYL-7-HYDROXY-8-METHYL-1,2,9,9a-TETRAHYDRO-3H-FLUOREN-3-ONE

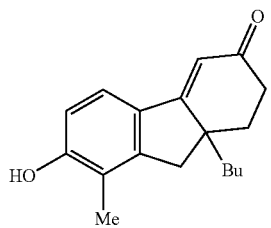

Step 1: 4-bromo-2-butyl-5-methoxy-1-indanone

A solution of 2-butyl-5-methoxy-1-indanone (1.869 g, 8.56 mmol) in anhydrous dimethylformamide (8.6 mL) was treated with N-bromosuccinamide (1.676 g, 9.42 mmol).

The resulting mixture was stirred under a nitrogen atmosphere and at room temperature for 14 hours, and then heated in an oil bath at 50° C. for 4 hours. After cooling to room temperature, the mixture was diluted with EtOAc (100 mL), washed with water (4×50 mL) and brine (50 mL), dried over MgSO4, and evaporated under vacuum to a dark amber oil (2.468 g). The crude product was purified by column chromatography on EM silica gel 60 (230–400 mesh, 620 mL dry, packed under $CH_2Cl_2$), using $CH_2Cl_2$ as eluting solvent, to afford 4-bromo-2-butyl-5-methoxy-1-indanone (1.267 g, contains approx. 3% of the 6-bromo isomer) as a pale tan solid. Earlier fractions afforded the 6-bromo isomer.

$^1$H NMR (CDCl$_3$, 500 MHz) δ 0.92 (t, CH$_3$), 1.30–1.46 (m, CH$_2$CH$_2$), 1.47 and 1.95 (two m, CH$_2$), 2.68 (m, H-2), 2.72 and 3.25 (two dd, 3-CH$_2$), 3.99 (s, OCH$_3$), 6.93 and 7.70 (two d, H-6 and H-7).

Step 2: 2-butyl-5-methoxy-4-methyl-1-indanone

A solution of 4-bromo-2-butyl-5-methoxy-1-indanone (1.159 g, 3.90 mmol) in anhydrous dimethylformamide (39 mL) was treated with LiCl (455 mg, 10.73 mmol), PPh$_3$ (205 mg, 0.78 mmol), PdCl$_2$(PPh$_3$)$_2$ (205 mg, 0.292 mmol) and Me$_4$Sn (1.08 mL, 7.80 mmol). The mixture was placed under a nitrogen atmosphere, then stirred and heated in an oil bath at 100° C. for 16.5 hours. After cooling to room temperature, the mixture was diluted with water (100 mL) and extracted with Et$_2$O (100 mL, 2×25 mL). The ether extracts were washed with brine, dried over MgSO$_4$, filtered and evaporated under vacuum to a yellow solid (1.29 g). This material was purified by chromatography on EM silica gel 60 (230–400 mesh, 130 mL dry, packed under CH$_2$Cl$_2$), using CH$_2$Cl$_2$ as eluting solvent, to afford a 92:3:5 mixture (0.90 g) of 2-butyl-5-methoxy-4-methyl-1-indanone, the 6-methyl isomer, and the desmethyl product. This material was used as is in the next step.

$^1$H NMR (CDCl$_3$, 500 MHz) δ 0.92 (t, CH$_3$), 1.30–1.48 (m, CH$_2$CH$_2$ and CHaHb), 1.95 (m, CHaHb), 2.18 (s, 4-CH$_3$), 2.63 (m, H-2), 2.65 and 3.19 (two dd, 3-CH$_2$), 3.91 (s, OCH$_3$), 6.89 and 7.63 (two d, H-6 and H-7).

Step 3: 2-butyl-5-methoxy-4-methyl-2-(3-oxo-butyl)-1-indanone

Methyl vinyl ketone (MVK, 0.49 mL, 5.9 mmol) and 1,8-diazabicyclo[5.4.0]undec-7-ene (DBU, 0.12 mL, 0.8 mmol) were added to a solution of impure 2-butyl-5-methoxy-4-methyl-1-indanone (0.90 g, 3.9 mmol) in anhydrous tetrahydrofuran (THF, 3.9 mL). The resulting solution was stirred at room temperature for 30 hours, then diluted with Et$_2$O (50 mL), washed with water (20 mL), 1N HCl (20 mL), and brine (20 mL), dried over MgSO$_4$, filtered, and evaporated under vacuum to an amber oil (1.23 g). The crude product was purified by chromatography on EM silica gel 60 (230–400 mesh, 125 mL dry, packed under 4:1 hexanes-EtOAc). The column was eluted with 4:1 hexanes-EtOAc, collecting 25 mL fractions. Fractions 14–27 gave a 93:2:5 mixture (0.96 g) of 2-butyl-5-methoxy-4-methyl-2-(3-oxo-butyl)-1-indanone, the 6-methyl isomer, and the desmethyl product. This material was used in the next step.

$^1$H NMR (CDCl$_3$, 500 MHz) δ 0.83 (t, CH$_2$CH$_2$CH$_2$CH$_3$), 1.07 and 1.17 (two m, CH$_2$CH$_2$CH$_2$CH$_3$), 1.24 (m, CH$_2$CH$_2$CH$_2$CH$_3$), 1.59 (m, CH$_2$CH$_2$CH$_2$CH$_3$), 1.81–1.95 (m, CH$_2$CH$_2$CO), 2.06 (s, 4-CH$_3$), 2.17 (s, COCH$_3$), 2.31 (t, CH$_2$CH$_2$CO), 2.75 and 2.91 (two d, 3-CH$_2$), 3.91 (s, OCH$_3$), 6.90 and 7.61 (two d, H-6 and H-7).

Step 4: 9a-butyl-7-methoxy-8-methyl-1,2,9,9a-tetrahydro-3H-fluoren-3-one

A solution of impure 2-butyl-5-methoxy-4-methyl-2-(3-oxo-butyl)-1-indanone (0.96 g, 3.17 mmol), acetic acid (0.182 mL, 3.18 mmol) and pyrrolidine (0.265 mL, 3.18 mmol) in anhydrous toluene (15.9 mL) was stirred and heated in an oil bath at 80° C. for 16 hours. After cooling, the reaction mixture was diluted with Et$_2$O (100 mL), washed with 1N HCl (2×25 mL), 5% NaHCO$_3$ (50 mL), and brine (50 mL), dried over MgSO$_4$, filtered, and evaporated under vacuum to a dark brown oil (0.86 g). The crude product was purified by chromatography on a Biotage FLASH 40S column, eluting with 9:1 hexanes-EtOAc, to afford 9a-butyl-7-methoxy-8-methyl-1,2,9,9a-tetrahydro-3H-fluoren-3-one (0.50 g) as an off-white solid.

$^1$H NMR (CDCl$_3$, 500 MHz) δ 0.85 (t, CH$_3$), 1.16–1.32 (m, CH$_2$CH$_2$), 1.44 and 1.63 (two m, CH$_2$), 1.97 and 2.29 (two m, 1-CH$_2$), 2.15 (s, 8-CH$_3$), 2.44 and 2.55 (two m, 2-CH$_2$), 2.58 and 2.99 (two d, 9-CH$_2$), 3.88 (s, OCH$_3$), 6.82 (d, H-6), and 7.41 (d, H-5).

Step 5: 9a-butyl-7-hydroxy-8-methyl-1,2,9,9a-tetrahydro-3H-fluoren-3-one

A solution of 9a-butyl-7-methoxy-8-methyl-1,2,9,9a-tetrahydro-3H-fluoren-3-one (28.4 mg, 0.1 mmol) in anhydrous CH$_2$Cl$_2$ (1.7 mL) was stirred under a nitrogen atmosphere and cooled in a dry ice-acetone bath while 1M BBr$_3$ in CH$_2$Cl$_2$ (0.30 mL, 0.3 mmol) was added dropwise by syringe. The cooling bath was removed and the reaction mixture was stirred at room temperature for 4 hours. The mixture was diluted with EtOAc (8 mL), water (3 mL) and 1N HCL (1 mL) and shaken vigorously. The EtOAc layer was separated, washed with water (3 mL), 1M pH 3 phosphate (3 mL) and brine (3 mL), dried over MgSO$_4$, filtered and evaporated under vacuum to give an ochre solid (26.8 mg). The crude product was suspended in CDCl$_3$ (1 mL) and filtered. The solid portion was dried under vacuum to afford 9a-butyl-7-hydroxy-8-methyl-1,2,9,9a-3H-tetrahydro-fluoren-3-one as an olive colored powder.

$^1$H NMR (DMSO-d$_6$, 500 MHz) δ 0.79 (t, CH$_3$), 1.07–1.27 (m, CH$_2$CH$_2$), 1.32 and 1.54 (two m, CH$_2$), 1.88 and 2.18 (two m, 1-CH$_2$), 2.04 (s, 8-CH$_3$), 2.23 and 2.44 (two m, 2-CH$_2$), 2.54 and 2.92 (two d, 9-CH$_2$), 6.00 (s, H-4), 6.77 (H-6), 7.38 (d, H-5), and 9.99 (br s, OH).

IR (nujol mull) 1624, 1602, 1575, 1452, 1436, 1361, 1291, 1265, 1253, 1236, 1220, 1200, 1062, 1048, 991, 889, and 830 cm$^{-1}$.

Mass spectrum, m/e 271.1 (M+1).

EXAMPLE 14

SYNTHESIS OF 4-BROMO-9a-BUTYL-7-HYDROXY-8-METHYL-1,2,9,9a-TETRAHYDRO-3H-FLUOREN-3-ONE

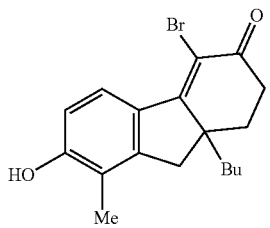

Step 1: 4-bromo-9a-butyl-7-methoxy-8-methyl-1,2,9,9a-tetrahydro-3H-fluoren-3-one A mixture of 9a-butyl-7-methoxy-8-methyl-1,2,9,9a-tetrahydro-3H-fluoren-3-one (133 mg, 0.468 mmol), CCl$_4$ (0.94 mL), and NaHCO$_3$ (196 mg, 2.333 mmol) was cooled in an ice bath and stirred. Bromine (0.024 mL, 0.467 mmol) was added while stirring and swirling the reaction mixture by hand. A gummy, red precipitate formed during the addition. The mixture was swirled by hand for 5 minutes in order to break up the gum, which gradually changed to a stirrable orange solid. The mixture was stirred and swirled a total of 35 minutes at 0° C. The mixture was diluted with CH$_2$Cl$_2$ and water and shaken. The organic phase was separated, washed with water containing Na$_2$S$_2$O$_4$, washed with brine, dried over MgSO$_4$, filtered, and evaporated under vacuum to a yellow gum (241 mg). The crude product was purified by preparative layer chromatography on two 0.1×20×20 cm silica gel GF plates, developing with 4:1 hexanes-EtOAc. The major UV visible band at R$_f$ 0.39–0.50 was eluted with EtOAc and evaporated under vacuum to give 4-bromo-9a-butyl-7-methoxy-8-methyl-1,2,9,9a-tetrahydro-3H-fluoren-3-one (151 mg) as a white solid.

$^1$H NMR (CDCl$_3$, 500 MHz) δ 0.84 (t, CH$_3$), 1.16–1.29 (m, CH$_2$CH$_2$), 1.46 and 1.64 (two m, CH$_2$), 2.07 and 2.27 (two m, 1-CH$_2$), 2.16 (s, 8-CH$_3$), 2.65 and 2.99 (two d, 9-CH$_2$), 2.68–2.79 (m, 2-CH$_2$), 3.91 (s, OCH$_3$), 6.84 (d, H-6), and 8.42 (d, H-5).

Step 3: 4-bromo-9a-butyl-7-hydroxy-8-methyl-1,2,9,9a-tetrahydro-3H-fluoren-3-one A solution of 4-bromo-9a-butyl-7-methoxy-8-methyl-1,2,9,9a-tetrahydro-3H-fluoren-3-one (36.3 mg, 0.1 mmol) in anhydrous CH$_2$Cl$_2$ (1.7 mL) was cooled in a dry ice-acetone bath and stirred under a N$_2$ atmosphere. A 1 M solution of BBr$_3$ in CH$_2$Cl$_2$ (0.30 mL, 0.3 mmol) was added dropwise by syringe. The cooling bath was removed and the mixture was stirred at room temperature for 3.5 hours. The mixture was diluted with water (3 mL), 1N HCl (1 mL), and EtOAc (8 mL) and shaken. The EtOAc phase was separated, washed with water (3 mL), 1M pH 3 phosphate (3 mL) and brine (3 mL), dried over MgSO$_4$, filtered, and evaporated under vacuum to give a dark green gum (38 mg). This material was purified by preparative layer chromatography on a 0.1×20×20 cm silica gel GF plate using 5% MeOH in EtOAc as developing solvent. The major UV visible band at R$_f$ 0.40–0.51 was eluted with EtOAc to give a yellow solid (23.5 mg). The solid was recrystallized from Et$_2$O-hexanes to afford 4-bromo-9a-butyl-7-hydroxy-8-methyl-1,2,9,9a-tetrahydro-3H-fluoren-3-one as an off-white, fibrous solid.

$^1$H NMR (CDCl$_3$, 500 MHz) δ 0.85 (t, CH$_3$), 1.15–1.29 (m, CH$_2$CH$_2$), 1.47 and 1.65 (two m, CH$_2$), 2.07 and 2.27 (two m, 1-CH$_2$), 2.20 (s, 8-CH$_3$), 2.66 and 2.99 (two d, 9-CH$_2$), 2.69–2.80 (m, 2-CH$_2$), 6.83 (d, H-6), and 8.33 (d, H-5).

$^{13}$C NMR (CDCl$_3$, 125 MHz) δ 11.78, 13.93, 23.09, 27.56, 31.29, 34.18, 38.00, 42.05, 51.27, 112.36, 114.44, 120.23, 127.11, 127.13, 130.31, 150.37, 157.40, 169.38, and 191.45.

IR (nujol mull) 1637, 1552, 1458, 1376, 1293, 1251, 1203, 1064, 825, and 735 cm$^{-1}$.

Mass spectrum, m/e 349.0 (M+1), 351.0.

EXAMPLE 15

SYNTHESIS OF 9a-BUTYL-4,8-DIMETHYL-7-HYDROXY-1,2,9,9a-TETRAHYDRO-3H-FLUOREN-3-ONE

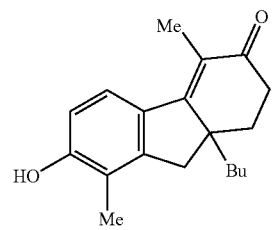

Step 1: 2-butyl-5-methoxy-4-methyl-2-(3-oxopentyl)-1-indanone

A solution of 2-butyl-5-methoxy-4-methyl-1-indanone (100 mg, 0.43 mmol) in tetrahydrofuran (0.43 mL) was treated with ethyl vinyl ketone (EVK, 0.064 mL, 0.646 mmol) and 1,8-diazabicyclo[5.4.0]undec-7-ene (DBU, 0.013 mL, 0.086 mmol). The resulting solution was stirred under a nitrogen atmosphere and heated in an oil bath at 60° C. After 24 hour, more EVK (0.064 mL) and DBU (0.013 mL) were added and the solution was heated an additional 24 hours at 60° C. The reaction mixture was diluted with EtOAc (10 mL) and washed with water (10 mL) containing 2N HCl (1 mL). The organic phase was washed with brine (5 mL), dried over MgSO$_4$, filtered, and evaporated under vacuum to provide crude 2-butyl-5-methoxy-4-methyl-2-(3-oxopentyl)-1-indanone.

$^1$H NMR (CDCl$_3$, 500 MHz) δ 0.85 (t, CH$_2$CH$_2$CH$_2$CH$_3$), 1.01 (t, COCH$_2$CH$_3$), 1.08 (m, CH$_2$CH$_2$CH$_2$CH$_3$), 1.26 (m, CH$_2$CH$_2$CH$_2$CH$_3$), 1.61 (m, CH$_2$CH$_2$CH$_2$CH$_3$), 1.91 (m, CH$_2$CH$_2$CO), 2.19 (s, 4-CH$_3$), 2.30 (m, CH$_2$CH$_2$CO), 2.36 (m, COCH$_2$CH$_3$), 2.78 and 2.93 (two d, 3-CH$_2$), 3.94 (s, OCH$_3$), 6.92 (d, H-6), and 7.63 (d, H-7).

Step 2: 9a butyl-4,8-dimethyl-7-methoxy-1,2,9,9a-tetrahydro-3H-fluoren-3-one

A solution of the crude diketone from step 1 in acetic acid (1 mL) and 6N HCl (1 mL) was stirred and heated in an oil bath at 100° C. for 5 hours. After cooling, the reaction mixture was diluted with EtOAc (20 mL), washed with water (10 mL) and brine (10 mL), dried over MgSO$_4$, filtered, and the solvent evaporated under vacuum. The residue was purified by preparative layer chromatography on two 0.1×20×20 cm silica gel GF plates, using 5% EtOAc in CH$_2$Cl$_2$ as developing solvent, to afford 9a butyl-4,8-dimethyl-7-methoxy-1,2,9,9a-tetrahydro-3H-fluoren-3-one (84 mg) as a gum.

$^1$H NMR (CDCl$_3$, 500 MHz) δ 0.85 (t, CH$_3$), 1.17–1.31 (m, CH$_2$CH$_2$), 1.38 and 1.60 (two m, CH$_2$), 1.99 and 2.26 (two m, 1-CH$_2$), 2.09 (s, 4-CH$_3$), 2.17 (s, 8-CH$_3$), 2.48 and 2.59 (two m, 2-CH$_2$), 2.59 and 2.97 (two d, 9-CH$_2$), 3.91 (s, OCH$_3$), 6.84 (d, H-6), and 7.57 (d, H-5).

Step 3: 9a butyl-4,8-dimethyl-7-hydroxy-1,2,9,9a-tetrahydro-3H-fluoren-3-one

A solution of 9a butyl-4,8-dimethyl-7-methoxy-1,2,9,9a-tetrahydro-3H-fluoren-3-one (84 mg, 0.28 mmol) in anhydrous CH$_2$Cl$_2$ (3 mL) was placed under a nitrogen atmosphere, cooled in an acetone-dry ice bath, and treated with 1M BBr$_3$ in CH$_2$Cl$_2$ (1.11 mL, 1.11 mmol). The cooling bath was removed and the reaction mixture was stirred at room temperature for 4 hours. The reaction mixture was diluted with EtOAc (20 mL), washed with water (20 ml) containing 2N HCl (2 mL) followed by brine (10 mL), dried over MgSO$_4$, filtered, and evaporated under vacuum. The crude product was purified by preparative layer chromatography on a 0.1×20×20 cm silica gel GF plate, developing with 10% EtOAc in CH$_2$Cl$_2$. The UV visible product band was eluted with EtOAc and the solvent evaporated under vacuum. The residue was lyophilized from benzene-methanol to afford 9a butyl-4,8-dimethyl-7-hydroxy-1,2,9,9a-tetrahydro-3H-fluoren-3-one as a solid.

$^1$H NMR (DMSO-d$_6$, 500 MHz) δ 0.77 (t, CH$_3$), 1.15 (m, CH$_2$CH$_2$), 1.25 and 1.50 (two m, CH$_2$), 1.89 and 2.13 (two m, 1-CH$_2$), 1.90 (s, 4-CH$_3$), 2.04 (s, 8-CH$_3$), 2.27 and 2.47 (two m, 2-CH$_2$), 2.52 and 2.88 (two d, 9-CH$_2$), 6.79 (d, H-6), 7.38 (d, H-5), and 9.90 (s, OH).

EXAMPLE 16

SYNTHESIS OF 9a-BUTYL-8-CHLORO-7-HYDROXY-4-METHYL-1,2,9,9a-TETRAHYDRO-3H-FLUOREN-3-ONE

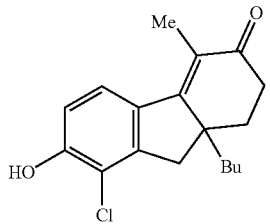

Step 1: 2-butyl-4-chloro-5-methoxy-1-indanone

N-Chlorosuccinimide (505 mg, 3.8 mmol) was added to a solution of 2-butyl-5-methoxy-1-indanone (825 mg, 3.8 mmol) in anhydrous dimethylformamide (3.8 mL) and the resulting solution was stirred under nitrogen and at room temperature overnight. The reaction mixture was diluted with EtOAc (50 mL), washed with 5% aqueous NaHCO$_3$ (20 ml), water (3×50 mL) and brine (10 mL), dried over MgSO$_4$, filtered, and evaporated under vacuum. The residue was purified by column chromatography on EM silica gel 60 (2320–400 mesh, 2.75×29 cm), eluting with CH$_2$Cl$_2$, to afford 2-butyl-4-chloro-5-methoxy-1-indanone (148 mg) as an oil.

$^1$H NMR (CDCl$_3$, 500 MHz) δ 0.93 (t, CH$_3$), 1.31–1.52 (m, CHaHbCH$_2$CH$_2$), 1.95 (m, CHaHbCH$_2$CH$_2$), 2.68 (m, H-2), 2.76 and 3.30 (two dd, 3-CH$_2$), 4.00 (s, OCH$_3$), 6.98 (d, H-6), and 7.67 (d, H-7).

Step 2: 2-butyl-4-chloro-5-methoxy-2-(3-oxopentyl)-1-indanone

A solution of 2-butyl-4-chloro-5-methoxy-1-indanone (200 mg, 0.79 mmol) in anhydrous tetrahydrofuran (0.8 mL) was placed under a nitrogen atmosphere and treated with ethyl vinyl ketone (0.118 mL, 1.19 mmol) followed by 1,8-diazabicyclo[5.4.0]undec-7-ene (0.024 mL, 0.158 mmol). The resulting solution was stirred and heated in an oil bath at 60° C. for 47 hours. After cooling to room temperature, the reaction mixture was diluted with EtOAc (20 mL) and washed with water (20 mL) containing 2N HCl (2 mL). The organic phase was washed with brine (10 mL), dried over MgSO$_4$, filtered, and evaporated under vacuum to provide crude 2-butyl-4-chloro-5-methoxy-2-(3-oxopentyl)-1-indanone (250 mg) as an oil.

$^1$H NMR (CDCl$_3$, 500 MHz) δ 0.86 (t, CH$_2$CH$_2$CH$_2$CH$_3$), 1.02 (t, COCH$_2$CH$_3$), 1.04–1.25 (m, CH$_2$CH$_2$CH$_2$CH$_3$), 1.27 (m, CH$_2$CH$_2$CH$_2$CH$_3$), 1.62 (m, CH$_2$CH$_2$CH$_2$CH$_3$), 1.92 (m, CH$_2$CH$_2$CO), 2.31 (m, CH$_2$CH$_2$CO), 2.37 (m, COCH$_2$CH$_3$), 2.88 and 3.03 (two d, 3-CH$_2$), 4.02 (s, OCH$_3$), 7.01 (d, H-6), and 7.67 (d, H-7).

Step 3: 9a-butyl-8-chloro-7-methoxy-4-methyl-1,2,9,9a-tetrahydro-3H-fluoren-3-one A solution of 2-butyl-4-chloro-5-methoxy-2-(3-oxopentyl)-1-indanone (250 mg, 0.74 mmol) in acetic acid (2 mL) was diluted with 6N aqueous HCl (2 mL). The resulting mixture was stirred and heated in an oil bath at 90° C. for 18 hours, then kept at room temperature for 2 days. The mixture was diluted with EtOAc (20 mL), washed with water (30 mL), 5% NaHCO$_3$ (10 mL) and brine (5 mL), dried over MgSO$_4$, filtered, and evaporated under vacuum to an oil (250 mg). The crude product was purified by preparative layer chromatography on three 0.1×20×20 silica gel GF plates, developing with 5% EtOAc in CH$_2$Cl$_2$, to afford 9a-butyl-8-chloro-7-methoxy-4-methyl-1,2,9,9a-tetrahydro-3H-fluoren-3-one (143 mg).

$^1$H NMR (CDCl$_3$, 500 MHz) δ 0.86 (t, CH$_3$), 1.15–1.30 (m, CH$_2$CH$_2$), 1.40 and 1.60 (two m, CH$_2$), 2.02 and 2.28 (two m, 1-CH$_2$), 2.08 (s, 4-CH$_3$), 2.49 and 2.60 (two m, 2-CH$_2$), 2.70 and 3.11 (two d, 9-CH$_2$), 3.98 (s, OCH$_3$), 6.92 (d, H-6), and 7.60 (d, H-5).

Step 4: 9a-butyl-8-chloro-7-hydroxy-4-methyl-1,2,9,9a-tetrahydro-3H-fluoren-3-one A mixture of 9a-butyl-8-chloro-7-methoxy-4-methyl-1,2,9,9a-tetrahydro-3H-fluoren-3-one (36.6 mg) and pyridine hydrochloride (2.66) was stirred and heated in an oil bath at 190–200° C. for 80 minutes. After cooling to room temperature, the mixture was partitioned between EtOAc (20 mL) and water (30 mL). The organic phase was washed with brine (10 mL), dried over MgSO$_4$, filtered, and evaporated under vacuum. The residue was purified by preparative layer chromatography on a 0.1×20×20 cm silica gel GF plate, developing with 10% EtOAc in CH$_2$Cl$_2$. The UV visible product band was eluted with EtOAc, the eluant evaporated under vacuum, and the residue lyophilized from benzene to afford 9a-butyl-8-chloro-7-hydroxy-4-methyl-1,2,9,9a-tetrahydro-3H-fluoren-3-one as an amorphous solid.

$^1$H NMR (DMSO-d$_6$, 500 MHz) δ 0.77 (t, CH$_3$), 1.04–1.23 (m, CH$_2$CH$_2$), 1.28 and 1.52 (two m, CH$_2$), 1.91 (s, 4-CH$_3$), 1.96 and 2.14 (two m, 1-CH$_2$), 2.29 and 2.49 (two m, 2-CH$_2$), 2.65 and 2.93 (two d, 9-CH$_2$), 6.95 (d, H-6), and 7.52 (d, H-5).

IR (KBr) 3416, 2954, 2859, 1610, 1459, 1343, 1270, 1100, 944, 867, and 820 cm$^{-1}$.

Mass spectrum, m/e 333.0 (M+1), 335.0.

EXAMPLE 17

SYNTHESIS OF (2SR,9aSR)-9a-BUTYL-2,4-DIMETHYL-7-HYDROXY-1,2,9,9a-TETRAHYDRO-3H-FLUOREN-3-ONE

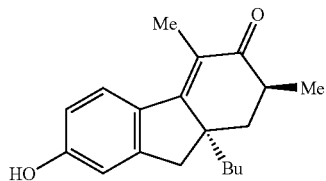

Step 1: (2SR,9aSR)-9a-butyl-2,4-dimethyl-7-methoxy-1,2,9,9a-tetrahydro-3H-fluoren-3-one A solution of 9a-butyl-7-methoxy-4-methyl-1,2,9,9a-tetrahydro-3H-fluoren-3-one (142 mg, 0.5 mmol) in anhydrous tetrahydrofuran (THF, 2.5 mL) was placed under a nitrogen atmosphere, cooled with stirring in an ice bath, and treated with lithium diisopropylamide (1.5 mL of a 0.4 M solution in THF/hexanes, 0.6 mmol). After 40 minutes at 0°

C., the solution was cooled to −78° C. (dry ice-acetone bath) and iodomethane (0.16 mL, 2.5 mmol) was added. The resulting solution was allowed to slowly warm to room temperature. After 16 hours at room temperature, the solution was diluted with EtOAc (50 mL) and washed with 1 N HCl (30 mL). The aqueous acid phase was back-extracted with EtOAc (25 mL). The combined organics were washed successively with 5% aq. NaHCO$_3$, water, and brine (30 mL each), dried over MgSO$_4$, filtered, and evaporated under vacuum to afford 147 mg of yellow oil. This material was purified by preparative layer chromatography (0.1×20×20 cm silica gel GF plate), using 5:1 hexanes-EtOAc as eluting solvent, to afford (2SR,9aSR)-9a-butyl-2,4-dimethyl-7-methoxy-1,2,9,9a-tetrahydro-3H-fluoren-3-one (112 mg) as a faintly yellow oil.

$^1$H NMR (CDCl$_3$, 500 MHz) δ 0.86 (t, CH$_3$), 1.20–1.31 (m, CH$_2$CH$_2$), 1.23 (d, 2-CH$_3$) 1.35 and 1.62 (two m, CH$_2$), 1.74 (t, H-1a), 2.09 (s, 4-CH$_3$), 2.28 (dd, H-1b), 2.56 (m, H-2), 2.69 and 2.96 (two d, 9-CH$_2$), 3.87 (s, OCH$_3$), 6.85–6.87 (m, H-6 and H-8), and 7.65 (d, H-5).

Step 2: (2SR,9aSR)-9a-butyl-2,4-dimethyl-7-hydroxy-1,2,9,9a-tetrahydro-3H-fluoren-3-one A solution of (2SR,9aSR)-9a-butyl-2,4-dimethyl-7-methoxy-1,2,9,9a-tetrahydro-3H-fluoren-3-one (112 mg, 0.38 mmol) in dichloromethane (CH$_2$Cl$_2$) was cooled to −78° C. under a nitrogen and treated with boron tribromide (1.12 mL of a 1M solution in CH$_2$Cl$_2$, 1.12 mmol). The cooling bath was removed after five minutes and the reaction mixture stirred for 17 hours at room temperature, after which time additional boron tribromide (1 mL, 1 mmol) was added. After 23 hours, the reaction mixture was diluted with EtOAc (50 mL), washed with 1 N HCl, 5% aq. NaHCO$_3$, and brine (30 mL each), then dried over MgSO$_4$, filtered and concentrated under vacuum. The crude product was purified by preparative layer chromatography (PLC, 0.1×20×20 cm silica gel GF plate), developing with 4/1 hexanes-EtOAc, to give the product as a yellow oil (17 mg). This oil was repurified by PLC, using the same conditions, and the product lyophilized from benzene to give (2SR,9aSR)-9a-butyl-2,4-dimethyl-7-hydroxy-1,2,9,9a-tetrahydro-3H-fluoren-3-one (90% pure).

$^1$H NMR (CDCl$_3$, 500 MHz) δ 0.86 (t, CH$_3$), 1.20–1.31 (m, CH$_2$CH$_2$), 1.23 (d, 2-CH$_3$) 1.36 and 1.60 (two m, CH$_2$), 1.74 (t, H-1a), 2.08 (s, 4-CH$_3$), 2.29 (dd, H-1b), 2.57 (m, H-2), 2.68 and 2.94 (two d, 9-CH$_2$), 5.1 (s, OH), 6.78–6.81 (m, H-6 and H-8), and 7.61 (d, H-5).

EXAMPLE 18

SYNTHESIS OF (2SR,9aRS)-9a-BUTYL-2,4-DIMETHYL-7-HYDROXY-2-PROPYL-1,2,9,9a-TETRAHYDRO-3H-FLUOREN-3-ONE

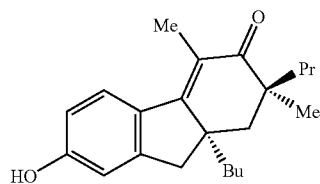

Step 1: 9a-butyl-7-methoxymethoxy-4-methyl-1,2,9,9a-tetrahydro-3H-fluoren-3-one

A solution of 9a-butyl-7-hydroxy-4-methyl-1,2,9,9a-tetrahydro-3H-fluoren-3-one (5.30 g, 21 mmol) in anhydrous dimethylformamide (50 mL) was cooled in an ice bath, stirred under a nitrogen atmosphere, and treated successively with N,N-diisopropyl-ethylamine (10.5 mL, 60 mmol) and chloromethyl methyl ether (3.45 mL, 41 mmol). The resulting mixture was stirred while gradually warming to room temperature over 5 hours. After 5.5 hours, additional N,N-diisopropyl-ethylamine (3 mL) and chloromethyl methyl ether (1 mL) were added. After stirring an additional 25 minutes at room temperature, the reaction mixture was diluted with EtOAc (1 L) and washed with 1.3N HCl (1 L). The aqueous phase was separated and extracted with EtOAc (200 mL). The combined organics were washed with 5% NaHCO$_3$ (500 ml) and brine, dried over MgSO$_4$, filtered, and concentrated under vacuum to an orange oil (6.5 g). This material was divided into three portions and each purified by flash chromatography on silica gel using Biotage FLASH 40M columns and 10:1 hexanes-EtOAc as eluting solvent. The product containing fractions were combined and evaporated under vacuum to afford 9a-butyl-7-methoxymethoxy-4-methyl-1,2,9,9a-tetrahydro-3H-fluoren-3-one (4.98 g) as an oil.

$^1$H NMR (CDCl$_3$, 500 MHz) δ 0.86 (t, CH$_3$), 1.18–1.32 (m, CH$_2$CH$_2$), 1.39 and 1.60 (two m, CH$_2$), 1.98 and 2.25 (two m, 1-CH$_2$), 2.09 (s, 4-CH$_3$), 2.48 and 2.59 (two m, 2-CH$_2$), 2.72 and 2.98 (two d, 9-CH$_2$), 3.52 (s, OCH$_3$), 5.24 (m, OCH$_2$O), 6.98 (dd, H-6), 7.02 (d, H-8), and 7.66 (dd, H-5).

Step 2: (2SR,9aSR)-9a-butyl-2,4-dimethyl-7-methoxymethoxy-1,2,9,9a-tetrahydro-3H-fluoren-3-one A 0.4M solution of lithium diisopropylamide (LDA) in tetrahydrofuran (THF) was prepared by dissolving diisopropyl amine (0.56 mL, 4 mmol) in anhydrous THF (5 mL), cooling the solution to 0° C., adding either 1.6M (2.5 mL) or 2.5M (1.6 mL) butyllithium in hexanes, diluting the resulting solution to 10.0 mL total volume with anhydrous THF, and stirring the solution for at least 30 minutes at 0° C.

A solution of 9a-butyl-7-methoxymethoxy-4-methyl-1,2, 9,9a-tetrahydro-3H-fluoren-3-one (162 mg, 0.52 mmol) in anhydrous THF (2.5 mL) was cooled in an ice bath and stirred under a nitrogen atmosphere while 0.4M LDA in THF (1.55 mL, 0.62 mmol) was added by syringe. After stirring at 0° C. for 30 minutes, the solution was cooled to −78° C. (dry ice-acetone bath) and treated with iodomethane (0.162 mL, 2.6 mmol). The resulting mixture was allowed to slowly warm to room temperature, then stirred at room temperature overnight. The mixture was diluted with EtOAc (60 mL) and shaken with saturated aqueous NH$_4$Cl (40 mL). The aqueous phase was extracted with more EtOAc (20 mL). The combined organics were washed with 5% NaHCO$_3$, water, and brine, dried over MgSO$_4$, filtered, and concentrated under vacuum to a yellow oil. The crude product was purified by preparative layer chromatography (PLC) on a 0.1×20×20 cm silica gel GF plate using 4:1 hexanes-EtOAc as developing solvent. The band at R$_f$ 0.44–0.56 was extracted with EtOAc and the extracts evaporated under vacuum to provide (2SR,9aSR)-9a-butyl-2,4-dimethyl-7-methoxymethoxy-1,2,9,9a-tetrahydro-3H-fluoren-3-one (111 mg) as an oil.

$^1$H NMR (CDCl$_3$, 500 MHz) δ 0.87 (t, CH$_3$), 1.19–1.34 (m, CH$_2$CH$_2$), 1.23 (d, 2-CH$_3$), 1.37 and 1.61 (two m, CH$_2$), 1.73 (t, 1-CHaHb), 2.08 (s, 4-CH$_3$), 2.29 (dd, 1-CHaHb), 2.56 (m, H-2), 2.69 and 2.96 (two d, 9-CH$_2$), 3.52 (s, OCH$_3$), 5.24 (m, OCH$_2$O), 6.98 (br d, H-6), 7.01 (br s, H-8), and 7.65 (d, H-5).

Step 3: (2SR,9aRS)-9a-butyl-2,4-dimethyl-7-methoxymethoxy-2-propyl-1,2,9,9a-tetrahydro-3H-fluoren-3-one A solution of (2SR,9aSR)-9a-butyl-2,4-dimethyl-7-methoxymethoxy-1,2,9,9a-tetrahydro-3H-fluoren-3-one (110 mg, 0.34 mmol) in anhydrous THF (1.5 mL) was cooled in an ice bath, stirred under a nitrogen atmosphere, and treated with 0.4M LDA in THF (1 mL, 0.4 mmol). After stirring at 0° C. for 30 minutes, the solution was cooled to −78° C. and treated with iodopropane (0.170 mL, 1.7 mmol). The resulting mixture was allowed to gradually warm to room temperature, then stirred at room temperature overnight. Workup as described in step 2 afforded a crude product (112 mg) which was purified by PLC on a 0.1×20× 20 cm silica gel GF plate, using 10:1 hexanes-EtOAc as developing solvent. The band at $R_f$ 0.20–0.27 gave recovered starting material (39 mg) and the band at $R_f$ 0.31–0.38 afforded the product (2SR,9aRS)-9a-butyl-2,4-dimethyl-7-methoxymethoxy-2-propyl-1,2,9,9a-tetrahydro-3H-fluoren-3-one (41 mg) as an oil.

$^1$H NMR (CDCl$_3$, 500 MHz) δ 0.83 (t, CH$_3$), 0.85 (t, CH$_3$), 1.00–1.54 (m, CH$_2$CH$_2$CH$_3$ and CH$_2$CH$_2$CH$_2$CH$_3$), 1.32 (s, 2-CH$_3$), 1.91 and 2.13. (two d, 1-CH$_2$), 2.11 (s, 4-CH$_3$), 2.70 and 3.00 (two d, 9-CH$_2$), 3.52 (s, OCH$_3$), 5.23 (m, OCH$_2$O), 6.97–7.01 (m, H-6 and H-8), and 7.67 (d, H-5).

Step 4: (2SR,9aRS)-9a-butyl-2,4-dimethyl-7-hydroxy-2-propyl-1,2,9,9a-tetrahydro-3H-fluoren-3-one A solution of (2SR,9aRS)-9a-butyl-2,4-dimethyl-7-methoxymethoxy-2-propyl-1,2,9,9a-tetrahydro-3H-fluoren-3-one (40 mg, 0.11 mmol) in methanol (approx. 0.5–1 mL) was placed under a nitrogen atmosphere and treated with 2N aqueous HCl (0.165 mL, 0.37 mmol). The resulting yellow solution was stirred and heated in an oil bath at 85° C. for 60 minutes. On cooling, the mixture deposited white crystals. The mixture was cooled in an ice bath and filtered. The crystalline product was washed with ice-cold 5:1 MeOH-2N HCl (2×2 mL) and dried under vacuum to afford (2SR,9aRS)-9a-butyl-2,4-dimethyl-7-hydroxy-2-propyl-1,2,9,9a-tetrahydro-3H-fluoren-3-one.

$^1$H NMR (CDCl$_3$, 500 MHz) δ 0.83 (t, CH$_3$), 0.85 (t, CH$_3$), 1.00–1.55 (m, CH$_2$CH$_2$CH$_3$ and CH$_2$CH$_2$CH$_2$CH$_3$), 1.32 (s, 2-CH$_3$), 1.92 and 2.12. (two d, 1-CH$_2$), 2.11 (s, 4-CH$_3$), 2.68 and 2.98 (two d, 9-CH$_2$), 5.26 (s, OH), 6.78–6.82 (m, H-6 and H-8), and 7.63 (m, H-5).

EXAMPLE 19

SYNTHESIS OF 9a-BUTYL-7-HYDROXY-2,2,4-TRIMETHYL-1,2,9,9a-TETRAHYDRO-3H-FLUOREN-3-ONE

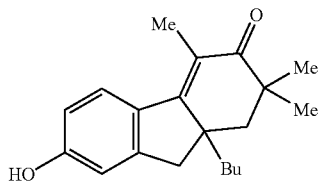

Step 1: 9a-butyl-7-methoxymethoxy-2,2,4-trimethyl-1,2,9,9a-tetrahydro-3H-fluoren-3-one A solution of (2SR,9aSR)-9a-butyl-2,4-dimethyl-7-methoxymethoxy-1,2,9,9a-tetrahydro-3H-fluoren-3-one (39 mg, 0.12 mmol) in anhydrous THF (1.0 mL) was cooled in an ice bath, stirred under a nitrogen atmosphere, and treated with 0.4M LDA in THF (0.39 mL, 0.16 mmol). After stirring at 0° C. for 30 minutes, the yellow solution was cooled to −78° C. and treated with iodomethane (0.037 mL, 0.6 mmol). The resulting mixture was allowed to gradually warm to room temperature, then stirred at room temperature overnight. Workup as described in Example 18, step 2, afforded a crude product which was purified by PLC on a 0.1×20×20 cm silica gel GF plate, using 10:1 hexanes-EtOAc as developing solvent. The band at $R_f$ 0.18–0.24 afforded 9a-butyl-7-methoxymethoxy-2,2,4-trimethyl-1,2,9, 9a-tetrahydro-3H-fluoren-3-one (28 mg) as an oil.

$^1$H NMR (CDCl$_3$, 500 MHz) δ 0.85 (t, CH$_3$), 1.15 and 1.35 (two s, two 2-CH$_3$), 1.20, 1.39 and 1.55 (three m, CH$_2$CH$_2$CH$_2$CH$_3$), 1.85 and 2.27. (two d, 1-CH$_2$), 2.12 (s, 4-CH$_3$), 2.66 and 2.99 (two d, 9-CH$_2$), 3.52 (s, OCH$_3$), 5.23 (m, OCH$_2$O), 6.97–7.01 (m, H-6 and H-8), and 7.67 (d, H-5).

Step 2: 9a-butyl-7-hydroxy-2,2,4-trimethyl-1,2,9,9a-tetrahydro-3H-fluoren-3-one

A solution of 9a-butyl-7-methoxymethoxy-2,2,4-trimethyl-1,2,9,9a-tetrahydro-3H-fluoren-3-one (28 mg, 0.08 mmol) in methanol (2 mL) was placed under a nitrogen atmosphere and treated with 2N aqueous HCl (0.12 mL, 0.24 mmol). The resulting yellow solution was stirred and heated in an oil bath at 55–80° C. for 45 minutes. After cooling to room temperature, the mixture was diluted with EtOAc (60 mL) and shaken with 5% aqueous NaHCO$_3$. The aqueous portion was separated and extracted with EtOAc (40 mL). The combined organics were washed with water and brine, dried over MgSO$_4$, filtered, and concentrated under vacuum to an oil. The crude product was purified by PLC on a 0.1×20×20 cm silica gel GF plate, developing twice with 4:1 hexanes-EtOAc. The band at $R_f$ 0.34–0.43 was eluted with EtOAc and the eluant evaporated under vacuum to a residue which was lyophilized from benzene to afford 9a-butyl-7-hydroxy-2,2,4-trimethyl-1,2,9,9a-tetrahydro-3H-fluoren-3-one as an amorphous solid.

$^1$H NMR (CDCl$_3$, 500 MHz) δ 0.84 (t, CH$_3$), 1.16 and 1.36 (two s, two 2-CH$_3$), 1.20, 1.38 and 1.55 (three m, CH$_2$CH$_2$CH$_2$CH$_3$), 1.86 and 2.26. (two d, 1-CH$_2$), 2.12 (s, 4-CH$_3$), 2.65 and 2.97 (two d, 9-CH$_2$), 5.62 (s, OH), 6.80–6.84 (m, H-6 and H-8), and 7.64 (m, H-5).

Mass Spectrum, m/e 299.1 (M+1).

EXAMPLE 20

SYNTHESIS OF (2SR,9aRS)-9a-BUTYL-7-HYDROXY-2-IODO-4-METHYL-1,2,9,9a-TETRAHYDRO-3H-FLUOREN-3-ONE

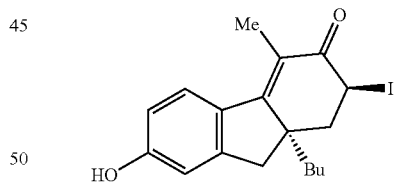

Step 1: (2SR,9aRS)-9a-butyl-2-iodo-7-methoxymethoxy-4-methyl-1,2,9,9a-tetrahydro-3H-fluoren-3-one A solution of 9a-butyl-7-methoxymethoxy-4-methyl-1,2, 9,9a-tetrahydro-3H-fluoren-3-one (134 mg, 0.43 mmol) in anhydrous THF (2.5 mL) was cooled in an ice bath, stirred under a nitrogen atmosphere, and treated with 0.4M LDA in THF (1.2 mL, 0.48 mmol). After stirring at 0° C. for 30 minutes, the enolate solution was cooled to −78° C. and treated with a solution of iodine (540 mg, 2.13 mmol) in THF. The resulting mixture was allowed to gradually warm to room temperature, then stirred at room temperature overnight. The mixture was diluted with EtOAc (50 mL), washed with 1N HCl, saturated aqueous Na$_2$SO$_3$ (2×30 mL), water, 5% NaHCO$_3$, and brine, dried over MgSO$_4$, filtered, and evaporated under vacuum to provide crude (2SR,9aRS)-9a- butyl-2-iodo-7-methoxymethoxy-4-methyl-1,2,9,9a-tetrahydro-3H-fluoren-3-one as a gum.

$^1$H NMR (CDCl$_3$, 500 MHz) δ 0.86 (t, CH$_3$), 1.17–1.32 (m, CH$_2$CH$_2$), 1.38 and 1.59 (two m, CH$_2$), 2.15 (s, 4-CH$_3$), 2.70 (t, 1-CHaHb), 2.74 and 2.95 (two d, 9-CH$_2$), 2.93 (dd, 1-CHaHb), 3.51 (s, OCH$_3$), 5.23 (m, OCH$_2$O), 5.30 (dd, H-2), 6.97–7.02 (m, H-6 and H-8), and 7.65 (d, H-5).

Step 2: (2SR,9aRS)-9a-butyl-7-hydroxy-2-iodo-4-methyl-1,2,9,9a-tetrahydro-3H-fluoren-3-one A suspension of (2SR,9aRS)-9a-butyl-2-iodo-7-methoxymethoxy-4-methyl-1,2,9,9a-tetrahydro-3H-fluoren-3-one (50 mg, 0.11 mmol) in methanol (3.5 mL) was placed under a nitrogen atmosphere, heated in an oil bath at 70° C. to affect solution, then treated with 2N aqueous HCl (0.195 mL, 0.39 mmol). The resulting solution was stirred and heated in an oil bath at 70° C. for 50 minutes. After cooling to room temperature, the mixture was diluted with EtOAc and shaken with 5% aqueous NaHCO$_3$. The aqueous portion was separated and extracted with EtOAc. The combined organics were washed with water and brine, dried over MgSO$_4$, filtered, and concentrated under vacuum to an oil. The crude product was purified by PLC on a 0.1×20×20 cm silica gel GF plate, developing twice with 5:1 hexanes-EtOAc. The band at R$_f$ 0.24–0.32 was eluted with EtOAc and the eluant evaporated under vacuum to provide (2SR,9aRS)-9a-butyl-7-hydroxy-2-iodo-4-methyl-1,2,9,9a-tetrahydro-3H-fluoren-3-one as an oil.

$^1$H NMR (CDCl$_3$, 500 MHz) δ 0.86 (t, CH$_3$), 1.16–1.32 (m, CH$_2$CH$_2$), 1.39 and 1.60 (two m, CH$_2$), 2.16 (s, 4-CH$_3$), 2.72 (t, 1-CHaHb), 2.73 and 2.93 (two d, 9-CH$_2$), 2.93 (dd, 1-CHaHb), 5.31 (dd, H-2), 5.52 (br s, OH), 6.81–6.84 (m, H-6 and H-8), and 7.63 (m, H-5).

EXAMPLE 21

SYNTHESIS OF (2SR,9aRS)-9a-BUTYL-2,7-DIHYDROXY-4-METHYL-1,2,9,9a-TETRAHYDRO-3H-FLUOREN-3-ONE

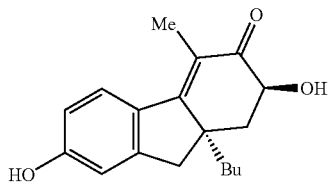

Step 1: 9a-butyl-7-methoxymethoxy-4-methyl-3-trimethylsilyloxy-9,9a-dihydro-1H-fluorene A solution of 9a-butyl-7-methoxymethoxy-4-methyl-1,2,9,9a-tetrahydro-3H-fluoren-3-one (163 mg, 0.52 mmol) in anhydrous THF (2.5 mL) was cooled in an ice bath and stirred under a nitrogen atmosphere while 0.4M LDA in THF (1.9 mL, 0.78 mmol) was added by syringe. After stirring at 0° C. for 30 minutes, the solution was cooled to −78° C. (dry ice-acetone bath) and treated with chlorotrimethylsilane (0.100 mL, 0.78 mmol). The resulting mixture was allowed to slowly warm to room temperature, then stirred at room temperature overnight. The mixture was diluted with EtOAc (60 mL) and shaken with 5% aqueous NaHCO$_3$ (30 mL). The aqueous phase was separated and extracted with more EtOAc (30 mL). The combined organics were washed with saturated brine, dried over MgSO$_4$, filtered, and concentrated under vacuum to an oil (204 mg). The $^1$H NMR of this material showed a 9:1 mixture of 9a-butyl-7-methoxymethoxy-4-methyl-3-trimethylsilyloxy-9,9a-dihydro-1H-fluorene and starting material.

$^1$H NMR (CDCl$_3$, 500 MHz) δ 0.26 (s, Si(CH$_3$)$_3$), 0.82 (t, CH$_3$), 1.04–1.40 (m, CH$_2$CH$_2$CH$_2$), 2.07 (s, 4-CH$_3$), 2.19 and 2.39 (two dd, 1-CH$_2$), 2.48 and 2.95 (two d, 9-CH$_2$), 3.52 (s, OCH$_3$), 4.95 (dd, H-2), 5.21 (m, OCH$_2$O), 6.94 (dd, H-6), 6.99 (d, H-8), and 7.56 (d, H-5).

Step 2: (2SR,9aRS)-9a-butyl-2-hydroxy-7-methoxymethoxy-4-methyl-1,2,9,9a-tetrahydro-3H-fluoren-3-one A solution of the crude trimethylsilylenolether from step 1 (204 mg, approx. 0.5 mmol) in anhydrous CH$_2$Cl$_2$ (5 mL) was treated with solid NaHCO$_3$ (42 mg, 0.5 mmol) then placed under a nitrogen atmosphere and stirred at room temperature. The mixture was treated over two minutes with three potions of 96% m-chloroperoxybenzoic acid (65, 69, and 45 mg, 1.0 mmol), purging with nitrogen after each addition. After stirring overnight at room temperature, the mixture was diluted with CH$_2$Cl$_2$ (5 mL), treated with saturated aqueous Na$_2$SO$_3$ (5 mL), and stirred at room temperature for 25 minutes. The mixture was partitioned between CH$_2$Cl$_2$ (50 mL) and water (10 mL), and the aqueous portion extracted with more CH$_2$Cl$_2$ (25 mL). The combined organics were washed with water and brine, dried over MgSO$_4$, filtered, and concentrated under vacuum to an oil (221 mg). The crude product was purified by preparative layer chromatography on two 0.1×20×20 cm silica gel GF plates using 4:1 hexanes-EtOAc as the developing solvent. The major UV visible band at R$_f$ 0.19–0.26 gave (2SR,9aRS)-9a-butyl-2-hydroxy-7-methoxymethoxy-4-methyl-1,2,9,9a-tetrahydro-3H-fluoren-3-one (73 mg) as an oil.

$^1$H NMR (CDCl$_3$, 500 MHz) δ 0.89 (t, CH$_3$), 1.22–1.40, 1.48, and 1.65 (three m, CH$_2$CH$_2$CH$_2$), 1.91 (t, 1-CHaHb), 2.14 (s, 4-CH$_3$), 2.68 (dd, 1-CHaHb), 2.74 and 2.99 (two d, 9-CH$_2$), 3.52 (s, OCH$_3$), 3.77 (d, OH), 4.35 (ddd, H-2), 5.24 (m, OCH$_2$O), 7.00 (dd, H-6), 7.03 (d, H-8), and 7.67 (d, H-5).

Step 3: (2SR,9aRS)-9a-butyl-2,7-dihydroxy-4-methyl-1,2,9,9a-tetrahydro-3H-fluoren-3-one A solution of (2SR,9aRS)-9a-butyl-2-hydroxy-7-methoxymethoxy-4-methyl-1,2,9,9a-tetrahydro-3H-fluoren-3-one (73 mg, 0.22 mmol) in methanol (5 mL) was placed under a nitrogen atmosphere, treated with 2N aqueous HCl (0.33 mL, 0.66 mmol), and stirred with heating in an oil bath at 80° C. for 30 minutes. After cooling to room temperature, the reaction mixture was diluted with EtOAc, washed with 5% aqueous NaHCO$_3$ and brine, dried over MgSO$_4$, filtered, and concentrated under vacuum to an oil. The crude product was purified by PLC on a 0.1×20×20 cm silica gel GF plate, developing twice with 4:1 hexanes-EtOAc. The band at R$_f$ 0.12–0.20 was eluted with EtOAc and the eluant evaporated under vacuum to a gum (50 mg). This material crystallized from benzene to afford (2SR,9aRS)-9a-butyl-2,7-dihydroxy-4-methyl-1,2,9,9a-tetrahydro-3H-fluoren-3-one as a white solid.

$^1$H NMR (CDCl$_3$, 500 MHz) δ 0.88 (t, CH$_3$), 1.22–1.39, 1.47, and 1.64 (three m, CH$_2$CH$_2$CH$_2$), 1.92 (t, 1-CHaHb), 2.14 (s, 4-CH$_3$), 2.68 (dd, 1-CHaHb), 2.72 and 2.97 (two d, 9-CH$_2$), 3.84 (br s, OH), 4.37 (dd, H-2), 6.80–6.84 (m, H-6 and H-8), and 7.63 (d, H-5).

EXAMPLE 22

SYNTHESIS OF (2RS,9aSR)-9a-BUTYL-7-HYDROXY-2-(2-HYDROXYETHYL)-4-METHYL-1,2,9,9a-TETRAHYDRO-3H-FLUOREN-3-ONE

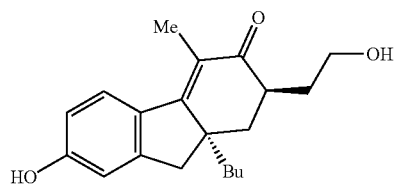

Step 1: (2SR,9aSR)-2-allyl-9a-butyl-7-methoxymethoxy-4-methyl-1,2,9,9a-tetrahydro-3H-fluoren-3-one A solution of 9a-butyl-7-methoxymethoxy-4-methyl-1,2,9,9a-tetrahydro-3H-fluoren-3-one (230 mg, 0.73 mmol) in anhydrous THF (3.8 mL) was cooled in an ice bath, stirred under a nitrogen atmosphere, and treated with freshly prepared 0.4M LDA in THF (2.2 mL, 0.88 mmol). The resulting solution was stirred at 0° C. for 30 minutes, then cooled to −78° C. (dry ice-acetone bath) and treated with allyl bromide (0.316 mL, 3.65 mmol). The reaction mixture was allowed to gradually warm to room temperature then stirred at room temperature overnight. The mixture was diluted with EtOAc (60 mL) and shaken with 1N HCl (35 mL). The aqueous phase was extracted with EtOAc (20 mL) and the combined organics were washed with 5% NaHCO$_3$ and brine, dried over MgSO$_4$, filtered, and concentrated under vacuum to a yellow oil. The crude product was purified by preparative layer chromatography on three 0.1×20×20 silica gel GF plates using 4:1 hexanes-EtOAc as developing solvent. The UV visible band at R$_f$ 0.44–0.56 was eluted with EtOAc and the eluant evaporated under vacuum to afford (2SR,9aSR)-2-allyl-9a-butyl-7-methoxymethoxy-4-methyl-1,2,9,9a-tetrahydro-3H-fluoren-3-one (193 mg) as an oil.

$^1$H NMR (CDCl$_3$, 500 MHz) δ 0.86 (t, CH$_3$), 1.18–1.29 (m, CH$_2$CH$_2$), 1.36 and 1.58 (two m, CH$_2$), 1.67 (t, 1-CHaHb), 2.09 (s, 4-CH$_3$), 2.20 and 2.51 (two m, CH$_2$CH=), 2.30 (dd, 1-CHaHb), 2.70 and 2.97 (two d, 9-CH$_2$), 2.80 (m, H-2), 3.52 (s, OCH$_3$), 5.04–5.12 (m, CH=CH$_2$), 5.23 (m, OCH$_2$O), 5.79 (m, CH=CH$_2$), 6.98 (dd, H-6), 7.01 (d, H-8), and 7.65 (d, H-5).

Step 2: (2RS,9aSR)-9a-butyl-2-(3-hydroxy-2-oxopropyl)-7-methoxymethoxy-4-methyl-1,2,9,9a-tetrahydro-3H-fluoren-3-one and (2RS,9aSR)-9a-butyl-7-methoxymethoxy-4-methyl-2-(2-oxoethyl)-1,2,9,9a-tetrahydro-3H-fluoren-3-one A solution of (2SR,9aSR)-2-allyl-9a-butyl-7-methoxymethoxy-4-methyl-1,2,9,9a-tetrahydro-3H-fluoren-3-one (170 mg, 0.48 mmol) in dioxane (9 mL) was diluted with water (3 mL) and treated with a single crystal of OsO$_4$ followed by NaIO$_4$ (125 mg, 0.58 mmol). The mixture was stirred at room temperature for 15 minutes, treated with more NaIO$_4$ (132 mg, 0.62 mmol), and stirred an additional 30 minutes at room temperature. Workup provided a gum which was purified by PLC on two 0.1× 20×20 cm silica gel GF plates, developing twice with 4:1 hexanes-EtOAc. The minor UV visible band provided (2RS, 9aSR)-9a-butyl-2-(3-hydroxy-2-oxopropyl)-7-methoxymethoxy-4-methyl-1,2,9,9a-tetrahydro-3H-fluoren-3-one (26 mg) as an oil. The major UV visible band afforded (2RS,9aSR)-9a-butyl-7-methoxymethoxy-4-methyl-2-(2-oxoethyl)-1,2,9,9a-tetrahydro-3H-fluoren-3-one (85 mg) as an oil.

$^1$H NMR (CDCl$_3$, 500 MHz) of (2RS,9aSR)-9a-butyl-7-methoxymethoxy-4-methyl-2-(2-oxoethyl)-1,2,9,9a-tetrahydro-3H-fluoren-3-one: δ 0.89 (t, CH$_3$), 1.27, 1.40 and 1.69 (three m, CH$_2$CH$_2$CH$_2$), 1.81 (t, 1-CHaHb), 2.09 (s, 4-CH$_3$), 2.33 (dd, 1-CHaHb), 2.47 and 3.06 (two ddd, CH$_2$CHO), 2.69 and 2.98 (two d, 9-CH$_2$), 3.15 (m, H-2), 3.52 (s, OCH$_3$), 5.24 (m, OCH$_2$O), 6.99 (dd, H-6), 7.02 (d, H-8), 7.66 (d, H-5), and 9.91 (t, CHO).

Step 3: (2RS,9aSR)-9a-butyl-7-hydroxy-4-methyl-2-(2-oxoethyl)-1,2,9,9a-tetrahydro-3H-fluoren-3-one A solution of (2RS,9aSR)-9a-butyl-7-methoxymethoxy-4-methyl-2-(2-oxoethyl)-1,2,9,9a-tetrahydro-3H-fluoren-3-one (85 mg) in methanol (1 mL) was diluted with 2N HCl (0.36 mL, 0.72 mmol). The resulting mixture was stirred at room temperature for 30 minutes followed by heating in an oil bath at 80° C. for 40 minutes. On cooling to room temperature, crystals formed. The mixture was diluted with EtOAc and washed with 5% NaHCO$_3$ and 1N HCl. The aqueous washes were back-extracted with EtOAc. The combined organics were washed with brine, dried over MgSO$_4$, filtered, and concentrated under vacuum. The residue was purified by PLC on a 0.1×20×20 cm silica gel GF plate, using 2:1 hexanes-EtOAc as developing solvent, to afford (2RS,9aSR)-9a-butyl-7-hydroxy-4-methyl-2-(2-oxoethyl)-1,2,9,9a-tetrahydro-3H-fluoren-3-one (50 mg).

$^1$H NMR (CDCl$_3$, 500 MHz) δ 0.89 (t, CH$_3$), 1.27, 1.41 and 1.69 (three m, CH$_2$CH$_2$CH$_2$), 1.82 (t, 1-CHaHb), 2.09 (s, 4-CH$_3$), 2.33 (dd, 1-CHaHb), 2.48 and 3.06 (two ddd, CH$_2$CHO), 2.67 and 2.96 (two d, 9-CH$_2$), 3.15 (m, H-2), 5.12 (s, OH), 6.78–6.82 (m, H-6 and H-8), 7.62 (d, H-5), and 9.91 (t, CHO).

Step 4: (2RS,9aSR)-9a-butyl-7-hydroxy-2-(2-hydroxyethyl)-4-methyl-1,2,9,9a-tetrahydro-3H-fluoren-3-one A solution of (2RS,9aSR)-9a-butyl-7-hydroxy-4-methyl-2-(2-oxo-ethyl)-1,2,9,9a-tetrahydro-3H-fluoren-3-one (17 mg, 0.05 mmol) in 2-propanol (2 mL) was treated with NaBH$_4$ (1.9 mg, 0.05 mmol) and the mixture was stirred at room temperature for 40 minutes. The solvent was evaporated under vacuum. The residue was taken up in EtOAc (60 mL), washed with 0.2N HCl (30 mL), 5% NaHCO$_3$, and brine, dried over MgSO$_4$, filtered, and concentrated under vacuum to a gum (24 mg). This material was purified by PLC on a 0.1×20×20 cm silica gel GF plate using 2:1 hexanes-EtOAc as developing solvent. The UV visible band at R$_f$ 0.06–0.11 afforded (2RS,9aSR)-9a-butyl-7-hydroxy-2-(2-hydroxyethyl)-4-methyl-1,2,9,9a-tetrahydro-3H-fluoren-3-one as an oil.

$^1$H NMR (CD$_3$OD, 500 MHz) δ 0.82 (t, CH$_3$), 1.20, 1.33 and 1.56 (three m, CH$_2$CH$_2$CH$_2$), 1.48 and 2.22 (two m, CH$_2$CH$_2$OH), 1.66 (t, 1-CHaHb), 2.01 (s, 4-CH$_3$), 2.33 (dd, 1-CHaHb), 2.61 (m, H-2), 2.64 and 2.92 (two d, 9-CH$_2$), 3.68 (m, CH$_2$CH$_2$OH), 6.73–6.78 (m, H-6 and H-8), and 7.57 (d, H-5).

EXAMPLE 23

SYNTHESIS OF (2SR,9aSR)-2-ALLYL-9a-BUTYL-7-HYDROXY-4-METHYL-1,2,9,9a-TETRAHYDRO-3H-FLUOREN-3-ONE

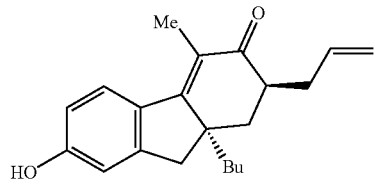

A solution of (2SR,9aSR)-2-allyl-9a-butyl-7-methoxymethoxy-4-methyl-1,2,9,9a-tetrahydro-3H-fluoren-3-one (5 mg, 0.015 mmol) in THF (0.5 mL) was treated with 6N HCl (0.5 mL) and the resulting solution was heated at 50° C. overnight. The mixture was diluted with EtOAc (30 mL), washed with 5% NaHCO$_3$ and brine, dried over MgSO$_4$, filtered, and evaporated under vacuum to a yellow oil. The crude product was purified by PLC on a 0.025×20×20 cm silica gel GF plate using 2:1 hexanes-EtOAc as developing solvent. The UV visible band at R$_f$ 0.43–0.57 afforded (2SR,9aSR)-2-allyl-9a-butyl-7-hydroxy-4-methyl-1,2,9,9a-tetrahydro-3H-fluoren-3-one as a gum.

$^1$H NMR (CDCl$_3$, 500 MHz) δ 0.85 (t, CH$_3$), 1.16–1.30 (m, CH$_2$CH$_2$), 1.36 and 1.57 (two m, CH$_2$), 1.68 (t, 1-CHaHb), 2.09 (s, 4-CH$_3$), 2.22 and 2.53 (two m, CH$_2$CH=), 2.29 (dd, 1-CHaHb), 2.69 and 2.95 (two d, 9-CH$_2$), 2.80 (m, H-2), 5.04–5.12 (m, CH=CH$_2$), 5.40 (s, OH), 5.79 (m, CH=CH$_2$), 6.78–6.83 (m, H-6 and H-8), and 7.62 (d, H-5).

EXAMPLE 24

SYNTHESIS OF (2RS,9aSR)-9a-BUTYL-7-HYDROXY-2-(3-HYDROXY-2-OXOPROPYL)-4-METHYL-1,2,9,9a-TETRAHYDRO-3H-FLUOREN-3-ONE

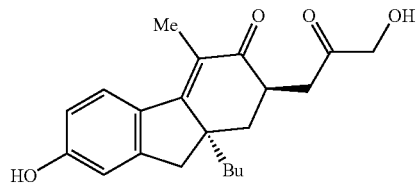

A solution of (2RS,9aSR)-9a-butyl-2-(3-hydroxy-2-oxopropyl)-7-methoxymethoxy-4-methyl-1,2,9,9a-tetrahydro-3H-fluoren-3-one (24 mg, 0.06 mmol) in methanol (1 mL) was treated with 2N HCl (0.36 mL, 0.18 mmol) and the resulting solution was heated at reflux for 20 minutes. After cooling, the mixture was concentrated under vacuum to a residue that was dissolved in EtOAc (60 mL) and washed with 5% NaHCO$_3$ (30 mL). The aqueous phase was back-extracted with EtOAc (30 mL). The combined organics were washed with brine, dried over MgSO$_4$, filtered, and evaporated under vacuum. The residue was purified by PLC, using 1:1 hexanes-EtOAc as developing solvent, to afford (2RS,9aSR)-9a-butyl-7-hydroxy-2-(3-hydroxy-2-oxopropyl)-4-methyl-1,2,9,9a-tetrahydro-3H-fluoren-3-one as an oil.

$^1$H NMR (CDCl$_3$, 500 MHz) δ 0.88 (t, CH$_3$), 1.26, 1.40 and 1.70 (three m, CH$_2$CH$_2$CH$_2$), 1.84 (t, 1-CHaHb), 2.06 (s, 4-CH$_3$), 2.30 (dd, 1-CHaHb), 2.37 and 2.97 (two dd, CH$_2$COCH$_2$OH), 2.65 and 2.96 (two d, 9-CH$_2$), 3.22 (t, CH$_2$COCH$_2$OH), 3.27 (m, H-2), 4.29 and 4.48 (two dd, CH$_2$COCH$_2$OH), 6.03 (s, OH), 6.79–6.83 (m, H-6 and H-8), and 7.61 (d, H-5).

EXAMPLE 25

SYNTHESIS OF (9SR,9aSR)-7-HYDROXY-4-METHYL-9-PROPYL-1,2,9,9a-TETRAHYDRO-3H-FLUOREN-3-ONE

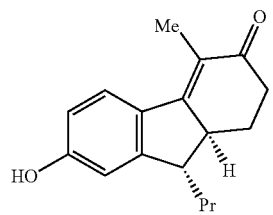

Step 1: 6-methoxy-1-propyl-1H-indene

A solution of 5-methoxy-1H-indene (0.895 g, 6.12 mmol) in anhydrous Et$_2$O (7.5 mL) was treated with 1.4M MeLi in Et$_2$O (4.7 mL, 6.58 mmol) added dropwise over 10 minutes. The resulting hazy solution was stirred at room temperature an additional 15 minutes, then cooled in an ice bath and treated with iodopropane (1.00 mL, 10.3 mmol). The mixture was stirred at ice bath temperature with gradual warming to room temperature. After stirring at room temperature overnight, the mixture was treated with saturated aq. NH$_4$Cl (10 mL) and Et$_2$O (15 mL) and shaken. The organic phase was washed with brine, dried over MgSO$_4$, filtered, and evaporated under vacuum to afford a mixture (1.248 g) of 5-methoxy-1-propyl-1H-indene and 6-methoxy-1-propyl-1H-indene as an oil.

Step 2: 6-methoxy-1-propyl-indan

The mixture of indenes from step 1 (1.24 g, approx. 6.1 mmol) was dissolved in ethanol (40 mL), treated with 10% Pd on carbon (58 mg), and hydrogenated at 40 psi and room temperature for 60 minutes. The catalyst was removed by filtration and the filtrate was evaporated under vacuum to provide a mixture (1.287 g) of 6-methoxy-1-propyl-indan and 5-methoxy-1-propyl-indan in nearly a 1:1 ratio.

Step 3: 5-methoxy-3-propyl-1-indanone

The mixture of indans from step 2 (1.287 g, approx. 6.1 mmol) in CH$_2$Cl$_2$ (50 mL) was treated with a finely ground mixture of KMnO$_4$ (7.00 g) and CuSO$_4$.xH$_2$O. The resulting mixture was heated at reflux for 89 hours, then cooled to room temperature and filtered through a celite pad. The filtrate was dried over MgSO$_4$, filtered and evaporated under vacuum to an oil (1.155 g). The crude product was purified by chromatography on a Biotage FLASH 12M column, eluting with 10% EtOAc in hexanes, to afford 5-methoxy-3-propyl-1-indanone (0.188 g) as an oil. Other column fractions afforded 6-methoxy-3-propyl-1-indanone, the indan starting materials, and 5-methoxy-1-indanone.

$^1$H NMR (CDCl$_3$, 400 MHz) δ 0.99 (t, CH$_3$), 1.38–1.54 (m, CHaHbCH$_2$), 1.89 (m, CHaHb), 2.36 and 2.85 (two dd, 2-CH$_2$), 3.31 (m, H-3), 3.91 (s, OCH$_3$), 6.90–6.94 (m, H-4 and H-6), and 7.69 (m, H-7).

Step 4: 2-[2-(2-ethyl-[1,3]dioxolan-2-yl)-ethyl]-5-methoxy-3-propyl-1-indanone

A mixture of 5-methoxy-3-propyl-1-indanone (184 mg, 0.90 mmol) and (2-ethyl-[1,3]dioxolan-2-yl)acetaldehyde (173 mg, 1.20 mmol) was treated with a solution of KOH (85% wt. pure, 20 mg, 0.30 mmol) in ethanol (1.0 mL). The resulting mixture was stirred at room temperature for 30 minutes, then treated with 10% Pd on carbon (9 mg), placed under a hydrogen atmosphere, and stirred vigorously at room temperature for 18 hours. The mixture was acidified with 2N HCl and partitioned between EtOAc (9 mL) and water (5 mL). The organic phase was washed with brine, dried over MgSO$_4$, filtered, and evaporated under vacuum to an oil (316 mg). The crude product was purified by chromatography on a Biotage FLASH 12M column, eluting with 10% EtOAc in hexanes, to afford 2-[2-(2-ethyl-[1,3] dioxolan-2-yl)-ethyl]-5-methoxy-3-propyl-1-indanone (87 mg) as an oil.

$^1$H NMR (CDCl$_3$, 500 MHz) δ 0.91 (t, CH$_3$), 0.97 (t, CH$_3$), 1.32–1.50 (m, CH$_2$), 1.53–1.90 (m, four CH$_2$), 2.35 (m, H-2), 2.99 (m, H-3), 3.91 (s, OCH$_3$), 3.93 (s, OCH$_2$CH$_2$O), 6.89–6.93 (m, H-4 and H-6), and 7.66 (d, H-7)

Step 5: (9SR,9aSR)-7-methoxy-4-methyl-9-propyl-1,2,9,9a-tetrahydro-3H-fluoren-3-one A solution of 2-[2-(2-ethyl-[1,3]dioxolan-2-yl)-ethyl]-5-methoxy-3-propyl-1-indanone (86 mg, 0.26 mmol) in acetic acid (1.5 mL) was diluted with 6N HCl (1.5 mL) and the resulting mixture was heated in an oil bath at 125° C. for 4.5 hours. After cooling, the mixture was evaporated under high vacuum to an oil which was partitioned between EtOAc and saturated aq. NaHCO$_3$. The organic phase was washed with brine, dried over MgSO$_4$, filtered, and evaporated under vacuum to a gum (65 mg). The crude product was purified by flash chromatography on EM silica gel 60 (230–400 mesh, 1×16 cm column), eluting with 15% EtOAc in hexanes. The product containing fractions were concentrated under vacuum to afford (9SR,9aSR)-7-methoxy-4-methyl-9-propyl-1,2,9,9a-tetrahydro-3H-fluoren-3-one (40 mg) as an oil.

$^1$H NMR (CDCl$_3$, 500 MHz) δ 1.03 (t, CH$_2$CH$_2$CH$_3$), 1.53 (m, CH$_2$CH$_2$CH$_3$), 1.66 and 1.97 (two m, CH$_2$CH$_2$CH$_3$), 1.85 and 2.35 (two m, 1-CH$_2$), 2.11 (d, 4-CH$_3$), 2.45 and 2.65 (two m, 2-CH$_2$), 2.79 (m, H-9a), 2.88 (m, H-9), 3.88 (s, OCH$_3$), 6.86–6.90 (m, H-6 and H-8), and 7.67 (m, H-5)

Step 6: (9SR,9aSR)-7-hydroxy-4-methyl-9-propyl-1,2,9,9a-tetrahydro-3H-fluoren-3-one A solution of (9SR,9aSR)-7-methoxy-4-methyl-9-propyl-1,2,9,9a-tetrahydro-3H-fluoren-3-one (38.3 mg, 0.142 mmol) in anhydrous CH$_2$Cl$_2$ (1.1 mL) was placed under a nitrogen atmosphere, cooled in a dry ice-acetone bath, and stirred while 1M BBr$_3$ in CH$_2$Cl$_2$ (0.354 mL, 0.345 mmol) was added by syringe. The cooling bath was removed and the reaction mixture was stirred at room temperature for 2.6 hours, then diluted with 0.2N HCl (5 mL) and EtOAc (10 mL) and shaken. The organic phase was separated, washed with brine, dried over MgSO$_4$, filtered, and evaporated under vacuum to a solid (35.2 mg). The crude product was purified by flash chromatography on EM silica gel 60 (230–400 mesh, 1×18 cm column) using 3:1 hexanes-EtOAc as eluting solvent, collecting 3 mL fractions. Fractions 12–26 were combined and concentrated under vacuum to approximately 1 mL of a suspension. The suspension was filtered and the solid portion washed with EtOAc and dried under vacuum to afford (9SR,9aSR)-7-hydroxy-4-methyl-9-propyl-1,2,9,9a-tetrahydro-3H-fluoren-3-one.

$^1$H NMR (3:1 CDCl$_3$-CD$_3$CN, 500 MHz) δ 0.93 (t, CH$_2$CH$_2$CH$_3$), 1.43 (m, CH$_2$CH$_2$CH$_3$), 1.55 and 1.85 (two m, CH$_2$CH$_2$CH$_3$), 1.75 and 2.25 (two m, 1-CH$_2$), 1.99 (d, 4-CH$_3$), 2.35 and 2.52 (two m, 2-CH$_2$), 2.68 (m, H-9a), 2.76 (m, H-9), 6.70–6.75 (m, H-6 and H-8), 7.15 (s, OH), and 7.51 (d, H-5)

IR (KBr) 3168, 2957, 1631, 1580, 1475, 1372, 1358, 1337, 1267, 1237, 1202, 1118, 1088, 866, 821, and 707 cm$^{-1}$.

Mass spectrum, m/e 257.1 (M+1).

EXAMPLE 26

SYNTHESIS OF 9a-BUTYL-8-CHLORO-7-HYDROXY-4-(TRIFLUOROMETHYL)-1,2,9,9a-TETRAHYDRO-3H-FLUOREN-3-ONE

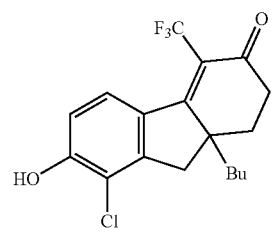

Step 1: 9a-butyl-8-chloro-7-methoxy-1,2,9,9a-tetrahydro-3H-fluoren-3-one

A solution 2-butyl-4-chloro-5-methoxy-1-indanone (550 mg, 2.03 mmol) in tetrahydrofuran (4.06 mL) was treated with methyl vinyl ketone (0.203 mL, 2.44 mmol) and 0.5N sodium methoxide in methanol (0.812 mL, 0.406 mmol). The mixture was stirred at room temperature for 90 minutes to effect conversion to 2-butyl-4-chloro-5-methoxy-2-(3-oxobutyl)-1-indanone. The reaction mixture was evaporated under vacuum. The residue in toluene (10 mL) was treated with pyrrolidine (0.170 mL, 2.03 mmol) and acetic acid (0.140 mmol, 2.44 mmol). The resulting mixture was stirred and heated in an oil bath at 80° C. for 2.5 hours. After cooling to room temperature, the mixture was partitioned between EtOAc and water. The organic phase was washed with 0.1N HCl, saturated aqueous NaHCO$_3$ and brine, dried over MgSO$_4$, filtered, and evaporated under vacuum. The residue was purified by preparative layer chromatography on silica gel GF plates to afford 9a-butyl-8-chloro-7-methoxy-1,2,9,9a-tetrahydro-3H-fluoren-3-one.

Step 2: 4-bromo-9a-butyl-8-chloro-7-methoxy-1,2,9,9a-tetrahydro-3H-fluoren-3-one A solution of 9a-butyl-8-chloro-7-methoxy-1,2,9,9a-tetrahydro-3H-fluoren-3-one (555 mg, 1.82 mmol) in anhydrous dichloromethane (18.2 mL) was treated with sodium bicarbonate (765 mg, 9.1 mmol) and bromine (0.093 mL, 1.82 mmol). The mixture was stirred at room temperature for 30 minutes and then diluted with CH$_2$Cl$_2$ (50 mL) and washed with water (50 mL). The organic phase was dried over MgSO$_4$, filtered through a pad of silica gel (10 mL) with a 10 mL CH$_2$Cl$_2$ rinse, and the solvent evaporated under vacuum. The residue (0.55 g) was lyophilized from benzene to afford 4-bromo-9a-butyl-8-chloro-7-methoxy-1,2,9,9a-tetrahydro-3H-fluoren-3-one as an amorphous solid.

Step 3: 9a-butyl-8-chloro-7-methoxy-4-(trifluoromethyl)-1,2,9,9a-tetrahydro-3H-fluoren-3-one A mixture of 4-bromo-9a-butyl-8-chloro-7-methoxy-1,2,9,9a-tetrahydro-3H-fluoren-3-one (55 mg, 0.143 mmol), copper(I) iodide (32.7 mg, 0.172 mmol), methyl difluoro (fluorosulfonyl)acetate (0.132 mL, 1.04 mmol), and anhydrous N,N-dimethylformamide (6.7 mL) was placed under a nitrogen atmosphere, stirred, and heated in an oil bath at 75° C. for 4 days. After cooling to room temperature, the mixture was filtered. The filtrate was diluted with EtOAc (100 mL), washed with water (6×100 mL) and brine (50 mL), dried over MgSO$_4$, filtered, and evaporated under vacuum to an oil (48 mg). The crude product was purified by preparative layer chromatography on a 0.1×20×20 cm silica gel GF plate, developing with CH₂Cl₂. The product band was eluted with EtOAc and the eluent evaporated under vacuum to afford 9a-butyl-8-chloro-7-methoxy-4-(trifluoromethyl)-1,2,9,9a-tetrahydro-3H-fluoren-3-one (32 mg) as an oil.

Step 4: 9a-butyl-8-chloro-7-hydroxy-4-(trifluoromethyl)-1,2,9,9a-tetrahydro-3H-fluoren-3-one A solution of 9a-butyl-8-chloro-7-methoxy-4-(trifluoromethyl)-1,2,9,9a-tetrahydro-3H-fluoren-3-one (32 mg, 0.086 mmol) in anhydrous dichloromethane (0.86 mL) was cooled in a dry ice-acetone bath (−78° C.) and the solution was treated with 1M boron tribromide in dichloromethane (0.258 mL, 0.258 mmol). The cooling bath was removed and the mixture was stirred at room temperature for 95 minutes. Additional 1M BBr₃ in CH₂Cl₂ (0.5 mL, 0.5 mmol) was added and the mixture was stirred at room temperature for an additional 100 minutes. The mixture was partitioned between EtOAc (20 mL) and water (20 mL) containing 2N HCl (3 mL). The organic phase was washed with brine (10 mL), dried over MgSO₄, filtered, and evaporated under vacuum. The oily residue was purified by preparative layer chromatography on a 0.1×20×20 cm silica gel GF plate, developing with 5% EtOAc in CH₂Cl₂. The product band was eluted with EtOAc, the eluent evaporated under vacuum, and the residue lyophilized from benzene to afford 9a-butyl-8-chloro-7-hydroxy-4-(trifluoromethyl)-1,2,9,9a-tetrahydro-3H-fluoren-3-one as an amorphous solid.

$^1$H NMR (CDCl₃, 500 MHz) δ 0.84 (t, CH₂CH₂CH₂CH₃), 1.14–1.28 (m, CH₂CH₂CH₂CH₃), 1.32 and 1.54 (two m, CH₂CH₂CH₂CH₃), 2.07 and 2.25 (two ddd, 1-CH₂), 2.50–2.63 (m, 2-CH₂), 2.80 and 3.09 (two d, 9-CH₂), 5.94 (s, OH), 7.01 (d, H-6), and 7.69 (qd, H-5).

EXAMPLE 27

SYNTHESIS OF 4-ACETYL-9a-BUTYL-8-CHLORO-7-HYDROXY-1,2,9,9a-TETRAHYDRO-3H-FLUOREN-3-ONE

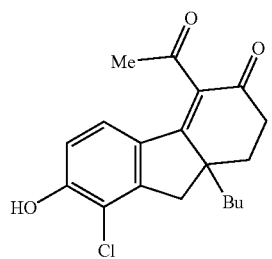

Step 1: 9a-butyl-8-chloro-4-(1-ethoxyvinyl)-7-methoxy-1,2,9,9a-tetrahydro-3H-fluoren-3-one A solution of 4-bromo-9a-butyl-8-chloro-7-methoxy-1,2,9,9a-tetrahydro-3H-fluoren-3-one (90 mg, 0.235 mmol) in anhydrous toluene (1.2 mL) was treated with tributyl(1-ethoxyvinyl)stannane (0.111 mL, 0.352 mmol) and bis(triphenylphosphine)palladium(II) chloride (33 mg, 0.047 mmol). The mixture was placed under a nitrogen atmosphere, stirred, and heated in an oil bath at 100° C. for 3 hours. After cooling to room temperature, the mixture was purified by preparative layer chromatography on two 0.1×20×20 cm silica gel GF plates, developing with 5% EtOAc in CH₂Cl₂. The product band was eluted with EtOAc and the eluent evaporated under vacuum to afford 9a-butyl-8-chloro-4-(1-ethoxyvinyl)-7-methoxy-1,2,9,9a-tetrahydro-3H-fluoren-3-one (67 mg) as an oil.

Step 2: 4-acetyl-9a-butyl-8-chloro-7-methoxy-1,2,9,9a-tetrahydro-3H-fluoren-3-one The product from step 1 in ethanol (1.0 mL), water (0.2 mL) and aqueous 2N HCl (0.2 mL) was stirred and heated in an oil bath at 80° C. for 40 minutes. After cooling, the mixture was partitioned between EtOAc (20 mL) and water (20 mL). The organic phase was washed with brine (20 mL), dried over MgSO₄, filtered, and evaporated under vacuum to provide 4-acetyl-9a-butyl-8-chloro-7-methoxy-1,2,9,9a-tetrahydro-3H-fluoren-3-one (54 mg) as an oil.

Step 3: 4-acetyl-9a-butyl-8-chloro-7-hydroxy-1,2,9,9a-tetrahydro-3H-fluoren-3-one A mixture of 4-acetyl-9a-butyl-8-chloro-7-methoxy-1,2,9,9a-tetrahydro-3H-fluoren-3-one (54 mg) and pyridine hydrochloride (3.5 g) was heated in an oil bath at 200° C. for one hour. After cooling to room temperature, the mixture was partitioned between EtOAc (50 mL) and water (50 mL). The organic phase was washed with brine (20 mL), dried over MgSO₄, filtered, and evaporated under vacuum to an oil (32 mg). The crude product was purified by preparative layer chromatography on a 0.1×20×20 cm silica gel GF plate, developing with 5% MeOH in CH₂Cl₂. The product band was eluted with 10% MeOH in CH₂Cl₂, the eluant evaporated under vacuum, and the residue lyophilized from benzene to afford 4-acetyl-9a-butyl-8-chloro-7-hydroxy-1,2,9,9a-tetrahydro-3H-fluoren-3-one as an amorphous solid.

$^1$H NMR (CDCl₃, 500 MHz) δ 0.86 (t, CH₂CH₂CH₂CH₃), 1.18–1.31 (m, CH₂CH₂CH₂CH₃), 1.45 and 1.66 (two m, CH₂CH₂CH₂CH₃), 2.06 and 2.31 (two ddd, 1-CH₂), 2.38 (s, COCH₃), 2.51 and 2.57 (two ddd, 2-CH₂), 2.72 and 3.09 (two d, 9-CH₂), 5.84 (s, OH), 6.92 (d, H-6), and 7.35 (d, H-5); mass spectrum m/z 333.2 (M+1).

EXAMPLE 28

SYNTHESIS OF 9a-BUTYL-8-CHLORO-4-CYANO-7-HYDROXY-1,2,9,9a-TETRAHYDRO-3H-FLUOREN-3-ONE

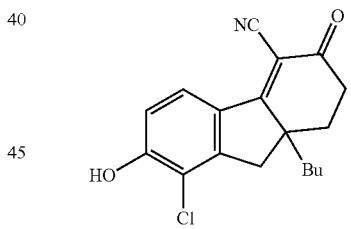

Step 1: 9a-butyl-8-chloro-4-cyano-7-methoxy-1,2,9,9a-tetrahydro-3H-fluoren-3-one A solution of 4-bromo-9a-butyl-8-chloro-7-methoxy-1,2,9,9a-tetrahydro-3H-fluoren-3-one (103 mg, 0.268 mmol) in anhydrous 1-methyl-2-pyrrolidinone (0.54 mL) was treated with copper(I) cyanide (24 mg, 0.268 mmol). The mixture was placed under a nitrogen atmosphere, stirred, and heated in an oil bath at 150° C. for 1.5 hours. After cooling to room temperature, the mixture was partitioned between EtOAc (50 mL) and water (50 mL). The organic phase was washed with water (5×50 mL) and brine (50 mL), dried over MgSO₄, filtered, and evaporated under vacuum to an oil. The crude product was purified by preparative layer chromatography on a 0.1×20×20 cm silica gel GF plate, developing with 5% EtOAc in CH₂Cl₂. The product band was eluted with EtOAc and the eluent evaporated under vacuum to afford 9a-butyl-8-chloro-4-cyano-7-methoxy-1,2,9,9a-tetrahydro-3H-fluoren-3-one (65 mg) as an oil.

Step 2: 9a-butyl-8-chloro-4-cyano-7-hydroxy-1,2,9,9a-tetrahydro-3H-fluoren-3-one A mixture of 9a-butyl-8-chloro-4-cyano-7-methoxy-1,2,9,9a-tetrahydro-3H-fluoren-3-one (65 mg) and pyridine hydrochloride (4.2 g) was heated in an oil bath at 200° C. for 85 minutes. After cooling to room temperature, the mixture was partitioned between EtOAc (50 mL) and water (50 mL). The organic phase was washed with brine (20 mL), dried over MgSO$_4$, filtered, and evaporated under vacuum. The residue was purified by preparative layer chromatography on two 0.1×20×20 cm silica gel GF plates, developing with 5% MeOH in CH$_2$Cl$_2$. The product bands were eluted with 10% MeOH in CH$_2$Cl$_2$, the eluant evaporated under vacuum, and the residue lyophilized from benzene (3 mL) plus EtOH (0.1 mL) to afford 9a-butyl-8-chloro-4-cyano-7-hydroxy-1,2,9,9a-tetrahydro-3H-fluoren-3-one as an amorphous yellow solid.

$^1$H NMR (CDCl$_3$, 500 MHz) δ 0.87 (t, CH$_2$CH$_2$CH$_2$CH$_3$), 1.15–1.33 (m, CH$_2$CH$_2$CH$_2$CH$_3$), 1.45 and 1.66 (two m, CH$_2$CH$_2$CH$_2$CH$_3$), 2.03 and 2.35 (two ddd, 1-CH$_2$), 2.56–2.65(m, 2-CH$_2$), 2.76 and 3.14 (two d, 9-CH$_2$), 6.11 (s, OH), 7.11 (d, H-6), and 8.26 (d, H-5); mass spectrum m/z 316.1 (M+1).

EXAMPLE 29

SYNTHESIS OF 9a-BUTYL-4-ETHYL-6-FLUORO-7-HYDROXY-8-METHYL-1,2,9,9a-TETRAHYDRO-3H-FLUOREN-3-ONE

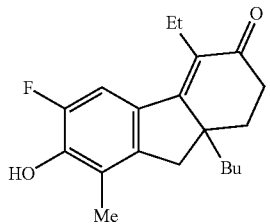

Step 1: 1-(3-fluoro-4-methoxyphenyl)-1-hexanone

Aluminum chloride (6.5 g, 48.8 mmol) was added to a stirred mixture of 1-fluoro-2-methoxybenzene (5.0 mL, 44.4 mmol) and hexanoyl chloride (7.5 mL, 53.3 mmol) at room temperature. The mixture warmed and HCl evolution occurred. The resulting mixture was stirred at room temperature for 45 minutes and then partitioned between EtOAc (100 mL) and water (100 mL). The EtOAc layer was washed with water (100 mL), aqueous K$_2$CO$_3$ (100 mL) and brine (50 mL), dried over MgSO$_4$, filtered, and evaporated under vacuum to yield crude 1-(3-fluoro-4-methoxyphenyl)-1-hexanone (9 g) as a solid.

Step 2: 2-butyl-6-fluoro-5-methoxy-1-indanone

A mixture of the crude 1-(3-fluoro-4-methoxyphenyl)-1-hexanone from step 1, methanol (45 mL), 37% aqueous formaldehyde (4.0 mL, 53.3 mmol), and potassium carbonate (6.1 g, 44.4 mmol) was stirred and heated in an oil bath at 50° C. for 40 minutes. The mixture was then stirred at room temperature overnight (20.5 hours), reheated to 50° C. for one hour, and then cooled to room temperature. The mixture was evaporated under vacuum and the residue partitioned between EtOAc (100 mL) and water (100 mL). The organic phase was washed with brine (100 mL), dried over MgSO$_4$, filtered, and evaporated under vacuum to an oil (ca. 11 g) consisting of predominantly 1-(3-fluoro-4-methoxyphenyl)-2-(methoxymethyl)-1-hexanone.

The oil was cooled in an ice bath and treated with ice cold sulfuric acid (40 mL). The cooling bath was removed and the mixture was stirred at room temperature for 10 minutes and then heated in an oil bath at 50° C. for 16.3 hours. After cooling to room temperature, the mixture was partitioned between EtOAc (200 mL) and ice-water (200 mL). The organic phase was washed with brine (100 mL), dried over MgSO$_4$, filtered, and evaporated under vacuum to a brown oil (8.8 g). The crude product was purified by chromatography on EM silica gel 60 (4.5×21 cm column), eluting with CH$_2$Cl$_2$ (200 mL forerun followed by 8 mL fractions). Fractions 8–32 were combined and evaporated under vacuum to afford 2-butyl-6-fluoro-5-methoxy-1-indanone (6.55 g) as an oil.

Step 3: 2-butyl-6-fluoro-5-hydroxy-1-indanone

A mixture of 2-butyl-6-fluoro-5-methoxy-1-indanone (2.0 g) and pyridine hydrochloride (15.0 g) was heated in an oil bath at 200° C. for 75 minutes. After cooling to room temperature, the mixture was partitioned between EtOAc (100 mL) and water (75 mL) containing brine (25 mL). The organic phase was washed with brine (50 mL), dried over MgSO$_4$, filtered, and evaporated under vacuum to provide 2-butyl-6-fluoro-5-hydroxy-1-indanone (1.79 g) as a solid.

Step 4: 4-bromo-2-butyl-6-fluoro-5-hydroxy-1-indanone

N-Bromosuccinimide (1.41 g, 7.93 mmol) was added to a solution of 2-butyl-6-fluoro-5-hydroxy-1-indanone (1.76 g, 7.93 mmol) in anhydrous N,N-dimethylformamide (15 mL). The resulting solution was stirred at room temperature for two hours. The solvent was evaporated under vacuum and the residue was partitioned between EtOAc (100 mL) and water (100 ml). The organic phase was washed with water (4×100 mL) and brine (50 mL), dried over MgSO$_4$, filtered, and evaporated under vacuum to provide crude 4-bromo-2-butyl-6-fluoro-5-hydroxy-1-indanone (2.17 g) as an oil.

Step 5: 4-bromo-2-butyl-6-fluoro-5-methoxy-1-indanone

A mixture of 4-bromo-2-butyl-6-fluoro-5-hydroxy-1-indanone (2.17 g, 7.23 mmol), N,N-dimethylformamide (14.5 mL), methyl iodide (0.675 mL, 10.84 mmol), and sodium bicarbonate (1.50 g, 18.1 mmol) was stirred at room temperature for 17 hours. The solvent was evaporated under vacuum. The residue in EtOAc (150 mL) was washed with water (5×100 mL) and brine (50 mL), dried over MgSO$_4$, filtered, and evaporated under vacuum to an oil (2.29 g). The crude product was dissolved in CH$_2$CL$_2$ (5 mL) and the solution filtered through a pad of EM silica gel 60 (20 mL) using an additional 60 mL of CH$_2$Cl$_2$ to elute the silica gel. The CH$_2$Cl$_2$ filtrate was evaporated under vacuum to afford 4-bromo-2-butyl-6-fluoro-5-methoxy-1-indanone (1.86 g) as a pink oil.

Step 6: 2-butyl-6-fluoro-5-methoxy-4-methyl-1-indanone

A mixture of 4-bromo-2-butyl-6-fluoro-5-methoxy-1-indanone (1.86 g, 5.94 mmol), bis(triphenylphosphine)palladium(II) chloride (208 mg, 0.297 mmol), tetramethyltin (0.989 mL, 7.128 mmol), triphenylphosphine (156 mg, 0.594 mmol), lithium chloride (504 mg, 11.88 mmol), and anhydrous N,N-dimethyl-formamide (11.9 mL) was placed under a nitrogen atmosphere, stirred, and heated in an oil bath at 100° C. for 22 hours. After cooling to room temperature, the mixture was evaporated under vacuum. The residue in EtOAc (150 mL) was washed with water (4×100 mL) and brine (50 mL), dried over MgSO$_4$, filtered, and evaporated under vacuum to an oil (2.15 g). The crude product was purified by chromatography on EM silica gel 60 (2.5×29 cm column), eluting with CH$_2$Cl$_2$ (50 mL fore-run followed by 8 mL fractions). Fractions 20–28 were combined and evaporated under vacuum to provide 2-butyl-6-fluoro-5-methoxy-4-methyl-1-indanone (365 mg) as an oil.

Step 7: 9a-butyl-4-ethyl-6-fluoro-7-methoxy-8-methyl-12,9, 9a-tetrahydro-3H-fluoren-3-one A solution of 2-butyl-6-fluoro-5-methoxy-4-methyl-1-indanone (118 mg, 0.47 mmol) in anhydrous tetrahydrofuran (0.47 mL) was treated with propyl vinyl ketone (0.065 mL, 0.56 mmol) and 1,8-diazabicyclo[5.4.0]undec-7-ene (0.0143 mL, 0.094 mmol). The mixture was stirred and heated in an oil bath at 50° C. for 6 hours and then at room temperature for 64 hours. The solvent was evaporated under vacuum to give a residue consisting mainly of 2-butyl-6-fluoro-5-methoxy-4-methyl-2-(3-oxohexyl)-1-indanone. This material was dissolved in acetic acid (2 mL), treated with aqueous 6N HCl (1.5 mL), and stirred while heating in an 80° C. oil bath for 6 hours. After cooling, the mixture was partitioned between EtOAc (25 mL) and saturated aqueous $K_2CO_3$ (25 mL). The organic phase was washed with brine (10 mL), dried over $MgSO_4$, filtered, and evaporated under vacuum to an oil (138 mg). The crude product was purified by preparative layer chromatography on two 0.1×20×20 cm silica gel GF plates, developing with $CH_2Cl_2$. The product bands were eluted with EtOAc and the eluent evaporated under vacuum to afford 9a-butyl-4-ethyl-6-fluoro-7-methoxy-8-methyl-1,2,9,9a-tetrahydro-3H-fluoren-3-one (93 mg) as an oil.

Step 8: 9a-butyl-4-ethyl-6-fluoro-7-hydroxy-8-methyl-1,2, 9,9a-tetrahydro-3H-fluoren-3-one A solution of 9a-butyl-4-ethyl-6-fluoro-7-methoxy-8-methyl-1,2,9,9a-tetrahydro-3H-fluoren-3-one (93 mg, 0.28 mmol) in anhydrous dichloromethane (1.4 mL) was cooled in a dry ice-acetone bath (−78° C.) and the solution treated with 1M boron tribromide in dichloromethane (1.4 mL, 1.4 mmol). The cooling bath was removed and the mixture was stirred at room temperature for 90 minutes. The mixture was partitioned between EtOAc (20 mL) and water (20 mL) containing 2N HCl (2 mL). The organic phase was washed with brine (10 mL), dried over $MgSO_4$, filtered, and evaporated under vacuum. The residue was purified by preparative layer chromatography on two 0.05×20×20 cm silica gel GF plates, developing with 5% EtOAc in $CH_2Cl_2$. The product bands were eluted with EtOAc, the eluent evaporated under vacuum, and the residue lyophilized from benzene to afford 9a-butyl-4-ethyl-6-fluoro-7-hydroxy-8-methyl-1,2,9,9a-tetrahydro-3H-fluoren-3-one as an amorphous solid.

$^1$H NMR (CDCl$_3$, 500 MHz) δ 0.84 (t, CH$_2$CH$_2$CH$_2$CH$_3$), 1.09 (t, CH$_2$CH$_3$), 1.13–1.27 (m, CH$_2$CH$_2$CH$_2$CH$_3$), 1.38 and 1.55 (two m, CH$_2$CH$_2$CH$_2$CH$_3$), 1.95 and 2.22 (two ddd, 1-CH$_2$), 2.21 (s, 8-CH$_3$), 2.39–2.67 (m, CH$_2$CH$_3$ and 2-CH$_2$), 2.54 and 2.89 (two d, 9-CH$_2$), 5.72 (two d, OH), and 7.27 (d, H-5); mass spectrum m/z 317.3 (M+1).

EXAMPLE 30

SYNTHESIS OF 9a-BUTYL-8-CHLORO-6-FLUORO-7-HYDROXY-4-METHYL-1,2,9,9a-TETRAHYDRO-3H-FLUOREN-3-ONE

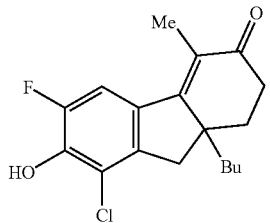

Step 1: 1-(3-chloro-5-fluoro-4-methoxyphenyl)-1-hexanone

Aluminum chloride (1.16 g, 8.72 mmol) was added to a stirred mixture of 1-chloro-3-fluoro-2-methoxybenzene (1.00 mL, 8.72 mmol) and hexanoyl chloride (1.47 mL, 10.46 mmol) at room temperature. The mixture warmed and HCl evolution occurred. The resulting mixture was stirred at room temperature for 67 hours and then partitioned between EtOAc (40 mL) and ice cold water (40 mL). The EtOAc layer was washed with brine (30 mL), dried over $MgSO_4$, filtered, and evaporated under vacuum to yield crude 1-(3-chloro-5-fluoro-4-methoxyphenyl)-1-hexanone as an oil.

Step 2: 2-butyl-4-chloro-6-fluoro-5-methoxy-1-indanone

A mixture of the crude 1-(3-chloro-5-fluoro-4-methoxyphenyl)-1-hexanone from step 1, methanol (8.7 mL), 37% aqueous formaldehyde (0.786 mL, 10.5 mmol), and potassium carbonate (1.2 g, 8.72 mmol) was stirred and heated in an oil bath at 50° C. for 7 hours. The mixture was evaporated under vacuum and the residue partitioned between EtOAc (100 mL) and water (100 mL) containing 2N HCl (10 mL). The organic phase was washed with brine (50 mL), dried over $MgSO_4$, filtered, and evaporated under vacuum to an oil (1.86 g) consisting of predominantly 1-(3-chloro-5-fluoro-4-methoxyphenyl)-2-(methoxymethyl)-1-hexanone.

The oil was cooled in an ice bath and treated with ice cold sulfuric acid (6 mL). The cooling bath was removed and the mixture was stirred at room temperature for 5 minutes, then heated in an oil bath at 50° C. for 35 minutes, kept at room temperature overnight, heated at 50° C. an additional 3 hours, and finally cooled to room temperature. The mixture was partitioned between EtOAc (100 mL) and ice cold water (100 mL). The organic phase was washed with brine (50 mL) and evaporated under vacuum to an oil (1.5 g). The $^1$H NMR spectrum os this material showed a mixture of 2-butyl-4-chloro-6-fluoro-5-methoxy-1-indanone (major product) and 2-butyl-6-chloro-4-fluoro-5-methoxy-1-indanone (minor product).

Step 3: 9a-butyl-8-chloro-6-fluoro-7-methoxy-4-methyl-1, 2,9,9a-tetrahydro-3H-fluoren-3-one A sample of the crude product from step 2 (360 mg, 1.33 mmol) in anhydrous tetrahydrofuran (2.7 mL) was treated with ethyl vinyl ketone (0.160 mL, 1.60 mmol) and 1,8-diazabicyclo[5.4.0]undec-7-ene (0.040 mL, 0.266 mmol). The mixture was stirred and heated in an oil bath at 60° C. for two hours. TLC showed very little reaction. The mixture was treated with 0.5M sodium methoxide in methanol (0.53 mL, 0.266 mmol) and stirred with heating at 60° C. for an additional 17 hours. After cooling to room temperature, the solvent was evaporated under vacuum to give a residue consisting mainly of 2-butyl-4-chloro-6-fluoro-5-methoxy-2-(3-oxopentyl)-1-indanone. This material was dissolved in acetic acid (6 mL), treated with aqueous 6N HCl (3 mL), and stirred while heating in an 80° C. oil bath for 23.5 hours. After cooling, the mixture was partitioned between EtOAc (150 mL) and water (150 mL). The organic phase was washed with aqueous $K_2CO_3$ (100 mL) and brine (50 mL), dried over $MgSO_4$, filtered, and evaporated under vacuum to a dark oil (480 mg). The crude product was purified by preparative layer chromatography on four 0.1×20×20 cm silica gel GF plates, developing with $CH_2Cl_2$. The product bands were eluted with EtOAc and the eluent evaporated under vacuum to give an oil (208 mg). This material was a mixture of 9a-butyl-8-chloro-6-fluoro-7-methoxy-4-methyl-1,2,9,9a-tetrahydro-3H-fluoren-3-one (major product) and 9a-butyl-6-chloro-8-fluoro-7-methoxy-4-methyl-1,2,9,9a-tetrahydro-3H-fluoren-3-one (minor product) as evidenced by $^1$H NMR spectroscopy.

Step 4: 9a-butyl-8-chloro-6-fluoro-7-hydroxy-4-methyl-1,2, 9,9a-tetrahydro-3H-fluoren-3-one The product mixture from step 3 and pyridine hydrochloride (5.3 g) were combined and heated in an oil bath at 200°

C. for 90 minutes. After cooling, the mixture was partitioned between EtOAc (50 mL) and water (50 ml). The organic phase was washed with brine (50 mL), dried over MgSO$_4$, filtered, and evaporated under vacuum to a blue oil. The oil was purified by preparative layer chromatography on four 0.05×20×20 silica gel GF plates, developing with 5% EtOAc in CH$_2$Cl$_2$. One of the plates was discarded due to excessive streaking. The combined product bands were eluted with EtOAc, the eluent evaporated under vacuum, and the residue lyophilized from benzene (3 mL) containing EtOH (2 drops) to afford 9a-butyl-8-chloro-6-fluoro-7-hydroxy-4-methyl-1,2,9,9a-tetrahydro-3H-fluoren-3-one as an amorphous solid.

$^1$H NMR (CDCl$_3$, 500 MHz) δ 0.85 (t, CH$_2$CH$_2$CH$_2$CH$_3$), 1.13–1.28 (m, CH$_2$CH$_2$CH$_2$CH$_3$), 1.39 and 1.57 (two m, CH$_2$CH$_2$CH$_2$CH$_3$), 1.99 and 2.25 (two ddd, 1-CH$_2$), 2.04 (s, 4-CH$_3$), 2.48 and 2.58 (two ddd, 2-CH$_2$), 2.68 and 3.03 (two d, 9-CH$_2$), 5.70 (d, OH), and 7.40 (d, H-5); mass spectrum m/z 323.2 (M+1).

EXAMPLE 31

SYNTHESIS OF 9a-BUTYL-8-CHLORO-4-ETHYL-6-FLUORO-7-HYDROXY-1,2,9,9a-TETRAHYDRO-3H-FLUOREN-3-ONE

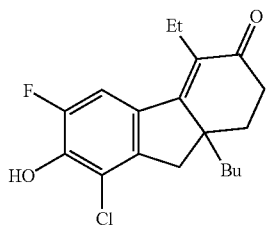

Step 1: 9a-butyl-8-chloro-4-ethyl-6-fluoro-7-methoxy-1,2,9,9a-tetrahydro-3H-fluoren-3-one A sample of the crude product from step 2 in the preceding example (386 mg, 1.36 mmol) in anhydrous tetrahydrofuran (2.7 mL) was treated with propyl vinyl ketone (0.188 mL, 1.63 mmol) and 1,8-diazabicyclo[5.4.0]undec-7-ene (0.041 mL, 0.272 mmol). The mixture was stirred and heated in an oil bath at 60° C. for two hours. TLC showed very little reaction. The mixture was treated with 0.5M sodium methoxide in methanol (0.54 mL, 0.272 mmol) and then stirred with heating at 60° C. for an additional 16.3 hours. After cooling to room temperature, the solvent was evaporated under vacuum to give a residue consisting mainly of 2-butyl-4-chloro-6-fluoro-5-methoxy-2-(3-oxohexyl)-1-indanone. This material was dissolved in acetic acid (6 mL), treated with aqueous 6N HCl (3 mL), and stirred while heating in an oil bath at 80° C. for 22.3 hours. After cooling, the mixture was partitioned between EtOAc (150 mL) and water (150 mL). The organic phase was washed with aqueous K$_2$CO$_3$ (100 mL) and brine (50 mL), dried over MgSO$_4$, filtered, and evaporated under vacuum to an oil (420 mg). The crude product was purified by preparative layer chromatography on four 0.1×20×20 cm silica gel GF plates, developing three times with 10% EtOAc in hexanes. The product bands were combined, eluted with EtOAc, and the eluent evaporated under vacuum to give 9a-butyl-8-chloro-4-ethyl-6-fluoro-7-methoxy-1,2,9,9a-tetrahydro-3H-fluoren-3-one as an oil (153 mg). The product contained trace amounts of 9a-butyl-6-chloro-4-ethyl-8-fluoro-7-methoxy-1,2,9,9a-tetrahydro-3H-fluoren-3-one as evidenced by $^1$H NMR spectroscopy.

Step 2: 9a-butyl-8-chloro-4-ethyl-6-fluoro-7-hydroxy-1,2,9,9a-tetrahydro-3H-fluoren-3-one The product from step 1 and pyridine hydrochloride (5.0 g) were combined and heated in an oil bath at 200° C. for 80 minutes. After cooling, the mixture was partitioned between EtOAc (50 mL) and water (50 ml). The organic phase was washed with brine (50 mL), dried over MgSO$_4$, filtered, and evaporated under vacuum to a blue oil. The oil was purified by preparative layer chromatography on three 0.05×20×20 silica gel GF plates, developing with 10% EtOAc in CH$_2$Cl$_2$. The combined product bands were eluted with EtOAc, the eluent evaporated under vacuum, and the residue lyophilized from benzene (3 mL) to afford 9a-butyl-8-chloro-4-ethyl-6-fluoro-7-hydroxy-1,2,9,9a-tetrahydro-3H-fluoren-3-one as an amorphous solid.

$^1$H NMR (CDCl$_3$, 500 MHz) δ 0.85 (t, CH$_2$CH$_2$CH$_2$CH$_3$), 1.09 (t, CH$_2$CH$_3$), 1.13–1.28 (m, CH$_2$CH$_2$CH$_2$CH$_3$), 1.39 and 1.56 (two m, CH$_2$CH$_2$CH$_2$CH$_3$), 1.98 and 2.25 (two ddd, 1-CH$_2$), 2.41 and 2.62 (two dq, CH$_2$CH$_3$), 2.42 and 2.56 (two ddd, 2-CH$_2$), 2.65 and 3.02 (two d, 9-CH$_2$), 5.70 (d, OH), and 7.35 (d, H-5); mass spectrum m/z 337.2 (M+1).

EXAMPLE 32

SYNTHESIS OF 4-BROMO-9a-BUTYL-8-CHLORO-6-FLUORO-7-HYDROXY-1,2,9.9a-TETRAHYDRO-3H-FLUOREN-3-ONE

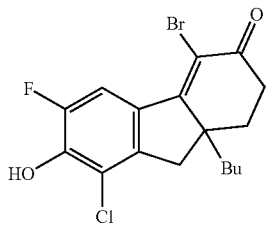

Step 1: 9a-butyl-8-chloro-6-fluoro-7-methoxy-1,2,9,9a-tetrahydro-3H-fluoren-3-one A solution of crude 2-butyl-4-chloro-6-fluoro-5-methoxy-1-indanone (386 mg, 1.4 mmol) in tetrahydrofuran (2.8 mL) was treated with methyl vinyl ketone (0.150 mL, 1.78 mmol) and 0.5N sodium methoxide in methanol (1.1 mL, 0.56 mmol). The mixture was stirred at room temperature for 5.5 hours to effect conversion to 2-butyl-4-chloro-6-fluoro-5-methoxy-2-(3-oxobutyl)-1-indanone. The reaction mixture was diluted with toluene (10 mL), treated with pyrrolidine (0.117 mL, 1.4 mmol) and acetic acid (0.112 mmol, 1.46 mmol), and then stirred and heated in an oil bath at 80° C. for 3 hours. After storing overnight at room temperature, the mixture was partitioned between EtOAc (50 mL) and water (50 mL). The organic phase was washed with 0.1N HCl (50 mL), saturated aqueous NaHCO$_3$ (50 mL) and brine (20 mL), dried over MgSO$_4$, filtered, and evaporated under vacuum. The oily residue was purified by preparative layer chromatography on four 0.1×20×20 cm silica gel GF plates, developing with 5% EtOAc in CH$_2$Cl$_2$. The product bands were combined, eluted with EtOAc, and the eluent evaporated under vacuum to provide 9a-butyl-8-chloro-6-fluoro-7-methoxy-1,2,9,9a-tetrahydro-3H-fluoren-3-one (160 mg) as a solid. $^1$H NMR spectroscopy revealed that the product contained a minor amount of the isomeric product 9a-butyl-6-chloro-8-fluoro-7-methoxy-1,2,9,9a-tetrahydro-3H-fluoren-3-one which is derived from a minor amount of 2-butyl-6-chloro-4-fluoro-5-methoxy-1-indanone in the starting material.

Step 2: 4-bromo-9a-butyl-8-chloro-6-fluoro-7-methoxy-1,2,9,9a-tetrahydro-3H-fluoren-3-one A solution of the product from step 1 (160 mg, 0.52 mmol) in anhydrous dichloromethane (5.2 mL) was cooled in an ice bath and treated with sodium bicarbonate (21.8 m, 2.6 mmol) and bromine (0.028 mL, 0.52 mmol). The mixture was stirred at 0° C. for 15 minutes and then diluted with $CH_2Cl_2$ (20 mL) and washed with water (25 mL). The organic phase was dried over $MgSO_4$, filtered and evaporated tinder vacuum. The residue was purified by preparative layer chromatography on three 0.05×20×20 cm silica gel GF plates, developing with 10% EtOAc in hexanes. The product bands were combined, eluted with EtOAc, and the eluent evaporated under vacuum to afford 4-bromo-9a-butyl-8-chloro-6-fluoro-7-methoxy-1,2,9,9a-tetrahydro-3H-fluoren-3-one (110 mg) as a solid.

Step 3: 4-bromo-9a-butyl-8-chloro-6-fluoro-7-hydroxy-1,2,9,9a-tetrahydro-3H-fluoren-3-one A solution of 4-bromo-9a-butyl-8-chloro-6-fluoro-7-methoxy-1,2,9,9a-tetrahydro-3H-fluoren-3-one (31 mg, 0.077 mmol) in anhydrous dichloromethane (0.5 mL) was cooled in a dry ice-acetone bath (−78° C.) and the solution treated with 1M boron tribromide in dichloromethane (0.231 mL, 0.231 mmol). The cooling bath was removed and the mixture was stirred at room temperature for one hour. The mixture was partitioned between EtOAc (20 mL) and water (20 mL) containing 2N HCl (2 mL). The organic phase was washed with brine (10 mL), dried over $MgSO_4$, filtered, and evaporated under vacuum. The residue was purified by preparative layer chromatography on a 0.05×20×20 cm silica gel GF plate, developing with 10% EtOAc in $CHCl_2$. The product band was eluted with EtOAc, the eluent evaporated under vacuum, and the residue lyophilized from benzene plus a few drops of EtOH to afford 4-bromo-9a-butyl-8-chloro-6-fluoro-7-hydroxy-1,2,9,9a-tetrahydro-3H-fluoren-3-one as an amorphous solid.

$^1$H NMR ($CDCl_3$, 500 MHz) δ 0.86 (t, $CH_2C_2C_2CH_3$), 1.13–1.30 (m, $CH_2CH_2CH_3$), 1.49 and 1.64 (two m, $CH_2CH_2CH_3$), 2.09 and 2.29 (two ddd, 1-$CH_2$), 2.70–2.80 (m, 2-$CH_2$), 2.74 and 3.08 (two d, 9-$CH_2$), 5.83 (s, OH), and 8.29 (d, H-5); mass spectrum m/z 387.0 (M+1) and 389.0 (M+3).

EXAMPLE 33

SYNTHESIS OF 9a-BUTYL-8-CHLORO-6-FLUORO-7-HYDROXY-4-(TRIFLUOROMETHYL)-1,2,9,9a-TETRAHYDRO-3H-FLUOREN-3-ONE

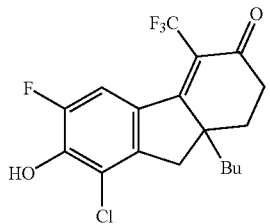

Step 1: 9a-butyl-8-chloro-6-fluoro-7-methoxy-4-(trifluoromethyl)-1,2,9,9a-tetrahydro-3H-fluoren-3-one A mixture of 4-bromo-9a-butyl-8-chloro-6-fluoro-7-methoxy-1,2,9,9a-tetrahydro-3H-fluoren-3-one (47 mg, 0.117 mmol), copper(I) iodide (27 mg, 0.14 mmol), methyl difluoro(fluorosulfonyl)acetate (0.108 mL, 0.85 mmol), and anhydrous N,N-dimethylformamide (5.9 mL) was placed under a nitrogen atmosphere, stirred, and heated in an oil bath at 75–80° C. for 7 hours. After cooling to room temperature, the mixture was diluted with EtOAc (50 mL), washed with water (5×100 mL) and brine (50 mL), dried over $MgSO_4$, filtered, and evaporated under vacuum to an oil (47 mg). The crude product was purified by preparative layer chromatography on a 0.1×20×20 cm silica gel GF plate, developing with 10% EtOAc in hexanes. The product band was eluted with EtOAc and the eluent evaporated under vacuum to afford 9a-butyl-8-chloro-6-fluoro-7-methoxy-4-(trifluoromethyl)-1,2,9,9a-tetrahydro-3H-fluoren-3-one (39 mg) as an oil.

Step 2: 9a-butyl-8-chloro-6-fluoro-7-hydroxy-4-(trifluoromethyl)-1,2,9,9a-tetrahydro-3H-fluoren-3-one A solution of 9a-butyl-8-chloro-6-fluoro-7-methoxy-4-(trifluoromethyl)-1,2,9,9a-tetrahydro-3H-fluoren-3-one (39 mg, 0.10 mmol) in anhydrous dichloromethane (1.0 mL) was cooled in a dry ice-acetone bath (−78° C.) and the solution was treated with 1M boron tribromide in dichloromethane (0.3 mL, 0.3 mmol). The cooling bath was removed and the mixture was stirred at room temperature for one hour. The mixture was partitioned between EtOAc (20 mL) and water (20 mL) containing 2N HCl (1 mL). The organic phase was washed with brine (10 mL), dried over $MgSO_4$, filtered, and evaporated under vacuum. The residue was purified by preparative layer chromatography on a 0.1×20×20 cm silica gel GF plate, developing with 10% EtOAc in $CH_2Cl_2$. The product band was eluted with 10% MeOH in $CH_2Cl_2$, the eluent evaporated under vacuum, and the residue lyophilized from benzene plus a few drops of EtOH to afford 9a-butyl-8-chloro-6-fluoro-7-hydroxy-4-(trifluoromethyl)-1,2,9,9a-tetrahydro-3H-fluoren-3-one as an amorphous solid.

$^1$H NMR ($CDCl_3$, 500 MHz) δ 0.85 (t, $CH_2CH_2CH_2CH_3$), 1.11–1.28 (m, $CH_2CH_2CH_2CH_3$), 1.32 and 1.53 (two m, $CH_2CH_2CH_2CH_3$), 2.07 and 2.26 (two ddd, 1-$CH_2$), 2.50–2.64 (m, 2-$CH_2$), 2.78 and 3.08 (two d, 9-$CH_2$), 5.89 (br s, OH), and 7.54 (m, H-5); mass spectrum m/z 377.1 (M+1).

EXAMPLE 34

SYNTHESIS OF 2-HYDROXY-5-METHYLGIBBA-1(10a),2,4,4b-TETRAEN-6-ONE

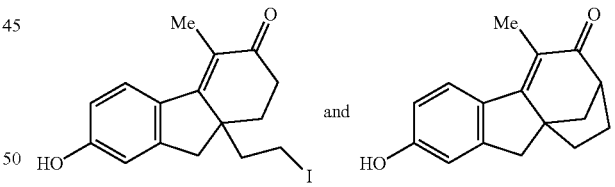

Step 1: 2-(2-hydroxyethyl)-5-methoxy-1-indanone

A solution of 5-methoxy-1-indanone (500 mg, 3.08 mmol) in methanol (10 mL) was treated with 10% palladium on carbon (53 mg) followed by glycoaldehyde dimer (370 mg, 3.08 mmol) and 0.5M sodium methoxide in methanol (1.3 mL, 0.65 mmol). The mixture was placed under a hydrogen atmosphere (balloon) and stirred vigorously at room temperature for 65 hours. After purging with nitrogen, the mixture was filtered through a 0.45 μm Acrodisc and the disk was rinsed with methanol (2 mL). The filtrate was diluted with EtOAc (25 mL), washed with 0.1N HCl (15 mL) and brine (15 mL), dried over $MgSO_4$, filtered, and evaporated under vacuum to a solid (436 mg). LC-MS of this material showed a mixture of starting material (major) and product.

The mixture was purified by chromatography on a Biotage Flash 12M KP-Sil column (12 mm×15 cm). The column was eluted with 3:2 EtOAc-hexanes, collecting 6 mL fractions every 30 sec. Fractions 20–36 were concentrated under vacuum and flashed with benzene to afford 2-(2-hydroxyethyl)-5-methoxy-1-indanone (106 mg, 17% yield) as an oil.

$^1$H NMR (CDCl$_3$, 500 MHz) δ 1.80 and 2.05 (two m, CH$_2$CH$_2$OH), 2.79 and 3.35 (two dd, 3-CH$_2$), 2.83 (m, H-2), 3.77–3.90 (m, CH$_2$CH$_2$OH), 3.87 (s, OCH$_3$), 6.86 (d, H-4), 6.89 (dd, H-6), and 7.67 (d, H-7).

Step 2: 2-(2-hydroxyethyl)-5-methoxy-2-(3-oxopentyl)-1-indanone

A solution of 2-(2-hydroxyethyl)-5-methoxy-1-indanone (105 mg, 0.51 mmol) in methanol (2.0 mL) at room temperature was treated with ethyl vinyl ketone (EVK, 0.102 mL) and 0.5M sodium methoxide in methanol (0.204 mL, 0.1 mmol). The mixture was stirred in a capped flask and heated in an oil bath at 60° C. for 8 hours. After cooling, the reaction mixture was diluted with EtOAc (25 mL), washed with 0.2N HCl (15 mL), water (15 mL), and brine (15 mL), dried over MgSO$_4$, filtered, and evaporated under vacuum to afford 2-(2-hydroxyethyl)-5-methoxy-2-(3-oxopentyl)-1-indanone (138 mg, 93% yield) as an oil.

$^1$H NMR (CDCl$_3$, 500 MHz) δ 0.99 (t, COCH$_2$CH$_3$), 1.84–2.00 (m, CH$_2$CH$_2$OH and CH$_2$CH$_2$CO), 2.28 (m, CH$_2$CH$_2$CO), 2.33 (m, COCH$_2$CH$_3$), 2.92 and 3.11 (two d, 3-CH$_2$), 3.63 and 3.72 (two m, CH$_2$CH$_2$OH), 3.87 (s, OCH$_3$), 6.86 (d, H-4), 6.91 (dd, H-6), and 7.67 (d, H-7).

Step 3: 9a-(2-hydroxyethyl)-7-methoxy-4-methyl-1,2,9,9a-tetrahydro-3H-fluoren-3-one and 9a-(2-acetoxyethyl)-7-methoxy-4-methyl-1,2,9,9a-tetrahydro-3H-fluoren-3-one A solution of 2-(2-hydroxyethyl)-5-methoxy-2-(3-oxopentyl)-1-indanone (138 mg, 0.475 mmol) in acetic acid (3.0 mL) was diluted with aqueous 6N HCl (3.0 mL) and the resulting mixture was stirred and heated in an oil bath at 80° C. for 90 minutes. After cooling to room temperature, the reaction mixture was diluted with EtOAc (20 mL), washed with water (10 mL), 1M pH 7 phosphate buffer (15 ml), water (15 mL), and brine (15 mL), dried over MgSO$_4$, filtered, and evaporated under vacuum to an oil (139 mg). LC-MS showed a mixture of 9a-(2-hydroxyethyl)-7-methoxy-4-methyl-1,2,9,9a-tetrahydro-3H-fluoren-3-one and its O-acetyl derivative 9a-(2-acetoxyethyl)-7-methoxy-4-methyl-1,2,9,9a-tetrahydro-3H-fluoren-3-one.

Step 4: 9a-(2-hydroxyethyl)-7-methoxy-4-methyl-1,2,9,9a-tetrahydro-3H-fluoren-3-one The mixture of products from step 3 was dissolved in methanol (5 mL) and the solution treated with 0.5M sodium methoxide in methanol (4.5 mL). The mixture was stirred at room temperature for 15 minutes then acidified with aqueous 2N HCl and concentrated under vacuum. The residue in EtOAc (25 mL) was washed with brine (20 mL), dried over MgSO$_4$, filtered, and evaporated under vacuum. The crude product was purified by chromatography on a Biotage Flash-12 M KP-Sil column (12 mm×15 cm). The column was eluted with 3:2 EtOAc-hexanes (145 mL) followed by 100% EtOAc, collecting 4 mL fractions every 30 seconds. Fractions 30–50 were combined and evaporated under vacuum to give the product as an oil (54.7 mg, 42% yield). Treatment of this material with Et$_2$O gave the product 9a-(2-hydroxyethyl)-7-methoxy-4-methyl-1,2,9,9a-tetrahydro-3H-fluoren-3-one as a solid.

$^1$H NMR (CDCl$_3$, 500 MHz) δ 1.72–1.86 (m, CH$_2$CH$_2$OH), 1.99 and 2.21 (two ddd, 1-CH$_2$), 2.04 (s, 4-CH$_3$), 2.45 and 2.63 (two ddd, 2-CH$_2$), 2.76 and 3.05 (two d, 9-CH$_2$), 3.47–3.62 (m, CH$_2$CH$_2$OH), 3.82 (s, OCH$_3$), 6.81–8.85 (m, H-6 and H-8), and 7.61 (d, H-5).

Step 5: 9a-[2-(methanesulfonyoxy)ethyl]-7-methoxy-4-methyl-1,2,9,9a-tetrahydro-3H-fluoren-3-one An ice-cold solution of 9a-(2-hydroxyethyl)-7-methoxy-4-methyl-1,2,9,9a-tetrahydro-3H-fluoren-3-one (39 mg, 0.14 mmol) and triethylamine (0.030 mL, 0.21 mmol) in anhydrous dichloromethane (1.5 ml) was treated with methanesulfonyl chloride (0.014 mL, 0.18 mmol) and the resulting solution was stirred at 0° C. for 30 minutes. The mixture was diluted with EtOAc (10 mL), washed with water (5 mL), 0.2N HCl (5 mL), and brine (5 mL), dried over MgSO$_4$, filtered, and evaporated under vacuum to provide 9a-[2-(methanesulfonyoxy)ethyl]-7-methoxy-4-methyl-1,2,9,9a-tetrahydro-3H-fluoren-3-one (49.7 mg, 99% yield) as an oil.

$^1$H NMR (CDCl$_3$, 500 MHz) δ 2.03 (m, CH$_2$CH$_2$O), 2.08 (s, 4-CH$_3$), 2.09 and 2.22 (two ddd, 1-CH$_2$), 2.53 and 2.61 (two ddd, 2-CH$_2$), 2.85 and 3.03 (two d, 9-CH$_2$), 2.89 (s, SO$_2$CH$_3$), 3.85 (s, OCH$_3$), 4.03–4.17 (m, CH$_2$CH$_2$O), 6.86 (s, H-8), 6.87 (dd, H-6), and 7.64 (d, H-5).

Step 6: 9a-(2-iodoethyl)-7-methoxy-4-methyl-1,2,9,9a-tetrahydro-3H-fluoren-3-one A solution of 2-(2-methoxy-5-methyl-6-oxo-6,7,8,9-tetrahydro-8aH-fluoren-8a-yl)ethyl methanesulfonate (49.7 mg, 0.142 mmol) in acetone (2.0 mL) was treated with sodium iodide (85 mg, 0.57 mmol) and the resulting mixture was stirred and heated in an oil bath at 60° C. for 16 hours. After cooling, the mixture was diluted with acetone (2 mL) and filtered through a 0.45 Fm Acrodisc filter. The filtrate was evaporated under vacuum and the residue in CH$_2$Cl$_2$ (3 mL) was re-filtered. The filtrate was purified by chromatography on a Biotage Flash 12M KP-Sil column (12 mm×15 cm) which was eluted with 4:1 hexanes-EtOAc, collecting 6 mL fractions every 30 seconds. Fractions 9–11 gave 9a-(2-iodoethyl)-7-methoxy-4-methyl-1,2,9,9a-tetrahydro-3H-fluoren-3-one (34.5 mg, 64% yield) as an oil.

$^1$H NMR (CDCl$_3$, 500 MHz) δ 2.03 and 2.20 (two ddd, 1-CH$_2$), 2.08 (s, 4-CH$_3$), 2.24 (m, CH$_2$CH$_2$I), 2.51 and 2.61 (two ddd, 2-CH$_2$), 2.80 and 2.97 (two d, 9-CH$_2$), 2.85 and 2.95 (two m, CH$_2$CH$_2$I), 3.86 (s, OCH$_3$), 6.86 (br s, H-8), 6.87 (dd, H-6), and 7.64 (d, H-5).

Step 7: 2-methoxy-5-methylgibba-1(10a),2,4,4b-tetraen-6-one

A solution of N,N-diisopropylamine (0.015 mL, 0.107 mmol) in anhydrous tetrahydrofuran (THF, 1.0 mL) was placed under a nitrogen atmosphere, cooled in an ice bath, and treated with 1.6 M n-butyllithium in hexanes (0.061 mL, 0.098 mmol). The solution was stirred at 0° C. for 35 minutes, then cooled in a dry ice-acetone bath and, after aging for 5 minutes, treated with a solution of 9a-(2-iodoethyl)-7-methoxy-4-methyl-1,2,9,9a-tetrahydro-3H-fluoren-3-one (34 mg, 0.089 mmol) in THF (1.0 mL). The reaction mixture was warmed from −78° C. to room temperature over 4 hours, stirred at room temperature for 21 hours, and then quenched with aqueous 2N HCl (0.5 mL) and diluted with EtOAc (10 mL). The organic phase was washed with water (5 mL) and brine (5 mL), dried over MgSO$_4$, filtered, and evaporated under vacuum to an oil (27.2 mg). This material was purified by chromatography on a Biotage Flash 12M KP-Sil column (12 mm×15 cm), eluting with 6:1 hexanes-EtOAc and collecting 7 mL fractions every 30 seconds. Fractions 16–20 were combined and evaporated under vacuum to give a mixture (21.7 mg) of 2-methoxy-5-methylgibba-1(10a),2,4,4b-tetraen-6-one and the starting material 9a-(2-iodoethyl)-7-methoxy-4-methyl-1,2,9,9a-tetrahydro-3H-fluoren-3-one as an oil.

Step 8: 2-hydroxy-5-methylgibba-1(10a),2,4,4b-tetraen-6-one and 7-hydroxy-9a-(2-iodoethyl)-4-methyl-1,2,9,9a-tetrahydro-3H-fluoren-3-one A solution of the product mixture from step 7 (21.7 mg, approx. 0.1 mmol) in anhydrous dichloromethane (1.0 mL) was treated at room temperature with aluminum chloride (75 mg, 0.56 mmol) and ethanethiol (0.032 mL, 0.43 mmol). After stirring at room temperature for 58 minutes, the yellow solution was treated with aqueous 2N HCl (1 mL) and EtOAc (9 ml), washed with water (4 mL) and brine (5 mL), dried over $MgSO_4$, filtered, and evaporated under vacuum to a solid film. The solid in warm EtOH (1 mL) was applied to two 0.1×20×20 cm silica gel GF plates which were developed with 1:1-hexanes-EtOAc. Two UV visible bands were removed, eluted with EtOAc, concentrated under vacuum, and the residues lyophilized from benzene containing some acetone. The band at $R_f$ 0.57–0.67 gave mainly 7-hydroxy-9a-(2-iodoethyl)-4-methyl-1,2,9,9a-tetrahydro-3H-fluoren-3-one as an amorphous solid (contains approx. 11% of the major tetracyclic product). The band at $R_f$ 0.47–0.57 gave mainly 2-hydroxy-5-methylgibba-1(10a),2,4,4b-tetraen-6-one as an amorphous solid (contains approx. 16% of the minor 9a-iodoethyl product). 9a-Iodoethyl-tetrahydrofluorenone product: $^1$H NMR (approx. 3:2 $CD_3CN:CDCl_3$, 500 MHz) δ 1.84 (p, $CHD_2CN$), 1.87 (m, 1-$CH_aH_b$), 1.92 (s, 4-$CH_3$), 2.01–2.12 (m, 1-$CH_aH_b$ and $CH_2CH_2I$), 2.31 and 2.44 (two ddd, 2-$CH_2$), 2.61 and 2.83 (two d, 9-$CH_2$), 2.76 and 2.87 (two m, $CH_2CH_2I$), 6.63–6.66 (m, H-6 and H-8), 7.20 (br s, OH), 7.29 (s, $CHCl_3$), and 7.43 (d, H-5); mass spectrum m/z 369.2 (M+1).

Gibbatetraenone product: $^1$H NMR ($CDCl_3$, 500 MHz) δ 1.64, 1.75–1.86, 2.26 (three m, 8-$CH_2$ and 9-$CH_2$), 1.88 and 1.95 (dd and d, 11-$CH_2$), 2.06 (s, 5-$CH_3$), 2.98 and 3.22 (two d, 10-$CH_2$), 3.07 (dd, H-7), 5.87 (br s, OH), 6.83 (dd, H-3), 6.86 (br s, H-1), and 7.64 (d, H-4).

EXAMPLE 35
SYNTHESIS OF 4-BROMO-9a-BUTYL-3-OXO-2,3,9,9a-1H-FLUOREN-7-YL PIVALATE

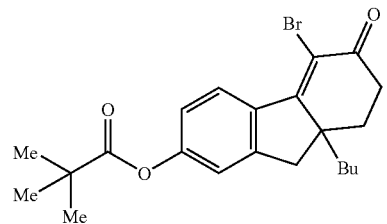

A solution of 4-bromo-9a-butyl-7-hydroxy-1,2,9,9a-tetrahydro-3H-fluoren-3-one (30 mg, 0.09 mmol) in anhydrous dichloromethane (1.0 mL) was treated with triethylamine (0.015 mL, 0.108 mmol) and pivaloyl chloride (0.0123 mL, 0.1 mmol). After stirring at room temperature for 20 minutes, the reaction mixture was purified by preparative layer chromatography on a 0.1×20×20 cm silica get GF plate, developing with 5% EtOAc in $CH_2Cl_2$. The product band was eluted with EtOAc, the eluent was evaporated under vacuum, and the residue was lyophilized from benzene to afford 4-bromo-9a-butyl-3-oxo-2,3,9,9a-1H-fluoren-7-yl pivalate as an amorphous solid.

$^1$H NMR ($CDCl_3$, 500 MHz) δ 0.84 (t, $CH_2CH_2CH_2CH_3$), 1.15–1.30 (m, $CH_2CH_2CH_2CH_3$), 1.37 (s, $C(CH_3)_3$), 1.47 and 1.64 (two m, $CH_2CH_2CH_2CH_3$), 2.08 and 2.27 (two ddd, 1-$CH_2$), 2.69–2.77 (m, 2-$CH_2$), 2.81 and 3.04 (two d, 9-$CH_2$), 7.05 (dd, H-6), 7.08 (s, H-8), and 8.55 (d, H-5).

EXAMPLES 36–111

The following compounds were prepared using methods analogous to those described in the preceding examples:

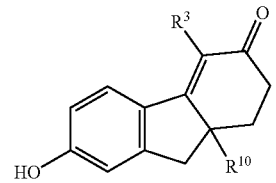

| | | |
|---|---|---|
| 36 | $R^3$ = $CH_3$ | 7-hydroxy-4,9a-dimethyl-1,2,9,9a-tetrahydro-3H-fluoren-3-one |
| | $R^{10}$ = $CH_3$ | |

$^1$H NMR (DMSO-$d_6$, 500 MHz) δ 1.14 (s, 9a-$CH_3$), 1.92 (s, 4-$CH_3$), 1.98–2.06 (m, 1-$CH_2$), 2.33 and 2.58 (two ddd, 2-$CH_2$), 2.71 and 2.78 (two d, 9-$CH_2$), 6.74 (dd, H-6), 6.79 (d, H-8), and 7.55 (d, H-5).

| | | |
|---|---|---|
| 37 | $R^3$ = $CH_3$ | 9a-ethyl-7-hydroxy-4-methyl-1,2,9,9a-tetrahydro-3H-fluoren-3-one |
| | $R^{10}$ = $CH_2CH_3$ | |

$^1$H NMR (DMSo-$d_6$, 500 MHz) δ 0.79 (t, $CH_2CH_3$), 1.32 and 1.55 (two dq, $CH_2CH_3$), 1.90 and 2.12 (two m, 1-$CH_2$), 1.93 (s, 4-$CH_3$), 2.28 and 2.48 (two m, 2-$CH_2$), 2.60 and 2.88 (two d, 9-$CH_2$), 6.73 (dd, H-6), 6.76 (d, H-8), and 7.55 (d, H-5).

| | | |
|---|---|---|
| 38 | $R^3$ = $CH_3$ | 7-hydroxy-4-methyl-9a-propyl-1,2,9,9a-tetrahydro-3H-fluoren-3-one |
| | $R^{10}$ = $CH_2CH_2CH_3$ | |

$^1$H NMR (DMSO-$d_6$, 500 MHz) δ 0.78 (t, $CH_2CH_2CH_3$), 1.12 and 1.23 (two m, $CH_2CH_2CH_3$), 1.27 and 1,49 (two m, $CH_2CH_2CH_3$), 1.91 and 2.11 (two ddd, 1-$CH_2$), 1.92 (s, 4-$CH_3$), 2.28 and 2.50 (two ddd, 2-$CH_2$), 2.63 and 2.89 (two d, 9-$CH_2$), 6.73 (dd, H-6), 6.76 (d, H-8), and 7.54 (d, H-5).

| | | |
|---|---|---|
| 39 | $R^3$ = $CH_3$ | 7-hydroxy-9a-isobutyl-4-methyl-1,2,9,9a-tetrahydro-3H-fluoren-3-one |
| | $R^{10}$ = $CH_2CH(CH_3)$ | |

$^1$H NMR ($CDCl_3$, 500 MHz) δ 0.82 and 0.90 (two d, $CH(CH_3)_2$), 1.34 and 1.53 (two dd, $CH_2CH(CH_3)_2$), 1.62 (m, $CH(CH_3)_2$), 1.99 and 2.25 (two ddd, 1-$CH_2$), 2.08 (s, 4-$CH_3$), 2.52 and 2.65 (two ddd, 2-$HC_2$), 2.72 and 3.02 (two d, 9-$CH_2$), 5.30 (s, OH), 6.83–6.87 (m, H-6 and H-8), and 7.61 (d, H-5); mass spectrum m/z 271.1 (M + 1).

| | | |
|---|---|---|
| 40 | $R^3$ = $CH_2CH_3$ | 9a-butyl-4-ethyl-7-hydroxy-1,2,9,9a-tetrahydro-3H-fluoren-3-one |
| | $R^{10}$ = $CH_2CH_2CH_2CH_3$ | |

$^1$H NMR (DMSO-$d_6$, 500 MHz) δ 0.79 (t, $CH_2CH_2CH_2CH_3$), 0.97 (t, $CH_2CH_3$), 1.06–1.26 (m, $CH_2CH_2CH_2CH_3$), 1.26 and 1.48 (two m, $CH_2CH_2CH_2CH_3$), 1.89 and -continued 2.10 (two m, 1-CH$_2$), 2.26 and 2.46 (two m, 2-CH$_2$), 2.35 and 2.52 (two m, CH$_2$CH$_3$), 2.61 and 2.87 (two d, 9-CH$_2$), 6.72–6.77 (m, H-6 and H-8), 7.48 (d, H-5).

| 41 | R$^3$ = CH$_2$CH$_2$CH$_3$ | 9a-butyl-7-hydroxy-4-propyl-1,2,9,9a-tetrahydro- |
| | R$^{10}$ = CH$_2$CH$_2$CH$_2$CH$_3$ | 3H-fluoren-3-one |

$^1$H NMR (CDCl$_3$, 500 MHz) δ 0.84 (t, CH$_2$CH$_2$CH$_2$CH$_3$), 1.01 (t, CH$_2$CH$_2$CH$_3$), 1.22, 1.39. and 1.56 (three m, CH$_2$CH$_2$CH$_2$CH$_3$ and CH$_2$CH$_2$CH$_3$), 1.96 and 2.21 (two m, 1-CH$_2$), 2.38–2.49 and 2.52–2.65 (two m, 2-CH$_2$ and CH$_2$CH$_2$CH$_3$), 2.68 and 2.93 (two d, 9-CH$_2$), 6.77–6.81 (m, H-6 and H-8), and 7.51 (dd, H-5).

| 42 | R$^3$ = CH$_2$CH$_2$CH$_2$CH$_3$ | 4,9a-dibutyl-7-hydroxy-1,2,9,9a-tetrahydro-3H- |
| | R$^{10}$ = CH$_2$CH$_2$CH$_2$CH$_3$ | 3H-fluoren-3-one |
| 43 | R$^3$ = Cl | 9a-butyl-4-chloro-7-hydroxy-1,2,9,9a-tetrahydro- |
| | R$^{10}$ = CH$_2$CH$_2$CH$_2$CH$_3$ | 3H-fluoren-3-one |

$^1$H NMR (DMSO-d$_6$, 500 MHz) δ 0.78 (t, CH$_2$CH$_2$CH$_2$CH$_3$), 1.04–1.27 (m, CH$_2$CH$_2$CH$_2$CH$_3$), 1.34 and 1.60 (two m, CH$_2$CH$_2$CH$_2$CH$_3$), 2.02 and 2.13 (two m, 1-CH$_2$), 2.48 and 2.68 (two m, 2-CH$_2$), 2.73 and 2.96 (two d, 9-CH$_2$), 6.76–6.81 (m, H-6 and H-8), 8.07 (d, H-5), and 10.35 (br s, OH).

| 44 | R$^3$ = I | 9a-butyl-7-hydroxy-4-iodo-1,2,9,9a-tetrahydro- |
| | R$^{10}$ = CH$_2$CH$_2$CH$_2$CH$_3$ | 3H-fluoren-3-one |

$^1$H NMR (DMSO-d$_6$, 500 MHz) δ 0.78 (t, CH$_2$CH$_2$CH$_2$CH$_3$), 1.04–1.26 (m, CH$_2$CH$_2$CH$_2$CH$_3$), 1.30 and 1.55 (two m, CH$_2$CH$_2$CH$_2$CH$_3$), 2.00 and 2.12 (two ddd, 1-CH$_2$), 2.56 and 2.74 (two ddd, 2-CH$_2$), 2.72 and 2.90 (two d, 9-CH$_2$), 6.80 (d, H-8), 6.84 (dd, H-6), 8.52 (d, H-5), and 10.36 (s, OH).

| 45 | R$^3$ = CF$_3$ | 9a-butyl-7-hydroxy-4-trifluoromewthyl-1,2,9,9a- |
| | R$^{10}$ = CH$_2$CH$_2$CH$_2$CH$_3$ | tetrahydro-3H-fluoren-3-one |

$^1$H NMR (CDCl$_3$, 500 MHz) δ 0.83 (t, CH$_2$CH$_2$CH$_2$CH$_3$), 1.21 (m, CH$_2$CH$_2$CH$_2$CH$_3$), 1.29 and 1.52 (two m, CH$_2$CH$_2$CH$_2$CH$_3$), 2.04 and 2.21 (two ddd, 1-CH$_2$), 2.49–2.61 (m, 2-CH$_2$), 2.79 and 2.97 (two d, 9-CH$_2$), 5.23 (s, OH), 6.75–6.79 (m, H-6 and H-8), and 7.73 (d, H-5); mass spectrum m/z 325.1 (M + 1).

| 46 | 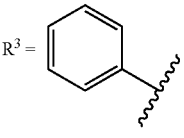 | 9a-butyl-7-hydroxy-4-phenyl-1,2,9,9a-tetrahydro- |
| | R$^3$ = | 3H-fluoren-3-one |

R$^{10}$ = CH$_2$CH$_2$CH$_2$CH$_3$ $^1$H NMR (DMSO-d$_6$, 500 MHz) δ 0.83 (t, CH$_2$CH$_2$CH$_2$CH$_3$), 1.15–1.33 (m, CH$_2$CH$_2$CH$_2$CH$_3$), 1.42 and 1.68 (two m, CH$_2$CH$_2$CH$_2$CH$_3$), 2.07 and 2.21 (two ddd, 1-CH$_3$), 2.38 and 2.59 (two ddd, 2-CH$_2$), 2.70 and 2.94 (two d, 9-CH$_2$), 6.04 (d, H-5), 6.30 (dd, H-6), 6.70 (d, H-8), 6.9–7.1 and 7.3–7.43 (two br m, C$_6$H$_5$), and 9.96 (br s, OH).

| 47 | 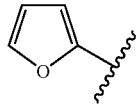 | 9a-butyl-4-(2-furyl)-7-hydroxy-1,2,9,9a- |
| | R$^3$ = | tetrahydro-3H-fluoren-3-one |

R$^{10}$ = CH$_2$CH$_2$CH$_2$CH$_3$ $^1$H NMR (DMSO-d$_6$, 500 MHz) δ 0.81 (t, CH$_2$CH$_2$CH$_2$CH$_3$), 1.11–1.31 (m, CH$_2$CH$_2$CH$_2$CH$_3$), 1.38 and 1.64 (two m, CH$_2$CH$_2$CH$_2$CH$_3$), 2.01 and 2.18 (two ddd, 1-CH$_2$), 2.39 and 2.58 (two ddd, 2-CH$_2$), 2.71 and 2.96 (two d, 9-CH$_2$), 6.16 (d, H-5), 6.25 (dd, furyl H-3), 6.51 (dd, H-6), 6.56 (dd, furyl H-4), 6.74 (d, H-8), 7.69 (dd, furyl H-5), and 10.18 (br s, OH).

| 48 | R$^3$ = CH$_3$ | 7-hydroxy-9a-(3-iodopropyl)-4-methyl-1,2,9,9a- |
| | R$^{10}$ = CH$_2$CH$_2$CH$_2$I | tetrahydro-3H-fluoren-3-one |

$^1$H NMR (CDCl$_3$, 500 MHz) δ 1.47–1.56 and 1.65–1.83 (two m, CH$_2$CH$_2$CH$_2$I), 2.03 and 2.18 (two ddd, 1-CH$_2$), 2.08 (s, 4-CH$_3$), 2.51 and 2.62 (two ddd, 2-CH$_2$), 2.74 and 2.92 (two d, 9-CH$_2$), 3.01–3.12 (m, CH$_2$CH$_2$CH$_2$I), 6.80–6.83 (m, H-6 and H-8), and 7.61 (d, H-5); mass spectrum m/z 383.1 (M + 1).

| 49 | R$^3$ = CH$_3$ | 7-hydroxy-4-methyl-9a-(2-methyl-1-propenyl)- |
| | R$^{10}$ = CH=C(CH$_3$)$_2$ | 1,2,9,9a-tetrahydro-3H-fluoren-3-one |

$^1$H NMR (3:1 CDCl$_3$—CD$_3$CN, 500 MHz) δ 1.52 and 1.53 (two s, =C(CH$_3$)$_2$), 1.96 and 2.28 (two m, 1-CH$_2$), 1.96 (s, 4-CH$_3$), 2.28 and 2.47 (two m, 2-CH$_2$), 2.84 and 3.03 (two d, 9-CH$_2$), 5.06 (s, CH=), 6.67 (s, H-8), 6.71 (d, H-6), 7.11 (br s, OH), and 7.48 (d, H-5).

-continued

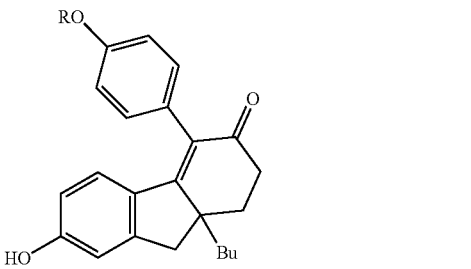

| | | |
|---|---|---|
| 50 | H<br>R = (CH$_3$)$_2$NCH$_2$CH$_2$<br>+ Cl$^-$ | 9a-butyl-4-{4-[2-(dimethylamino)ethoxy]phenyl}-7-hydroxy-1,2,9,9a-tetrahydro-3H-fluoren-3-one hydrochloride |

$^1$H NMR (DMSO-d$_6$, 500 MHz) δ 0.82 (t, CH$_2$CH$_2$CH$_2$CH$_3$), 1.23 (m, CH$_2$CH$_2$CH$_2$CH$_3$), 1.40 and 1.66 (two m, CH$_2$CH$_2$CH$_2$CH$_3$), 2.05 and 2.20 (two m, 1-CH$_2$), 2.37 and 2.57 (two m, 2-CH$_2$), 2.68 and 2.93 (two d, 9-CH$_2$), 2.86 (s, N(CH$_3$)$_2$), 3.51 (t, NCH$_2$CH$_2$O), 4.36 (t, NCH$_2$CH$_2$O), 6.17 (d, H-5), 6.35 (dd, H-6), 6.72 (d, H-8), 6.84–7.14 (br m, C$_6$H$_4$), 10.08 (s, OH0, and 10.22 (br s, NH); mass spectrum m/z 420.2 (M + 1 of free base).

| | | |
|---|---|---|
| 51 | H<br>R = (CH$_3$CH$_2$)$_2$NCH$_2$CH$_2$<br>+ Cl$^-$ | 9a-butyl-4-{4-[2-(diethylamino)ethoxy]-phenyl}-7-hydroxy-1,2,9,9a-tetrahydro-3H-fluoren-3-one hydrochloride |

$^1$H NMR (DMSO-d$_6$, 500 MHz) δ 1.26 (t, N(CH$_2$CH$_3$)$_2$), 3.24 (br m, N(CH$_2$CH$_3$)$_2$, 3.52 (br m, NCH$_2$CH$_2$O), 4.38 (t, NCH$_2$CH$_2$O), 6.83–7.10 (br m, C$_6$H$_4$), 9.99 (br s, NH), 10.06 (s, OH), 9a-CH$_2$CH$_2$CH$_2$CH$_3$, 1-CH$_2$, 2-CH$_2$, 9-CH$_2$, H-5, H-6 and H-8 are identical to previous compound.

| | | |
|---|---|---|
| 52 | 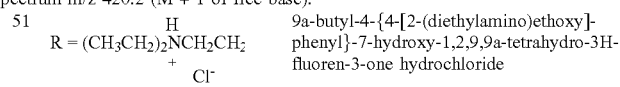 | 9a-butyl-7-hydroxy-4-{4-[2-(1-pyrrolidinyl)ethoxy]phenyl}-1,2,9,9a-tetrahydro-3H-fluoren-3-one hydrochloride |

$^1$H NMR (DMSO-d$_6$, 500 MHz) δ 1.90 and 2.03 (two br s, pyrrolidinyl 3-CH$_2$ and 4-CH$_2$), 3.13 (br s, NCH$_2$CH$_2$O), 3.59 (m, pyrrolidinyl 2-HC$_2$ and 5-CH$_2$), 4.35 (t, NCH$_2$CH$_2$O), 10.07 (s, OH0, 10.44 (br s, NH), 9a-CH$_2$CH$_2$CH$_2$CH$_3$, 1-CH$_2$, 2-CH$_2$, 9-CH$_2$, H-5, H-6, H-8 and C$_6$H$_4$ are identical to previous compound; mass spectrum m/z 446.2 (M + 1 of free base).

| | | |
|---|---|---|
| 53 | 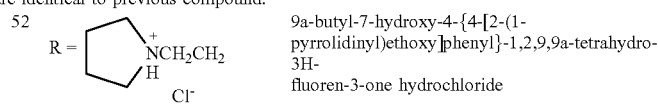 | 9a-butyl-7-hydroxy-4-{4-[2-(4-morpholinyl)ethoxy]phenyl}-1,2,9,9a-tetrahydro-3H-fluoren-3-one hydrochloride |

$^1$H NMR (DMSO-d$_6$, 500 MHz) δ 3.22 (br m, NCH$_2$CH$_2$O), 3.54 (br m, morpholinyl 3-CH$_2$ and 5-CH$_2$), 10.06 (s, OH), 10.83 (br s, NH), 9a-CH$_2$CH$_2$CH$_2$CH$_3$, 1-CH$_2$, 2-CH$_2$, 9-CH$_2$, NCH$_2$CH$_2$O, H-5, H-6, H-8 and C$_6$H$_4$ are identical to previous compound; mass spectrum m/z 462.3 (M + 1 of free base).

| | | |
|---|---|---|
| 54 | H<br>R = (CH$_3$)$_2$NCH$_2$CH$_2$CH$_2$<br>+ Cl$^-$ | 9a-butyl-4-{4-[3-(dimethylamino)propoxy]-phenyl}-7-hydroxy-1,2,9,9a-tetrahydro-3H-fluoren-3-one hydrochloride |

$^1$H NMR (DMSO-d$_6$, 500 MHz) δ 2.05 (m, 1-CH$_a$H$_b$), 2.12–2.23 (m, 1-CH$_a$H$_b$ and NCH$_2$CH$_2$CH$_2$O), 2.79 (s, N(CH$_3$)$_2$), 3.23 (t, NCH$_2$CH$_2$CH$_2$O), 4.08 (t, NCH$_2$CH$_2$CH$_2$O), 10.05 (s, OH), 10.23 (br s, NH), 9a-CH$_2$CH$_2$CH$_2$CH$_3$, 2-CH$_2$, 9-CH$_2$, H-5, H-6, H-8 and C$_6$H$_4$ are identical to previous compound; mass spectrum m/z 434.2 (M + 1 of free base).

| | | |
|---|---|---|
| 55 | 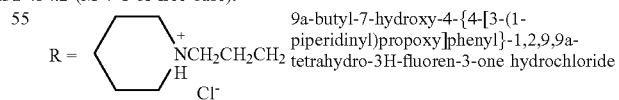 | 9a-butyl-7-hydroxy-4-{4-[3-(1-piperidinyl)propoxy]phenyl}-1,2,9,9a-tetrahydro-3H-fluoren-3-one hydrochloride |

$^1$H NMR (DMSO-d$_6$, 500 MHz) δ 1.40 (m, CH$_2$CH$_2$CH$_2$CH$_3$), 1.62–1.85 (m, piperidinyl 3-CH$_2$, 4-CH$_2$ and 5-CH$_2$), 2.05 (m, 1-CH$_a$H$_b$), 2.19 (m, 1-CH$_a$H$_b$ and NCH$_2$CH$_2$CH$_2$O), 2.89, 3.20, and 3.47 (three m, NCH$_2$CH$_2$CH$_2$O and piperidinyl 2-CH$_2$ and 6-CH$_2$), 4.08 (t, NCH$_2$CH$_2$CH$_2$O), 6.85–7.05 (br s, C$_6$H$_4$), 9.85 (br s, NH), 10.04 (s, OH), 9a-CH$_2$CH$_2$CH$_2$CH$_3$, 2-CH$_2$, 9-CH$_2$, H-5, H-6, and H-8 are identical to previous compound; mass spectrum m/z 474.2 (M + 1 of free base).

-continued

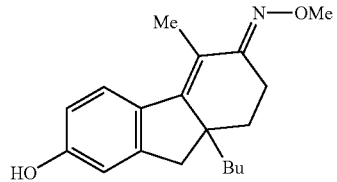

56 (3E)-9a-butyl-7-hydroxy-4-methyl-1,2,9,9a-tetrahydro-3H-fluoren-3-one O-methyloxime
$^1$H NMR (DMSO-d$_6$, 500 MHz) δ 0.77 (t, CH$_2$CH$_2$CH$_2$CH$_3$), 1.0–1.2 and 1.2–1.3 (two m, CH$_2$CH$_2$CH$_2$CH$_3$), 1.48 and 1.98 (two m, 1-CH$_2$), 2.03 (s, 4-CH$_3$), 2.23 and 2.72 (two m, 2-CH$_2$), 2.53 and 2.80 (two d, 9-CH$_2$), 3.83 (s, OCH$_3$), 6.65 (dd, H-6), 6.68 (s, H-8), 7.41 (d, H-5), and 9.64 (s, OH).

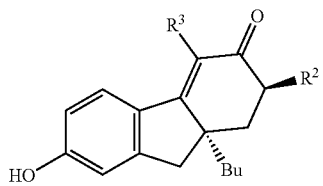

| 57 | $R^2$ = CH$_2$CH$_3$<br>$R^3$ = CH$_3$ | (2SR,9aSR)-9a-butyl-2-ethyl-7-hydroxy-4-methyl-1,2,9,9a-tetrahydro-3H-fluoren-3-one |

$^1$H NMR (CDCl$_3$, 400 MHz) δ 0.84 (t, CH$_2$CH$_2$CH$_2$CH$_3$), 0.93 (t, CH$_2$CH$_3$), 1.22, 1.35, 1.48, and 1.57 (four m, CH$_2$CH$_2$CH$_2$CH$_3$ and CH$_a$H$_b$CH$_3$), 1.66 and 2.30 (two dd, 1-CH$_2$), 2.02 (m, CH$_a$H$_b$CH$_3$), 2.06 (s, 4-CH$_3$), 2.36 (m, H-2), 2.68 and 2.84 (two d, 9-CH$_2$), 5.49 (br s, OH), 6.79 (dd, H-6), 6.81 (d, H-8), and 7.59 (d, H-5); mass spectrum m/z 299.1 (M + 1).

| 58 | $R^2$ = CH$_2$CH$_2$CH$_3$<br>$R^3$ = H | (2SR,9aSR)-9a-butyl-7-hydroxy-2-propyl-1,2,9,9a-tetrahydro-3H-fluoren-3-one |

$^1$H NMR (CDCl$_3$, 500 MHz) δ 0.84 (t, CH$_2$CH$_2$CH$_2$CH$_3$), 0.94 (t, CH$_2$CH$_2$CH$_3$), 1.18–1.47 (m, CH$_a$H$_b$CH$_2$CH$_2$CH$_3$ and CH$_a$H$_b$CH$_2$CH$_3$), 1.61 (m, CH$_a$H$_b$CH$_2$CH$_2$CH$_3$), 1.65 and 2.35 (two dd, 1-CH$_2$), 2.01 (m, CH$_a$H$_b$CH$_2$CH$_3$), 2.44 (m, H-2), 2.67 and 2.98 (two d, 9-CH$_2$), 6.12 (s, H-4), 6.22 (br s, OH), 6.87–6.91 (m, H-6 and H-8), and 7.43 (d, H-5); mass spectrum m/z 299.1 (M + 1).

| 59 | $R^2$ = CH$_2$CH$_2$CH$_3$<br>$R^3$ = CH$_3$ | (2SR,9aSR)-9a-butyl-7-hydroxy-4-methyl-2-propyl-1,2,9,9a-tetrahydro-3H-fluoren-3-one |

$^1$H NMR (CDCl$_3$, 500 MHz) δ 0.83 (t, CH$_2$CH$_2$CH$_2$CH$_3$), 0.94 (t, CH$_2$CH$_2$CH$_3$), 1.16–1.28 and 1.30–1.44 (two m, CH$_a$H$_b$CH$_2$CH$_2$CH$_3$ and CH$_a$H$_b$CH$_2$CH$_3$), 1.55 (m, CH$_a$H$_b$CH$_2$CH$_2$CH$_3$), 1.64 and 2.30 (two dd, 1-CH$_2$), 2.00 (m, CH$_a$H$_b$CH$_2$CH$_3$), 2.06 (s, 4-CH$_3$), 2.41 (m, H-2), 2.65 and 2.93 (two d, 9-CH$_2$), 5.08 (s, OH), 6.77 (dd, H-6), 6.79 (s, H-8), and 7.59 (d, H-5).

| 60 | $R^2$ = CH$_2$CH$_2$CH$_3$<br>$R^3$ = CH$_2$CH$_2$CH$_3$ | (2SR,9aSR)-4,9a-dibutyl-7-hydroxy-2-propyl-1,2,9,9a-tetrahydro-3H-fluoren-3-one |

$^1$H NMR (CDCl$_3$, 500 MHz) δ 0.83, 0.93 and 0.94 (three t, two CH$_2$CH$_2$CH$_2$CH$_3$ and CH$_2$CH$_2$CH$_3$), 1.22, 1.36, 1.42, and 1.51 (four m, 9a-CH$_2$CH$_2$CH$_2$CH$_3$, 4-CH$_2$CH$_2$CH$_2$CH$_3$, and CH$_a$H$_b$CH$_2$CH$_3$), 1.63 and 2.28 (two dd, 1-CH$_2$), 1.97 (m, CH$_a$H$_b$CH$_2$CH$_3$), 2.41 (m, H-2), 2.45 and 2.62 (two ddd, 4-CH$_2$CH$_2$CH$_2$CH$_3$), 2.66 and 2.94 (two d, 9-CH$_2$), 6.21 (s, OH), 6.79–6.84 (m, H-6 and H-8), and 7.52 (d, H-5).

| 61 | $R^2$ = CH$_2$CH$_2$CH$_3$<br>$R^3$ = Br | (2SR,9aSR)-9a-butyl-7-hydroxy-2-propyl-1,2,9,9a-tetrahydro-3H-fluoren-3-one |

$^1$H NMR (CDCl$_3$, 500 MHz) δ 0.84 (t, CH$_2$CH$_2$CH$_2$CH$_3$), 0.95 (t, CH$_2$CH$_2$CH$_3$), 1.18–1.30 and 1.32–1.49 (two m, CH$_a$H$_b$CH$_2$CH$_2$CH$_3$ and CH$_a$H$_b$CH$_3$), 1.63 (m, CH$_a$H$_b$CH$_2$CH$_2$CH$_3$), 1.75 and 2.33 (two dd, 1-CH$_2$), 2.04 (m, CH$_a$H$_b$CH$_2$CH$_3$), 2.61 (m, H-2), 2.74 and 2.98 (two d, 9-CH$_2$), 5.41 (s, OH), 6.80 (d, H-8), 6.83 (dd, H-6), and 8.43 (d, H-5); mass psectrum m/z 377 (M + 1) and 379 (M + 3).

| 62 | $R^2$ = CH$_2$CHO<br>$R^3$ = CH$_3$ | (2RS,9aSR)-9a-butyl-7-hydroxy-2-(2-oxoethyl)-1,2,9,9a-tetrahydro-3H-fluoren-3-one |

$^1$H NMR (CDCl$_3$, 500 MHz) δ 0.86 (t, CH$_2$CH$_2$CH$_2$CH$_3$), 1.26 and 1.38 (two m, CH$_a$H$_b$CH$_2$CH$_2$CH$_3$), 1.67 (m, CH$_a$H$_b$CH$_2$CH$_2$CH$_3$), 1.80 and 2.30 (two dd, 1-CH$_2$), 2.06 (s, 4-CH$_3$), 2.46 and 3.04 (two ddd, CH$_2$CHO), 2.65 and 2.94 (two d, 9-CH$_2$), 3.13 (m, H-2), 6.76–6.80 (m, H-6 and H-8), 7.60 (d, H-5), and 9.89 (s, OH); mass spectrum m/z 313.1 (M + 1).

| 63 | $R^2$ = CH$_2$CH$_2$CH$_2$CH$_3$<br>$R^3$ = CH$_3$ | (2SR,9aSR)-2,9a-dibutyl-7-hydroxy-4-methyl-1,2,9,9a-tetrahydro-3H-fluoren-3-one |

$^1$H NMR (CDCl$_3$, 500 MHz) δ 0.83 (t, 9a-CH$_2$CH$_2$CH$_2$CH$_3$), 0.91 (t, 2-CH$_2$CH$_2$CH$_2$CH$_3$), 1.17–1.44 (m, two CH$_a$H$_b$CH$_2$CH$_2$CH$_3$), 1.55 (m, 9a-CH$_a$H$_b$CH$_2$CH$_2$CH$_3$), 2.07 (s, 4-CH$_3$), 2.42 (m, H-2), 2.65 and 2.93 (two d, 9-CH$_2$), 6.30 (br s, OH), 6.82 (dd, H-6), 6.84 (s, H-8), and 7.59 (d, H-5); mass spectrum m/z 2327.2 (M + 1).

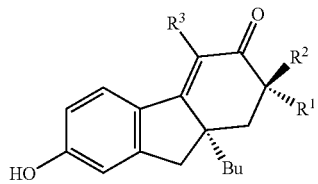

| 64 | $R^1$ = $CH_2CH_2CH_3$ | (2RS,9aRS)-9a-butyl-7-hydroxy-2,4-dimethyl-2- |
| --- | --- | --- |
|    | $R^2$ = $CH_3$ | propyl-1,2,9,9a-tetrahydro-3H-fluoren-3-one |
|    | $R^3$ = $CH_3$ | |

$^1$H NMR (CDCl$_3$, 500 MHz) δ 0.82 (t, CH$_2$CH$_2$CH$_2$CH$_3$), 0.95 (t, CH$_2$CH$_2$CH$_3$), 1.05 (s, 2-CH$_3$), 1.13–1.29 and 1.34–1.54 (two m, CH$_2$CH$_2$CH$_2$CH$_3$ and CH$_a$H$_b$CH$_2$CH$_3$), 1.61 and 2.41 (two d, 1-CH$_2$), 1.87 (m, CH$_a$H$_b$CH$_2$CH$_3$), 2.10 (s, 4-CH$_3$), 2.63 and 2.76 (two d, 9-CH$_2$), 5.14 (s, OH), 6.76–6.80 (m, H-6 and H-8), and 7.61 (d, H-5); mass spectrum m/z 327.2 (M + 1).

| 65 | $R^1$ = $CH_2CH_2CH_3$ | 9a-butyl-7-hydroxy-2,2-dipropyl-1,2,9,9a- |
| --- | --- | --- |
|    | $R^2$ = $CH_2CH_2CH_3$ | tetrahydro-3H-fluoren-3-one |
|    | $R^3$ = H | |

$^1$H NMR (CDCl$_3$, 500 MHz) δ 0.82, 0.83 and 0.94 (three t, CH$_2$CH$_2$CH$_2$CH$_3$ and two CH$_2$CH$_2$CH$_3$), 1.08, 1.21, 1.32, 1.43, and 1.54 (five m, CH$_2$CH$_2$CH$_2$CH$_3$, CH$_a$H$_b$CH$_2$CH$_3$, and CH$_2$CH$_2$CH$_3$), 1.74 and 2.30 (two d, 1-CH$_2$), 1.86 (m, CH$_a$H$_b$CH$_2$CH$_3$), 2.65 and 2.99 (two d, 9-CH$_2$), 5.82 (s, OH), 6.15 (s, H-4), 6.77 (m, H-6 and H-8), and 7.44 (m, H-5); mass spectrum m/z 341.1 (M + 1).

| 66 | $R^1$ = $CH_2CH_2CH_3$ | 9a-butyl-7-hydroxy-4-methyl-2,2-dipropyl- |
| --- | --- | --- |
|    | $R^2$ = $CH_2CH_2CH_3$ | 1,2,9,9a-tetrahydro-3H-fluoren-3-one |
|    | $R^3$ = $CH_3$ | |

$^1$H NMR (CDCl$_3$, 500 MHz) δ 0.79, 0.81 and 0.96 (three t, CH$_2$CH$_2$CH$_2$CH$_3$ and two CH$_2$CH$_2$CH$_3$), 1.09–1.68 (m, CH$_2$CH$_2$CH$_2$CH$_3$, CH$_a$H$_b$CH$_2$CH$_3$, and CH$_2$CH$_2$CH$_3$), 1.71 and 2.27 (two d, 1-CH$_2$), 1.92 (m, CH$_a$H$_b$CH$_2$CH$_3$), 2.08 (s, 4-CH$_3$), 2.67 and 2.96 (two d, 9-CH$_2$), 5.45 (s, OH), 6.76–6.80 (m, H-6 and H-8), and 7.60 (m, H-5); mass spectrum m/z 355.3 (M + 1).

| 67 | $R^1$ = $CH_2CH_2CH_3$ | (2SR,9aRS)-9a-butyl-2,7-dihydroxy-4-methyl-2- |
| --- | --- | --- |
|    | $R^2$ = OH | propyl-1,2,9,9a-tetrahydro-3H-fluoren-3-one |
|    | $R^3$ = $CH_3$ | |

$^1$H NMR (CDCl$_3$, 500 MHz) δ 0.86 (t, CH$_2$CH$_2$CH$_2$CH$_3$), 0.94 (t, CH$_2$CH$_2$CH$_3$), 1.23, 1.34, 1.53, 1.66, and 1.74 (five m, CH$_2$CH$_2$CH$_2$CH$_3$ and CH$_2$CH$_2$CH$_3$), 2.03 and 2.65 (two d, 1-CH$_2$), 2.10 (s, 4-CH$_3$), 2.64 and 2.98 (two d, 9-CH$_2$), 3.37 (s, OH), 5.41 (s, OH), 6.76–6.80 (m, H-6 and H-8), and 7.59 (d, H-5); mass spectrum m/z 329.1 (M + 1).

| 68 | $R^1$ = $CH_2CH_3$ | 4-bromo-9a-butyl-2,2-diethyl-7-hydroxy-1,2,9,9a- |
| --- | --- | --- |
|    | $R^2$ = $CH_2CH_3$ | tetrahydro-3H-fluoren-3-one |
|    | $R^3$ = Br | |

$^1$H NMR (CDCl$_3$, 500 MHz) δ 0.74, 0.80 and 0.98 (three t, CH$_2$CH$_2$CH$_2$CH$_3$ and two CH$_2$CH$_3$), 1.06–1.26 and 1.38–1.68 (two m, CH$_2$CH$_2$CH$_2$CH$_3$, CH$_a$H$_b$CH$_3$, and CH$_2$CH$_3$), 1.77 and 2.25 (two d, 1-CH$_2$), 2.03 (m, CH$_a$H$_b$CH$_3$), 2.77 and 3.00 (two d, 9-CH$_2$), 5.78 (s, OH), 6.81 (d, H-8), 6.85 (dd, H-6), and 8.45 (m, H-5); mass spectrum m/z 391.2 (M + 1) and 393.2 (M + 3).

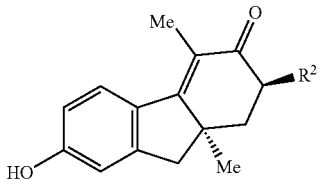

| 69 | $R^2$ = $CH_3$ | (2SR,9aSR)-7-hydroxy-2,4,9a-trimethyl-1,2,9,9a- |
| --- | --- | --- |
|    |    | tetrahydro-3H-fluoren-3-one |

$^1$H NMR (CDCl$_3$, 500 MHz) δ 1.12 (d, 2-CH$_3$), 1.14 (s, 9a-CH$_3$), 1.75 and 2.04 (two dd, 1-CH$_2$), 1.95 (s, 4-CH$_3$), 2.53 (m, H-2), 2.64 and 2.72 (two d, 9-CH$_2$), 6.69 (dd, H-6), 6.72 (s, H-8), and 7.48 (d, H-5); mass spectrum m/z 243.1 (M + 1).

| 70 | $R^2$ = $CH_2CH_2CH_3$ | (2SR,9aSR)-7-hydroxy-4,9a-dimethyl-2-propyl- |
| --- | --- | --- |
|    |    | 1,2,9,9a-tetrahydro-3H-fluoren-3-one |

$^1$H NMR (CDCl$_3$, 500 MHz) δ 0.94 (t, CH$_2$CH$_2$CH$_3$), 1.22 (s, 9a-CH$_3$), 1.31–1.44 (m, CH$_a$H$_b$CH$_2$CH$_3$), 1.79 and 2.17 (two dd, 1-CH$_2$), 2.01 (m, CH$_a$H$_b$CH$_2$CH$_3$), 2.06 (s, 4-CH$_3$), 2.50 (m, H-2), 2.75 and 2.84 (two d, 9-CH$_2$), 5.68 (br s, OH), 6.80 (dd, H-6), 6.84 (d, H-8), and 7.59 (d, H-5); mass spectrum m/z 271.1 (M + 1).

-continued

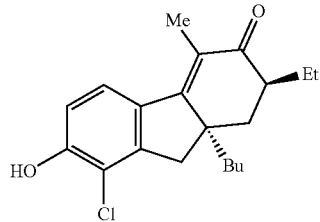

71 (2SR,9aSR)-9a-butyl-8-chloro-2-ethyl-7-hydroxy-4-methyl-1,2,9,9a-tetrahydro-3H-fluoren-3-one $^1$H NMR (CDCl$_3$, 400 MHz) δ 0.85 (t, CH$_2$CH$_2$CH$_2$CH$_3$), 0.94 (t, CH$_2$CH$_3$), 1.23, 1.37, 1.48, and 1.57 (four m, CH$_2$CH$_2$CH$_2$CH$_3$ and CH$_a$H$_b$CH$_3$), 1.69 and 2.33 (two dd, 1-CH$_2$), 2.01 (m, CH$_a$H$_b$CH$_3$), 2.05 (s, 4-CH$_3$), 2.37 (m, H-2), 2.68 and 3.05 (two d, 9-CH$_2$), 5.73 (s, OH), 6.99 (d, H-6), and 7.54 (d, H-5); mass spectrum m/z 333.1 (M + 1).

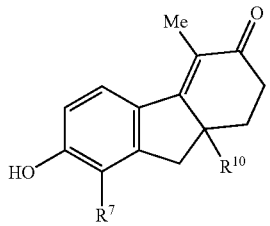

| | | |
|---|---|---|
| 72 | R$^7$ = Cl | 8-chloro-9a-ethyl-7-hydroxy-4-methyl-1,2,9,9a- |
| | R$^{10}$ = CH$_2$CH$_3$ | tetrahydro-3H-fluoren-3-one |

$^1$H NMR (CDCl$_3$, 500 MHz) δ 0.87 (t, CH$_2$CH$_3$), 1.49 and 1.63 (two dq, CH$_2$CH$_3$), 2.00 and 2.26 (two ddd, 1-CH$_2$), 2.06 (s, 4-CH$_3$), 2.48 and 2.57 (two ddd, 2-CH$_2$), 2.67 and 3.05 (two d, 9-CH$_2$), 5.75 (s, OH), 6.99 (d, H-6), and 7.55 (d, H-5).

| | | |
|---|---|---|
| 73 | R$^7$ = Br | 8-bromo-9a-ethyl-7-hydroxy-4-methyl-1,2,9,9a- |
| | R$^{10}$ = CH$_2$CH$_3$ | tetrahydro-3H-fluoren-3-one |

$^1$H NMR (CDCl$_3$, 500 MHz) δ 0.86 (t, CH$_2$CH$_3$), 1.50 and 1.61 (two dq, CH$_2$CH$_3$), 2.00 and 2.26 (two ddd, 1-CH$_2$), 2.06 (s, 4-CH$_3$), 2.48 and 2.57 (two ddd, 2-CH$_2$), 2.67 and 3.00 (two d, 9-CH$_2$), 5.85 (s, OH0, 6.99 (d, H-6), and 7.58 (d, H-5).

| | | |
|---|---|---|
| 74 | R$^7$ = CH$_3$ | 9a-ethyl-7-hydroxy-4,8-dimethyl-1,2,9,9a- |
| | R$^{10}$ = CH$_2$CH$_3$ | tetrahydro-3H-fluoren-3-one |

$^1$H NMR (CDCl$_3$, 500 MHz) δ 0.85 (t, CH$_2$CH$_3$), 1.47 and 1.62 (two dq, CH$_2$CH$_3$), 1.98 and 2.25 (two ddd, 1-CH$_2$), 2.06 (s, 4-CH$_3$), 2.19 (s, 8-CH$_3$), 2.47 and 2.58 (two ddd, 2-CH$_2$), 2.57 and 2.94 (two d, 9-CH$_2$), 5.45 (s, OH), 6.77 (d, H-6), and 7.46 (d, H-5).

| | | |
|---|---|---|
| 75 | R$^7$ = Cl | 8-chloro-7-hydroxy-4-methyl-9a-propyl-1,2,9,9a- |
| | R$^{10}$ = CH$_2$CH$_2$CH$_3$ | tetrahydro-3H-fluoren-3-one |

$^1$H NMR (CDCl$_3$, 500 MHz) δ 0.85 (t, CH$_2$CH$_2$CH$_3$), 1.13–1.32 (m, CH$_2$CH$_2$CH$_3$), 1.42 and 1.56 (two dt, CH$_2$CH$_2$CH$_3$), 2.01 and 2.25 (two ddd, 1-CH$_2$), 2.06 (s, 4-CH$_3$), 2.48 and 2.59 (two ddd, 2-CH$_2$), 2.70 and 3.05 (two d, 9-CH$_2$), 7.00 (d, H-6), and 7.55 (d, H-5); mass spectrum m/z 291.2 (M + 1).

| | | |
|---|---|---|
| 76 | R$^7$ = Br | 8-bromo-7-hydroxy-4-methyl-9a-propyl-1,2,9,9a- |
| | R$^{10}$ = CH$_2$CH$_2$CH$_3$ | tetrahydro-3H-fluoren-3-one |

$^1$H NMR (CDCl$_3$, 500 MHz) δ 0.84 (t, CH$_2$CH$_2$CH$_3$), 1.12–1.32 (m, CH$_2$CH$_2$CH$_3$), 1.43 and 1.56 (two dt, CH$_2$CH$_2$CH$_3$), 2.00 and 2.24 (two ddd, 1-CH$_2$), 2.06 (s, 4-CH$_3$), 2.48 and 2.59 (two ddd, 2-CH$_2$), 2.69 and 3.09 (two d, 9-CH$_2$), 5.86 (br s, OH), 6.99 (d, H-6), and 7.58 (d, H-5); mass spectrum m/z 335.3 (M + 1) and 337.3 (M + 3).

| | | |
|---|---|---|
| 77 | R$^7$ = CH$_3$ | 7-hydroxy-4,8-dimethyl-9a-propyl-1,2,9,9a- |
| | R$^{10}$ = CH$_2$CH$_2$CH$_3$ | tetrahydro-3H-fluoren-3-one |

$^1$H NMR (CDCl$_3$, 500 MHz) δ 0.83 (t, CH$_2$CH$_2$CH$_3$), 1.13–1.32 (m, CH$_2$CH$_2$CH$_3$), 1.41 and 1.55 (two dt, CH$_2$CH$_2$CH$_3$), 1.99 and 2.23 (two ddd, 1-CH$_2$), 2.06 (s, 4-CH$_3$), 2.19 (s, 8-CH$_3$), 2.48 and 2.60 (two ddd, 2-CH$_2$), 2.60 and 2.94 (two d, 9-CH$_2$), 5.67 (s, OH), 6.79 (d, H-6), and 7.47 (d, H-5); mass spectrum m/z 271.3 (M + 1).

| | | |
|---|---|---|
| 78 | R$^7$ = Cl | 8-chloro-7-hydroxy-4-methyl-9a-[(1E)-1- |
| | R$^{10}$ = (E)-CH=CHCH$_3$ | propenyl]-1,2,9,9a-tetrahydro-3H-fluoren-3-one |

$^1$H NMR (CDCl$_3$, 500 MHz) δ 1.57 (dd, CH=CHCH$_3$), 2.10 (s, 4-CH$_3$), 2.12 and 2.17 (two ddd, 1-CH$_2$), 2.43 and 2.54 (two ddd, 2-CH$_2$), 2.91 and 3.04 (two d, 9-CH$_2$), 5.25 (dq, CH=CHCH$_3$), 5.44 (dq, CH=CHCH$_3$), 7.00 (d, H-6), and 7.56 (d, H-5); mass spectrum m/z 289.4 (M + 1).

| | | |
|---|---|---|
| 779 | R$^7$ = Br | 8-bromo-9a-butyl-7-hydroxy-4-methyl-1,2,9,9a- |
| | R$^{10}$ = CH$_2$CH$_2$CH$_2$CH$_3$ | tetrahydro-3H-fluoren-3-one |

$^1$H NMR (DMSO-d$_6$, 500 MHz) δ 0.78 (t, CH$_2$CH$_2$CH$_2$CH$_3$), 1.07 and 1.18 (two m, CH$_2$CH$_2$CH$_2$CH$_3$), 1.30 and 1.54 (two m, CH$_2$CH$_2$CH$_2$CH$_3$), 1.92 (s, 4-CH$_3$), 1.95 and 2.14 (two m, 1-CH$_2$), 2.30 and 2.51 (two m, 2-CH$_2$), 2.65 and 2.90 (two d, 9-CH$_2$), 6.94 (d, H-6), and 7.55 (d, H-5).

| 80 | $R^7$ = $CH_3$<br>$R^{10}$ = $CH_2CH_2CH_2CH_3$ | 9a-butyl-7-hydroxy-4,8-dimethyl-1,2,9,9a-tetrahydro-3H-fluoren-3-one |

$^1$H NMR (DMSO-$d_6$, 500 MHz) δ 0.77 (t, $CH_2CH_2CH_2CH_3$), 1.16 (m, $CH_2CH_2CH_2CH_3$), 1.25 and 1.50 (two m, $CH_2CH_2CH_2CH_3$), 1.89 and 2.13 (two m, 1-$CH_2$), 1.90 (s, 4-$CH_3$), 2.04 (s, 8-$CH_3$), 2.27 and 2.47 (two m, 2-$CH_2$), 2.52 and 2.88 (two d, 9-$CH_2$), 6.79 (d, H-6), 7.38 (d, H-5), and 9.90 (s, OH).

| 81 | $R^7$ = $NO_2$<br>$R^{10}$ = $CH_2CH_2CH_2CH_3$ | 9a-butyl-7-hydroxy-4-methyl-8-nitro-1,2,9,9a-tetrahydro-3H-fluoren-3-one |

$^1$H NMR (DMSO-$d_6$, 500 MHz) δ 0.77 (t, $CH_2CH_2CH_2CH_3$), 1.05 and 1.16 (two m, $CH_2CH_2CH_2CH_3$), 1.31 and 1.53 (two m, $CH_2CH_2CH_2CH_3$), 1.93 (s, 4-$CH_3$), 1.96 and 2.13 (two m, 1-$CH_2$), 2.32 and 2.51 (two m, 2-$CH_2$), 2.83 and 2.99 (two d, 9-$CH_2$), 7.08 (d, H-6), and 7.80 (d, H-5).

| 82 | $R^7$ = $NH_2$<br>$R^{10}$ = $CH_2CH_2CH_2CH_3$ | 8-amino-9a-butyl-7-hydroxy-4-methyl-1,2,9,9a-tetrahydro-3H-fluoren-3-one |

$^1$H NMR (DMSO-$d_6$, 500 MHz) δ 0.79 (t, $CH_2CH_2CH_2CH_3$), 1.10–1.27 (m, $CH_aH_bCH_2CH_2CH_3$), 1.48 (m, $CH_aH_bCH_2CH_2CH_3$), 1.89 (s, 4-$CH_3$), 1.90 and 2.13 (two m, 1-$CH_2$), 2.27 and 2.46 (two m, 2-$CH_2$), 2.34 and 2.87 (two d, 9-$CH_2$), 6.69 (d, H-6 or H-5), and 6.88 (d, H-5 or H-6).

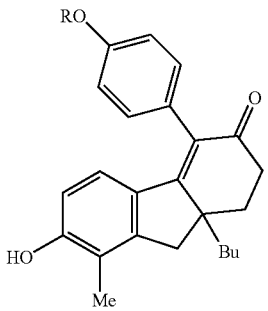

| 83 | R = H | 9a-butyl-7-hydroxy-4-(4-hydroxyphenyl)-8-methyl-1,2,9,9a-tetrahydro-3H-fluoren-3-one |

$^1$H NMR (CDCl$_3$, 500 MHz) δ 0.87 (t, $CH_2CH_2CH_2CH_3$), 1.27 (m, $CH_2CH_2CH_2CH_3$), 1.51 and 1.70 (two m, $CH_2CH_2CH_2CH_3$), 2.08 and 2.31 (two m, 1-$CH_2$), 2.13 (s, 8-$CH_3$), 2.59 and 2.71 (two m, 2-$CH_2$), 2.61 and 2.97 (two d, 9-$CH_2$), 6.09 (d, H-6 or H-5), 6.29 (d, H-5 or H-6), 6.71 (s, OH), 6.74–6.88 (br m, $C_6H_4$), and 7.36 (s, OH); mass spectrum m/z 363.2 (M + 1).

| 84 | R = cyclohexyl-$NCH_2CH_2$ | 9a-butyl-7-hydroxy-8-methyl-4-{4-[2-piperidinyl)-ethoxy]phenyl}-1,2,9,9a-tetrahydro-3H-fluoren-3-one |

$^1$H NMR (CDCl$_3$, 500 MHz) δ 0.87 (t, $CH_2CH_2CH_2CH_3$), 1.23–1.36, 1.43–1.51, and 1.61–1.69 (three m, $CH_2CH_2CH_2CH_3$, piperidinyl 3-$CH_2$, 4-$CH_2$ and 5-$CH_2$), 1.52 and 1.72 (two m, $CH_2CH_2CH_2CH_3$), 2.10 and 2.31 (two m, 1-$HC_2$), 2.13 (s, 8-$CH_3$), 2.51–2.71 (m, 2-$CH_2$ and piperidinyl N($CH_2$)$_2$), 2.64 and 2.97 (two d, 9-$CH_2$), 2.83 (t, N$CH_2$$CH_2$O), 4.10 (m, N$CH_2$$CH_2$O), 6.19 (d, H-6 or H-5), 6.37 (d, H-5 or H-6), 6.67–7.16 (br m, $C_6H_4$), and 7.36 (s, OH); mass spectrum m/z 474.2 (M + 1).

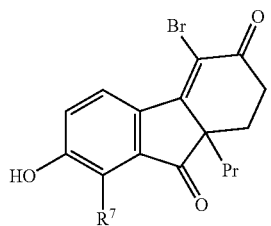

| 85 | $R^7$ = H | 4-bromo-7-hydroxy-9a-propyl-1H-fluorene-3,9(2H,9aH)-dione |

$^1$H NMR (DMSO-$d_6$, 500 MHz) δ 0.71 (t, $CH_2CH_2CH_3$), 0.97 (m, $CH_2CH_2CH_3$), 1.68 and 1.79 (two ddd, $CH_2CH_2CH_3$), 1.99 and 2.16 (two ddd, 1-$CH_2$), 2.62 and 2.94 (two ddd, 2-$CH_2$), 7.12 (d, H-8), 7.34 (dd, H-6), and 8.56 (d, H-5).

| 86 | $R^7$ = Br | 4,8-dibromo-7-hydroxy-9a-propyl-1H-fluorene-3,9(2H,9aH)-dione |

$^1$H NMR (CDCl$_3$, 500 MHz) δ 0.80 (t, $CH_2CH_2CH_3$), 1.10 (m, $CH_2CH_2CH_3$), 1.73 and 1.86 (two m, $CH_2CH_2CH_3$), 2.01 and 2.41 (two ddd, 1-$CH_2$), 2.80 and 2.90 (two ddd, 2-$CH_2$), 6.47 (br s, OH), 7.46 (d, H-6), and 8.72 (d, H-5).

-continued

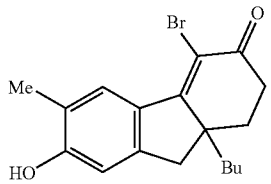

87  4-bromo-9a-butyl-7-hydroxy-6-methyl-1,2,9,9a-tetrahydro-3H-fluoren-3-one
$^1$H NMR (CDCl$_3$, 500 MHz) δ 0.84 (t, CH$_2$CH$_2$CH$_2$CH$_3$), 1.14–1.30 (m, CH$_2$CH$_2$CH$_2$CH$_3$), 1.45 and 1.63 (two m, CH$_2$CH$_2$CH$_2$CH$_3$), 2.04 and 2.23 (two ddd, 1-CH$_2$), 2.31 (s, 6-CH$_3$), 2.66–2.79 (m, 2-CH$_2$), 2.73 and 2.96 (two d, 9-CH$_2$), 5.59 (s, OH), 6.77 (s, H-8), and 8.36 (s, H-5); mass spectrum m/z 349.0 (M + 1) and 351.0 (M + 3).

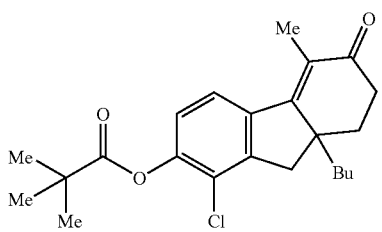

88  9a-butyl-8-chloro-4-methyl-3-oxo-2,3,9,9a-tetrahydro-1H-fluoren-7-yl pivalate
$^1$H NMR (CDCl$_3$, 500 MHz) δ 0.85 (t, CH$_2$CH$_2$CH$_2$CH$_3$), 1.16–1.29 (m, CH$_2$CH$_2$CH$_2$CH$_3$), 1.40 and 1.58 (two m, CH$_2$CH$_2$CH$_2$CH$_3$), 1.41 (s, C(CH$_3$)$_3$), 2.01 and 2.28 (two ddd, 1-CH$_2$), 2.49 and 2.59 (two ddd, 2-CH$_2$), 2.71 and 3.10 (two d, 9-CH$_2$), 7.07 (d, H-6), and 7.60 (d, H-5).

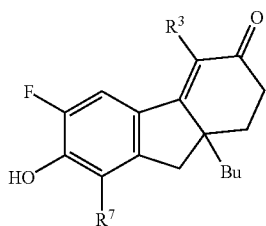

89  R$^3$ = CH$_3$   9a-butyl-6,8-difluoro-7-hydroxy-4-methyl-
    R$^7$ = F      1,2,9,9a-tetrahydro-3H-fluoren-3-one
$^1$H NMR (CDCl$_3$, 500 MHz) δ 0.85 (t, CH$_2$CH$_2$CH$_2$CH$_3$), 1.13–1.29 (m, CH$_2$CH$_2$CH$_2$CH$_3$), 1.37 and 1.57 (two m, CH$_2$CH$_2$CH$_2$CH$_3$), 1.99 and 2.25 (two ddd, 1-CH$_2$), 2.04 (s, 4-CH$_3$), 2.48 and 2.57 (two ddd, 2-CH$_2$), 2.62 and 3.07 (two d, 9-CH$_2$), 5.36 (s, OH), and 7.28 (dd, H-5); mass spectrum m/z 307.4 (M + 1).

90  R$^3$ = CH$_2$CH$_3$   9a-butyl-4-ethyl-6,8-difluoro-7-hydroxy-1,2,9,9a-
    R$^7$ = F           tetrahydro-3H-fluoren-3-one
$^1$H NMR (CDCl$_3$, 500 MHz) δ 0.85 (t, CH$_2$CH$_2$CH$_2$CH$_3$), 1.09 (t, CH$_2$CH$_3$), 1.14–1.30 (m, CH$_2$CH$_2$CH$_2$CH$_3$), 1.38 and 1.55 (two m, CH$_2$CH$_2$CH$_2$CH$_3$), 1.97 and 2.24 (two ddd, 1-CH$_2$), 2.41 and 2.63 (two dq, CH$_2$CH$_3$), 2.47 and 2.56 (two ddd, 2-CH$_2$), 2.61 and 3.06 (two d, 9-CH$_2$), 6.01 (s, OH), and 7.23 (dd, H-5); mass spectrum m/z 321.2 (M + 1).

91  R$^3$ = Br   4-bromo-9a-butyl-6,8-difluoro-7-hydroxy-
    R$^7$ = F    1,2,9,9a-tetrahydro-3H-fluoren-3-one
$^1$H NMR (CDCl$_3$, 500 MHz) δ 0.86 (t, CH$_2$CH$_2$CH$_2$CH$_3$), 1.13–1.31 (m, CH$_2$CH$_2$CH$_2$CH$_3$), 1.47 and 1.63 (two m, CH$_2$CH$_2$CH$_2$CH$_3$), 2.09 and 2.29 (two ddd, 1-CH$_2$), 2.70–2.79 (m, 2-CH$_2$), 2.71 and 3.12 (two d, 9-CH$_2$), 5.73 (s, OH), and 8.17 (dd, H-5).

92  R$^3$ = Cl   8-bromo-9a-butyl-4-chloro-8-difluoro-7-hydroxy-
    R$^7$ = Br   1,2,9,9a-tetrahydro-3H-fluoren-3-one
$^1$H NMR (CDCl$_3$, 500 MHz) δ 0.86 (t, CH$_2$CH$_2$CH$_2$CH$_3$), 1.13–1.31 (m, CH$_2$CH$_2$CH$_2$CH$_3$), 1.50 and 1.65 (two m, CH$_2$CH$_2$CH$_2$CH$_3$), 2.09 and 2.29 (two ddd, 1-CH$_2$), 2.66–2.74 (m, 2-CH$_2$), 2.74 and 3.05 (two d, 9-CH$_2$), 5.88 (s, OH), and 8.10 (dd, H-5).

93  R$^3$ = Br   9a-butyl-4,8-dibromo-6-fluoro-7-hydroxy-
    R$^7$ = Br   1,2,9,9a-tetrahydro-3H-fluoren-3-one
$^1$H NMR (CDCl$_3$, 500 MHz) δ 0.86 (t, CH$_2$CH$_2$CH$_2$CH$_3$), 1.13–1.30 (m, CH$_2$CH$_2$CH$_2$CH$_3$), 1.51 and 1.64 (two m, CH$_2$CH$_2$CH$_2$CH$_3$), 2.09 and 2.29 (two ddd, 1-CH$_2$), 2.69–2.80 (m, 2-CH$_2$), 2.73 and 3.04 (two d, 9-CH$_2$), 5.88 (d, OH), and 8.32 (d, H-5).

-continued

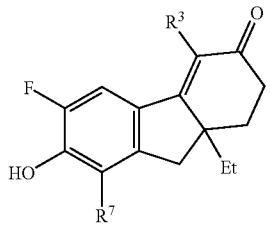

| | | |
|---|---|---|
| 94 | R³ = CH₃<br>R⁷ = H | 9a-ethyl-6-fluoro-7-hydroxy-4-methyl-1,2,9,9a-tetrahydro-3H-fluoren-3-one |

¹H NMR (CDCl₃, 500 MHz) δ 0.85 (t, CH₂CH₃), 1.47 and 1.61 (two dq, CH₂CH₃), 1.97 and 2.23 (two ddd, 1-CH₂), 2.05 (s, 4-CH₃), 2.47 and 2.56 (two ddd, 2-CH₂), 2.65 and 2.92 (two d, 9-CH₂), 5.38 (d, OH), 6.95 (d, H-8), and 7.43 (d, H-5); mass spectrum m/z 261.2 (M + 1).

| | | |
|---|---|---|
| 95 | R³ = CH₃<br>R⁷ = F | 9a-ethyl-6,8-difluoro-7-hydroxy-4-methyl-1,2,9,9a-tetrahydro-3H-fluoren-3-one |

¹H NMR (CDCl₃, 500 MHz) δ 0.87 (t, CH₂CH₃), 1.47 and 1.61 (two dq, CH₂CH₃), 1.99 and 2.26 (two ddd, 1-CH₂), 2.04 (s, 4-CH₃), 2.48 and 2.56 (two ddd, 2-CH₂), 2.61 and 3.07 (two d, 9-CH₂), 5.41 (s, OH), and 7.28 (d, H-5).

| | | |
|---|---|---|
| 96 | R³ = CH₃<br>R⁷ = Cl | 8-chloro-9a-ethyl-6-fluoro-7-hydroxy-4-methyl-1,2,9,9a-tetrahydro-3H-fluoren-3-one |

¹H NMR (CDCl₃, 500 MHz) δ 0.86 (t, CH₂CH₃), 1.48 and 1.62 (two dq, CH₂CH₃), 1.99 and 2.27 (two ddd, 1-CH₂), 2.04 (s, 4-CH₃), 2.48 and 2.57 (two ddd, 2-CH₂), 2.64 and 3.03 (two d, 9-CH₂), 5.68 (s, OH), and 7.40 (d, H-5); mass spectrum m/z 295.3 (M + 1).

| | | |
|---|---|---|
| 97 | R³ = CH₃<br>R⁷ = Br | 8-bromo-9a-ethyl-6-fluoro-7-hydroxy-4-methyl-1,2,9,9a-tetrahydro-3H-fluoren-3-one |

¹H NMR (CDCl₃, 500 MHz) δ 0.86 (t, CH₂CH₃), 1.49 and 1.62 (two dq, CH₂CH₃), 1.99 and 2.26 (two ddd, 1-CH₂), 2.04 (s, 4-CH₃), 2.48 and 2.57 (two ddd, 2-CH₂), 2.64 and 2.99 (two d, 9-CH₂), 5.96 (d, OH), and 7.43 (d, H-5).

| | | |
|---|---|---|
| 98 | R³ = CH₃<br>R⁷ = CH₃ | 9a-ethyl-6-fluoro-7-hydroxy-4,8-dimethyl-1,2,9,9a-tetrahydro-3H-fluoren-3-one |

¹H NMR (CDCl₃, 500 MHz) δ 0.85 (t, CH₂CH₃), 1.09 (t, 4-CH₂CH₃), 1.48 and 1.60 (two dq, 9a-CH₂CH₃), 1.98 and 2.25 (two ddd, 1-CH₂), 2.42 and 2.63 (two m, 4-CH₂CH₃), 2.46 and 2.54 (two ddd, 2-CH₂), 2.60 and 3.06 (two d, 9-CH₂), 5.39 (t, OH), and 7.24 (d, H-5); mass spectrum m/z 293.3 (M + 1).

| | | |
|---|---|---|
| 100 | R³ = Br<br>R⁷ = Cl | 4-bromo-8-chloro-9a-ethyl-6-fluoro-7-hydroxy-1,2,9,9a-tetrahydro-3H-fluoren-3-one |

¹H NMR (CDCl₃, 500 MHz) δ 0.89 (t, CH₂CH₃), 1.58 and 1.69 (two dq, CH₂CH₃), 2.09 and 2.30 (two m, 1-CH₂), 2.69–2.79 (m, 2-CH₂), 2.73 and 3.08 (two d, 9-CH₂), 5.93 (br s, OH), and 8.29 (d, H-5); mass spectrum m/z 359.2 (M + 1), 361.2 (M + 3).

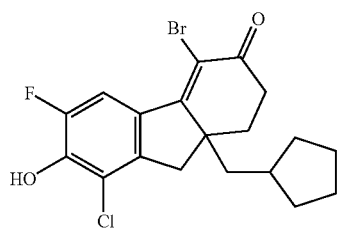

| | |
|---|---|
| 101 | 4-bromo-8-chloro-9a-(cyclopentylmethyl)-6-fluoro-7-hydroxy-1,2,9,9a-tetrahydro-3H-fluoren-3-one |

¹H NMR (CDCl₃, 500 MHz) δ 0.94–1.12, 1.38–1.49, 1.51–1.69, and 1.71–1.79 (four m, cyclopentylmethyl), 2.11 and 2.31 (two ddd, 1-CH₂), 2.72 and 2.81 (two ddd, 2-CH₂), 2.76 and 3.17 (two d, 9-CH₂), 5.97 (d, OH), and 8.29 (d, H-5).

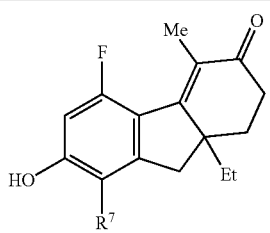

| | | |
|---|---|---|
| 102 | R⁷ = H | 9a-ethyl-5-fluoro-7-hydroxy-4-methyl-1,2,9,9a-tetrahydro-3H-fluoren-3-one |

¹H NMR (CDCl₃, 500 MHz) δ 0.85 (t, CH₂CH₃), 1.42 and 1.64 (two dq, CH₂CH₃), 1.96 (d, 4-CH₃), 1.96 and 2.21 (two ddd, 1-CH₂), 2.44 and 2.54 (two ddd, 2-CH₂), -continued 2.67 and 2.90 (two d, 9-CH$_2$), 5.81 (br s, OH), 6.46 (dd, H-6), and 6.59 (s, H-8); mass spectrum m/z 261.2 (M + 1).

| 103 | R$^7$ = Br | 8-bromo-9a-ethyl-5-fluoro-7-hydroxy-4-methyl-1,2,9,9a-tetrahydro-3H-fluoren-3-one |

$^1$H NMR (CDCl$_3$, 500 MHz) δ 0.86 (t, CH$_2$CH$_3$), 1.46 and 1.67 (two dq, CH$_2$CH$_3$), 1.94 (d, 4-CH$_3$), 1.99 and 2.25 (two ddd, 1-CH$_2$), 2.46 and 2.55 (two ddd, 2-CH$_2$), 2.68 and 2.98 (two d, 9-CH$_2$), 5.82 (d, OH), and 6.70 (d, H-6).

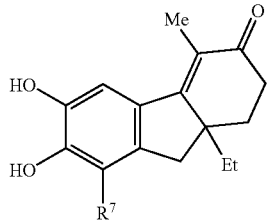

| 104 | R$^7$ = H | 9a-ethyl-6,7-dihydroxy-4-methyl-1,2,9,9a-tetrahydro-3H-fluoren-3-one |

$^1$H NMR (CDCl$_3$, 500 MHz) δ 0.86 (t, CH$_2$CH$_3$), 1.48 and 1.61 (two dq, CH$_2$CH$_3$), 1.97 and 2.22 (two ddd, 1-CH$_2$), 2.10 (s, 4-CH$_3$), 2.49 and 2.60 (two ddd, 2-CH$_2$), 2.64 and 2.89 (two d, 9-CH$_2$), 5.91 (br s, OH), 6.86 (s, H-5 or H-8), 6.94 (br s, OH), and 7.43 (s, H-8 or H-5).

| 105 | R$^7$ = Br | 8-bromo-9a-ethyl-6,7-dihydroxy-4-methyl-1,2,9,9a-tetrahydro-3H-fluoren-3-one |

$^1$H NMR (CDCl$_3$, 500 MHz) δ 0.85 (t, CH$_2$CH$_3$), 1.49 and 1.61 (two dq, CH$_2$CH$_3$), 1.98 and 2.24 (two ddd, 1-CH$_2$), 2.06 (s, 4-CH$_3$), 2.47 and 2.56 (two ddd, 2-CH$_2$), 2.62 and 2.93 (two d, 9-CH$_2$), and 7.28 (s, H-5).

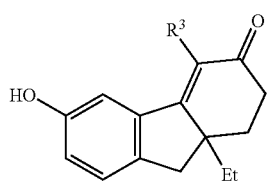

| 106 | R$^3$ = CH$_3$ | 9a-ethyl-6-hydroxy-4-methyl-1,2,9,9a-tetrahydro-3H-fluoren-3-one |

$^1$H NMR (CDCl$_3$, 500 MHz) δ 0.86 (t, CH$_2$CH$_3$), 1.48 and 1.60 (two dq, CH$_2$CH$_3$), 1.99 and 2.24 (two ddd, 1-CH$_2$), 2.11 (s, 4-CH$_3$), 2.49 and 2.59 (two ddd, 2-CH$_2$), 2.64 and 2.92 (two d, 9-CH$_2$), 6.01 (s, OH), 6.89 (dd, H-7), 7.18 (d, H-8), and 7.29 (d, H-5).

| 107 | R$^3$ = CH=CH$_2$ | 9a-ethyl-6-hydroxy-4-vinyl-1,2,9,9a-tetrahydro-3H-fluoren-3-one |

$^1$H NMR (CDCl$_3$, 500 MHz) δ 0.86 (t, CH$_2$CH$_3$), 1.49 and 1.63 (two dq, CH$_2$CH$_3$), 2.01 and 2.23 (two ddd, 1-CH$_2$), 2.51 and 2.61 (two ddd, 2-CH$_2$), 2.66 and 2.92 (two d, 9-CH$_2$), 5.53 (dd, cis CH=CH$_a$H$_b$), 5.63 (s, OH), 5.82 (dd, trans CH=CH$_a$H$_b$), 6.53 (dd, CH=CH$_a$H$_b$), 6.89 (dd, H-7), 7.17 (d, H-8), and 7.32 (d, H-5).

| 108 | R$^3$ = CH$_2$CH=CH$_2$ | 4-allyl-9a-ethyl-6-hydroxy-1,2,9,9a-tetrahydro-3H-fluoren-3-one |

$^1$H NMR (CDCl$_3$, 500 MHz) δ 0.87 (t, CH$_2$CH$_3$), 1.53 and 1.66 (two dq, CH$_2$CH$_3$), 2.01 and 2.25 (two ddd, 1-CH$_2$), 2.49 and 2.60 (two ddd, 2-CH$_2$), 2.66 and 2.73 (two d, 9-CH$_2$), 3.13 and 3.49 (two m, CH$_2$CH=CH$_2$), 5.00–5.07 (m, CH=CH$_2$), 5.18 (s, OH), 5.98 (m, CH=CH$_2$), 6.87 (dd, H-7), 7.13 (d, H-5), and 7.17 (d, H-8).

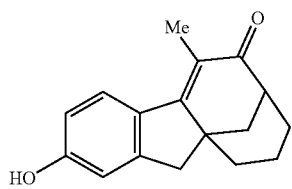

| 109 | | 2-hydroxy-5-methyl-7,8,9,10-tetrahydro-7,10a-methanocyclooctal[a]inden-6(11H)-one |

$^1$H NMR (2:1 CDCl$_3$-CD$_3$CN, 500 MHz) δ 1.30–1.46 (m, 9-CH$_2$, 10-CH$_2$, and 8-CH$_a$H$_b$,), 1.64 (m, 8-CH$_a$H$_b$), 1.85 and 2.11 (dd and m, 12-CH$_2$), 1.98 (s, 5-CH$_3$), 2.52 (m, H-7), 2.55 and 2.74 (two d, 11-CH$_2$), 6.66 (d, H-3), 6.68 (s, H-1), 7.28 (s, CHCl$_3$), and 7.47 (d, H-4); mass spectrum m/z 255.3 (M + 1).

-continued

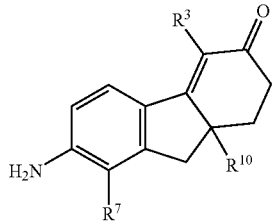

| | | |
|---|---|---|
| 110 | R³ = Br | 7-amino-4-bromo-9a-butyl-1,2,9,9a-tetrahydro- |
| | R⁷ = H | 3H-fluoren-3-one |
| | R¹⁰ = CH₂CH₂CH₂CH₃ | |

$^1$H NMR (DMSO-d$_6$, 500 MHz) δ 0.79 (t, CH₂CH₂CH₂CH₃), 1.04–1.27 (m, CH₂CH₂CH₂CH₃), 1.32 and 1.57 (two m, CH₂CH₂CH₂CH₃), 1.96 and 2.09 (two m, 1-CH₂), 2.48 and 2.65 (two m, 2-CH₂), 2.64 and 2.85 (two d, 9-CH₂), 6.14 (s, NH₂), 6.51 (s, H-8), 6.55 (dd, H-6), and 8.13 (d, H-5).

| | | |
|---|---|---|
| 111 | R³ = CH₃ | 7-amino-4,8-dibromo-9a-ethyl-1,2,9,9a- |
| | R⁷ = Br | tetrahydro-3H-fluoren-3-one |
| | R¹⁰ = CH₂CH₃ | |

$^1$H NMR (CDCl₃, 500 MHz) δ 0.86 (t, CH₂CH₃), 1.50 and 1.63 (two dq, CH₂CH₃), 1.98 and 2.24 (two ddd, 1-CH₂), 2.05 (s, 4-CH₃), 2.46 and 2.56 (two ddd, 2-CH₂), 2.61 and 2.99 (two d, 9-CH₂), 4.42 (s, NH₂), 6.70 (d, H-6), and 7.48 (d, H-5).

EXAMPLE 112

The following compounds are prepared using methods analogous to those described in the preceding examples:

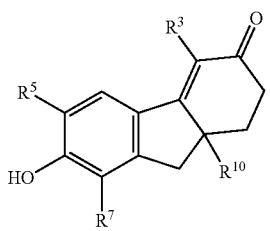

| R³ | R⁵ | R⁷ | R¹⁰ |
|---|---|---|---|
| CH₃ | H | OH | CH₂CH₂CH₂CH₃ |
| CH₂CH₃ | H | OH | CH₂CH₂CH₂CH₃ |
| CH₃ | H | F | CH₂CH₂CH₂CH₃ |
| CH₂CH₃ | H | F | CH₂CH₂CH₂CH₃ |
| CHF₂ | H | F | CH₂CH₂CH₂CH₃ |
| CF₃ | H | F | CH₂CH₂CH₂CH₃ |
| CF₂CH₃ | H | F | CH₂CH₂CH₂CH₃ |
| CN | H | F | CH₂CH₂CH₂CH₃ |
| C(=O)CH₃ | H | F | CH₂CH₂CH₂CH₃ |
| CHF₂ | F | Cl | CH₂CH₃ |
| CF₃ | F | Cl | CH₂CH₃ |
| CF₂CH₃ | F | Cl | CH₂CH₃ |
| CN | F | Cl | CH₂CH₃ |
| C(=O)CH₃ | F | Cl | CH₂CH₃ |
| Cl | F | Cl | CH₂CH₃ |
| CH₃ | F | Cl | CH₂CH₂CH₃ |
| CH₂CH₃ | F | Cl | CH₂CH₂CH₃ |
| CH₂CH₂CH₃ | F | Cl | CH₂CH₂CH₃ |
| CHF₂ | F | Cl | CH₂CH₂CH₃ |
| CF₃ | F | Cl | CH₂CH₂CH₃ |
| CF₂CH₃ | F | Cl | CH₂CH₂CH₃ |
| CN | F | Cl | CH₂CH₂CH₃ |
| C(=O)CH₃ | F | Cl | CH₂CH₂CH₃ |
| Cl | F | Cl | CH₂CH₂CH₃ |
| Br | F | Cl | CH₂CH₂CH₃ |
| CHF₂ | F | Cl | CH₂CH₂CH₂CH₃ |
| CF₂CH₃ | F | Cl | CH₂CH₂CH₂CH₃ |
| CN | F | Cl | CH₂CH₂CH₂CH₃ |
| C(=O)CH₃ | F | Cl | CH₂CH₂CH₂CH₃ |
| C(=O)CH₂CH₃ | F | Cl | CH₂CH₂CH₂CH₃ |
| C(=O)OCH₃ | F | Cl | CH₂CH₂CH₂CH₃ |
| Cl | F | Cl | CH₂CH₂CH₂CH₃ |
| CH₂CH₃ | H | CHF₂ | CH₂CH₂CH₂CH₃ |
| CH₂CH₃ | F | CHF₂ | CH₂CH₂CH₂CH₃ |
| CF₃ | F | Cl | CH₂CH₂CH₂CH₃ |
| CF₃ | F | Cl | CH₂CH₂CH₂CH₃ |
| CF₃ | F | Cl | CH₂-cyclopentyl |
| CF₃ | F | Cl | CH₂-cyclohexyl |

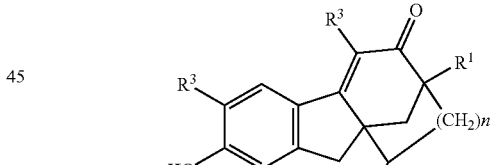

| n | R | R¹ | R³ | R⁵ | R⁷ |
|---|---|---|---|---|---|
| 1 | CH₂CH₂CH₃ | H | CH₃ | H | H |
| 1 | CH₂CH₂CH₃ | H | CH₂CH₃ | H | H |
| 1 | CH₂CH₂CH₃ | H | Br | H | H |
| 1 | CH₂CH₂CH₃ | H | CF₃ | H | H |
| 1 | CH₂CH₂CH₃ | CH₃ | CH₂CH₃ | H | H |
| 1 | CH₂CH₂CH₃ | CH₂CH₂CH₃ | CH₂CH₃ | H | H |
| 1 | CH₂CH₂CH₃ | OH | CH₂CH₃ | H | H |
| 1 | CH₂CH₂CH₃ | H | CF₃ | F | Cl |
| 2 | CH₂CH₃ | H | CH₂CH₃ | H | H |
| 2 | CH₂CH₃ | H | Br | H | H |
| 2 | CH₂CH₃ | H | CF₃ | H | H |
| 2 | CH₂CH₃ | H | CF₃ | F | Cl |
| 2 | CH₂CH₂CH₃ | H | CH₃ | H | H |
| 2 | CH₂CH₂CH₃ | H | CF₃ | H | H |

Estrogen Receptor Binding Assay

The estrogen receptor ligand binding assays are designed as scintillation proximity assays employing the use of tritiated estradiol and recombinant expressed estrogen receptors. The full length recombinant human ER-α and ER-β proteins are produced in a bacculoviral expression system. ER-α or ER-β extracts are diluted 1:400 in phosphate buffered saline containing 6 mM α-monothiolglycerol. 200 μL aliquots of the diluted receptor preparation are added to each well of a 96-well Flashplate. Plates are covered with Saran Wrap and incubated at 4° C. overnight.

The following morning, a 20 ul aliquot of phosphate buffered saline containing 10% bovine serum albumin is added to each well of the 96 well plate and allowed to incubate at 4° C. for 2 hours. Then the plates are washed with 200 ul of buffer containing 20 mM Tris (pH 7.2), 1 mM EDTA, 10% Glycerol, 50 mM KCl, and 6 mM α-monothiolglycerol. To set up the assay in these receptor coated plates, add 178 ul of the same buffer to each well of the 96 well plate. Then add 20 ul of a 10 nM solution of $^3$H-estradiol to each well of the plate.

Test compounds are evaluated over a range of concentrations from 0.01 nM to 1000 nM. The test compound stock solutions should be made in 100% DMSO at 100× the final concentration desired for testing in the assay. The amount of DMSO in the test wells of the 96 well plate should not exceed 1%. The final addition to the assay plate is a 2 ul aliquot of the test compound which has been made up in 100% DMSO. Seal the plates and allow them to equilibrate at room temperature for 3 hours. Count the plates in a scintillation counter equipped for counting 96 well plates.

The compounds of Examples 1–111 exhibit binding affinities to the estrogen receptor α-subtype in the range of $IC_{50}$=2.8–5625 nm, and to the estrogen receptor β-subtype in the range of $IC_{50}$=0.6–126 nm.

Pharmaceutical Composition

As a specific embodiment of this invention, 25 mg of tetrahydrofluorenone from Example 17, is formulated with sufficient finely divided lactose to provide a total amount of 580 to 590 mg to fill a size 0, hard-gelatin capsule.

What is claimed is:
1. A compound of the formula:

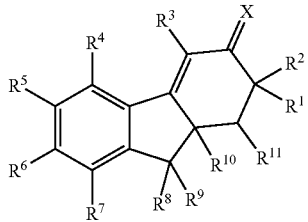

wherein X is selected from the group consisting of: O, N—OR$^a$, N—NR$^a$R$^b$ and $C_{1-6}$ alkylidene, wherein said alkylidene group is unsubstituted or substituted with a group selected from hydroxy, amino, O($C_{1-4}$alkyl), NH($C_{1-4}$alkyl), or N($C_{1-4}$alkyl)$_2$;

R$^1$ is selected from the group consisting of hydrogen, $C_{1-6}$alkyl, $C_{2-6}$alkenyl, and $C_{2-6}$alkynyl, wherein said alkyl, alkenyl and alkynyl groups are either unsubstituted or substituted with a group selected from OR$^c$, SR$^c$, NR$^b$R$^c$, C(=O)R$^c$, C(=O)CH$_2$OH, or phenyl, wherein said phenyl group can either be unsubstituted or substituted with 1–3 substituents independently selected from the group consisting of $C_{1-4}$alkyl, OH, O($C_{1-4}$alkyl), NH$_2$, NH($C_{1-4}$alkyl), NH($C_{1-4}$alkyl)$_2$, halo, CN, NO$_2$, CO$_2$H, CO$_2$($C_{1-4}$alkyl), C(O)H, and C(O)($C_{1-4}$alkyl);

R$^2$ is selected from the group consisting of hydrogen, hydroxy, iodo, O(C=O)R$^c$, C(=O)R$^c$, CO$_2$R$^c$, $C_{1-6}$alkyl, $C_{2-6}$alkenyl, and $C_{2-6}$alkynyl, wherein said alkyl, alkenyl and alkynyl groups are either unsubstituted or substituted with a group selected from OR$^c$, SR$^c$, NR$^b$R$^c$, C(=O)R$^c$, C(=O)CH$_2$OH, or phenyl, wherein said phenyl group can either be unsubstituted or substituted with 1–3 substituents independently selected from the group consisting of $C_{1-4}$alkyl, OH, O($C_{1-4}$alkyl), NH$_2$, NH($C_{1-4}$alkyl), NH($C_{1-4}$alkyl)$_2$, halo, CN, NO$_2$, CO$_2$H, CO$_2$($C_{1-4}$alkyl), C(O)H, and C(O)($C_{1-4}$alkyl);

or R$^1$ and R$^2$, when taken together with the carbon atom to which they are attached, form a carbonyl group;

or R$^1$ and R$^2$, when taken together, form a $C_{1-6}$ alkylidene group, wherein said alkylidene group is either unsubstituted or substituted with a group selected from the group consisting of hydroxy, O($C_{1-4}$alkyl), N($C_{1-4}$alkyl)$_2$, and phenyl, wherein said phenyl group can either be unsubstituted or substituted with 1–3 substituents independently selected from the group consisting of $C_{1-4}$alkyl, OH, O($C_{1-4}$alkyl), NH$_2$, NH($C_{1-4}$alkyl), NH($C_{1-4}$alkyl)$_2$, halo, CN, NO$_2$, CO$_2$H, CO$_2$($C_{1-4}$alkyl), C(O)H, and C(O)($C_{1-4}$alkyl);

R$^3$ is selected from the group consisting of fluoro, chloro, bromo, iodo, cyano, NR$^a$R$^c$, OR$^a$, C(=O)R$^a$, CO$_2$R$^c$, CONR$^a$R$^c$, SR$^a$, S(=O)R$^a$, SO$_2$R$^a$, $C_{1-10}$alkyl, $C_{2-10}$alkenyl, $C_{2-10}$alkynyl, $C_{3-7}$cycloalkyl, oxiranyl, azetidinyl, pyrrolidinyl, piperidinyl, piperazinyl, morpholoinyl, cycloalkylalkyl, aryl, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, purinyl and arylalkyl, wherein said alkyl, alkenyl, alkynyl, cycloalkyl, aryl, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl and purinyl groups are either unsubstituted or independently substituted with 1, 2 or 3 groups selected from fluoro, chloro, bromo, iodo, cyano, OR$^a$, NR$^a$R$^c$, O(C=O)R$^a$, O(C=O)NR$^a$R$^c$, NR$^a$(C=O)R$^c$, NR$^a$(C=O)OR$^c$, C(=O)R$^a$, CO$_2$R$^a$, CONR$^a$R$^c$, CSNR$^a$R$^c$, SR$^a$, S(O)R$^a$, SO$_2$R$^a$, SO$_2$NR$^a$R$^c$, YR$^d$, and ZYR$^d$;

R$^4$ is selected from the group consisting of hydrogen and fluoro;

R$^5$ is selected from the group consisting of hydrogen, fluoro, chloro, bromo, methyl, amino, OR$^b$, OR$^a$, O(C=O)R$^c$, O(C=O)OR$^c$, and NH(C=O)R$^c$;

R$^6$ is selected from the group consisting of hydrogen, fluoro, chloro, bromo, methyl, OR$^b$, OR$^a$, O(C=O)R$^c$, and O(C=O)OR$^c$;

R$^7$ is selected from the group consisting of hydrogen, OR$^b$, NR$^b$R$^c$, fluoro, chloro, bromo, iodo, cyano, nitro, $C_{1-6}$alkyl, $C_{2-6}$alkenyl, CF$_3$, and CHF$_2$;

R$^8$ and R$^9$ are each independently selected from the group consisting of hydrogen, $C_{1-6}$alkyl, $C_{2-6}$alkenyl, and $C_{2-6}$alkynyl, or R$^8$ and R$^9$, when taken together with the carbon atom to which they are attached, form a 3–5 membered cycloalkyl ring, or R$^8$ and R$^9$, when taken together with the carbon atom to which they are attached, form a carbonyl group;

R$^{10}$ is selected from the group consisting of hydrogen, $C_{1-10}$alkyl, $C_{2-10}$alkenyl, $C_{2-10}$alkynyl, $C_{3-6}$cycloalkyl, cycloalkylalkyl, aryl, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, purinyl and arylalkyl, wherein said alkyl, alkenyl, alkynyl, cycloalkyl, cycloalkylalkyl, aryl, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl, puriny and arylalkyl groups can be optionally substituted with a group selected from chloro, bromo, iodo, $OR^b$, $SR^b$, $C(=O)R^b$, or 1–5 fluoro, or $R^{10}$ and $R^1$, when taken together with the three intervening carbon atoms to which they are attached, form a 5–6 membered cycloalkyl or cycloalkenyl ring which can be optionally substituted with 1 or 2 groups selected from oxo, hydroxy, or $C_{1-6}$alkyl;

$R^{11}$ is selected from the group consisting of hydrogen and $C_{1-4}$alkyl;

$R^a$ is selected from the group consisting of hydrogen, $C_{1-10}$alkyl, and phenyl, wherein said alkyl group can be optionally substituted with a group selected from hydroxy, amino, $O(C_{1-4}alkyl)$, $NH(C_{1-4}alkyl)$, $N(C_{1-4}alkyl)_2$, phenyl, or 1–5 fluoro, and wherein said phenyl groups can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, $C(O)H$, and $C(O)(C_{1-4}alkyl)$;

$R^b$ is selected from the group consisting of hydrogen, $C_{1-01}$alkyl, benzyl and phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, $C(O)H$, and $C(O)(C_{1-4}alkyl)$;

$R^c$ is selected from the group consisting of hydrogen, $C_{1-4}$alkyl and phenyl, wherein said phenyl group can either be unsubstituted or substituted with 1–3 substituents independently selected from the group consisting of $C_{1-4}$alkyl, OH, $O(C_{1-4}alkyl)$, $NH_2$, $NH(C_{1-4}alkyl)$, $NH(C_{1-4}alkyl)_2$, halo, CN, $NO_2$, $CO_2H$, $CO_2(C_{1-4}alkyl)$, $C(O)H$, and $C(O)(C_{1-4}alkyl)$;

or $R^a$ and $R^c$, whether or not on the same atom, can be taken together with any attached and intervening atoms to form a 4–7 membered ring;

$R^d$ is selected from the group consisting of $NR^bR^c$, $OR^a$, $CO_2R^a$, $O(C=O)R^a$, CN, $NR^c(C=O)R^b$, $CONR^aR^c$, $SO_2NR^aR^c$, and a 4–7 membered N-heterocycloalkyl ring that can be optionally interrupted by O, S, $NR^c$, or C=O;

Y is selected from the group consisting of $CR^bR^c$, $C_{2-6}$ alkylene and $C_{2-6}$ alkenylene, wherein said alkylene and alkenylene linkers can be optionally interrupted by O, S, or $NR^c$;

Z is selected from the group consisting of O, S, $NR^c$, C=O, $O(C=O)$, $(C=O)O$, $NR^c(C=O)$ or $(C=O)NR^c$;

or a pharmaceutically acceptable salt or stereoisomer thereof.

2. A compound of the formula:

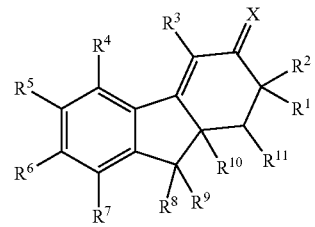

wherein X is selected from the group consisting of O and $N—OR^a$;

$R^1$ is selected from the group consisting of hydrogen and $C_{1-6}$alkyl, wherein said alkyl group is either unsubstituted or substituted with a group selected from $OR^c$ or $C(=O)R^c$;

$R^2$ is selected from the group consisting of hydrogen, hydroxy, iodo, and $C_{1-6}$alkyl, wherein said alkyl group is either unsubstituted or substituted with a group selected from $CR^c$ or $C(=O)R^c$;

$R^3$ is selected from the group consisting of chloro, bromo, iodo, cyano, $C_{1-10}$alkyl, $C_{2-10}$alkenyl, aryl, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl and purinyl wherein said alkyl, alkenyl, aryl, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl and purinyl groups are either unsubstituted or independently substituted with 1, 2 or 3 groups selected from fluoro, chloro, bromo, iodo, cyano, $OR^a$, $NR^aR^c$, $C(=O)R^a$, $CO_2R^c$, $NR^aC(=O)R^c$, $CONR^aR^c$, $CSNR^aR^c$, $SR^a$, $YR^d$, and $ZYR^d$;

$R^4$ is selected from the group consisting of hydrogen and fluoro;

$R^5$ and $R^6$ are each independently selected from the group consisting of hydrogen, fluoro, $O(C=O)R^c$ and $OR^a$;

$R^7$ is selected from the group consisting of hydrogen, $NR^bR^c$, chloro, bromo, nitro and $C_{1-6}$alkyl;

$R^8$ and $R^9$ are each independently selected from the group consisting of hydrogen and $C_{1-6}$alkyl;

or $R^8$ and $R^9$, when taken together with the carbon atom to which they are attached, form a carbonyl group;

$R^{10}$ is selected from the group consisting of hydrogen, $C_{1-10}$alkyl, $C_{2-10}$alkenyl, $C_{3-6}$cycloalkyl and cycloalkylalkyl, wherein said alkyl, alkenyl, cycloalkyl and cycloalkylalkyl groups can be optionally substituted with a group selected from $OR^b$, $SR^b$, $C(=O)R^b$, or 1–5 fluoro;

or $R^{10}$ and $R^1$, when taken together with the three intervening carbon atoms to which they are attached, form a 5–6 membered cycloalkyl ring which can be optionally substituted with $C_{1-6}$alkyl;

$R^{11}$ is selected from the group consisting of hydrogen and $C_{1-4}$alkyl;

$R^a$ is selected from the group consisting of hydrogen, $C_{1-10}$alkyl, and phenyl, wherein said alkyl group can be optionally substituted with a group selected from hydroxy, amino, $O(C_{1-4}alkyl)$, $NH(C_{1-4}alkyl)$, $N(C_{1-4}alkyl)_2$, phenyl, or 1–5 fluoro;

$R^b$ is selected from the group consisting of hydrogen, $C_{1-10}$alkyl, benzyl and phenyl;

$R^c$ is selected from the group consisting of hydrogen and $C_{1-10}$alkyl and phenyl;

or $R^a$ and $R^c$, whether or not on the same atom, can be taken together with any attached and intervening atoms to form a 4–7 membered ring;

$R^d$ is selected from the group consisting of $NR^bR^c$, $OR^a$, $CO_2R^a$, $O(C=O)R^a$, CN, $NR^c(C=O)R^b$, $CONR^aR^c$, $SO_2NR^aR^c$, and a 4–7 membered N-heterocycloalkyl ring that can be optionally interrupted by O, S, $NR^c$, or C=O;

Y is selected from the group consisting of $CR^bR^c$, $C_{2-6}$ alkylene and $C_{2-6}$ alkenylene, wherein said alkylene and alkenylene linkers can be optionally interrupted by O, S, or $NR^c$;

Z is selected from the group consisting of O, S, $NR^c$, C=O, O(C=O), (C=O)O, $NR^c$(C=O) or (C=O)$NR^c$;

or a pharmaceutically acceptable salt or stereoisomer thereof.

3. The compound according to claim 2, wherein X is selected from the group consisting of O, N—OH and N—OCH$_3$, or a pharmaceutically acceptable salt or stereoisomer thereof.

4. The compound according to claim 3, wherein $R^6$ is selected from the group consisting of $OR^a$ and $O(C=O)R^c$ or a pharmaceutically acceptable salt or stereoisomer thereof.

5. The compound according to claim 4, wherein $R^3$ is selected from the group consisting of, chloro, bromo, iodo, cyano, $C_{1-10}$alkyl, aryl, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl and purinyl wherein said alkyl, aryl, pyrrolyl, furyl, thienyl, imidazolyl, pyrazolyl, oxazolyl, isoxazolyl, thiazolyl, pyridyl, pyrimidinyl, pyrazinyl, benzimidazolyl, indolyl and purinyl groups are either unsubstituted or independently substituted with 1, 2 or 3 groups selected from fluoro, chloro, bromo, cyano, $NR^aR^c$, C(=O)$R^a$, $CO_2R^c$, $CONR^aR^c$, $SR^a$, $YR^d$, and $ZYR^d$, or a pharmaceutically acceptable salt or stereoisomer thereof.

6. The compound according to claim 1 selected from the group consisting of:

4-bromo-7-hydroxy-9a-methyl-1,2,9,9a-tetrahydro-3H-fluoren-3-one;

9a-butyl-7-hydroxy-4-methyl-1,2,9,9a-tetrahydro-3H-fluoren-3-one;

(3E)-9a-butyl-7-hydroxy-4-methyl-1,2,9,9a-tetrahydro-3H-fluoren-3-one oxime;

9a-[(1E)-1-butenyl]-7-hydroxy-4-methyl-1,2,9,9a-tetrahydro-3H-fluoren-3-one;

4-bromo-9a-butyl-7-hydroxy-1,2,9,9a-tetrahydro-3H-fluoren-3-one;

4-bromo-9a-butyl-3-methylene-2,3,9,9a-tetrahydro-1H-fluoren-7-ol;

9a-butyl-4-cyano-7-hydroxy-1,2,9,9a-tetrahydro-3H-fluoren-3-one;

4-benzyl-9a-butyl-7-hydroxy-1,2,9,9a-tetrahydro-3H-fluoren-3-one;

9a butyl-7-hydroxy-4-(2-thienyl)-1,2,9,9a-tetrahydro-3H-fluoren-3-ene;

9a-butyl-7-hydroxy-4-{4-[2-(1-piperidinyl)ethoxy]phenyl}-1,2,9,9a-tetrahydro-3H-fluoren-3-one hydrochloride;

9a-butyl-7-hydroxy-4-(4-hydroxyphenyl)-1,2,9,9a-tetrahydro-3H-fluoren-3-one;

(2E)-3-[4-(9a-butyl-7-hydroxy-3-oxo-2,3,9,9a-tetrahydro-1H-fluoren-4-yl)phenyl]-2-propenoic acid;

4-bromo-9a-butyl-7-hydroxy-8-methyl-1,2,9,9a-tetrahydro-3H-fluoren-3-one;

9a butyl-4,8-dimethyl-7-hydroxy-1,2,9,9a-tetrahydro-3H-fluoren-3-one;

9a-butyl-8-chloro-7-hydroxy-4-methyl-1,2,9,9a-tetrahydro-3H-fluoren-3-one;

(2SR,9aSR)-9a-butyl-2,4-dimethyl-7-hydroxy-1,2,9,9a-tetrahydro-3H-fluoren-3-one;

(2SR,9aRS)-9a-butyl-2,4-dimethyl-7-hydroxy-2-propyl-1,2,9,9a-tetrahydro-3H-fluoren-3-one;

9a-butyl-7-hydroxy-2,2,4-trimethyl-1,2,9,9a-tetrahydro-3H-fluoren-3-one;

(2SR,9aRS)-9a-butyl-7-hydroxy-2-iodo-4-methyl-1,2,9,9a-tetrahydro-3H-fluoren-3-one;

(2SR,9aRS)-9a-butyl-2,7-dihydroxy-4-methyl-1,2,9,9a-tetrahydro-3H-fluoren-3-one;

(2RS,9aSR)-9a-butyl-7-hydroxy-2-(2-hydroxyethyl)-4-methyl-1,2,9,9a-tetrahydro-3H-fluoren-3-one;

(2SR,9aSR)-2-allyl-9a-butyl-7-hydroxy-4-methyl-1,2,9,9a-tetrahydro-3H-fluoren-3-one;

(2RS,9aSR)-9a-butyl-7-hydroxy-2-(3-hydroxy-2-oxopropyl)-4-methyl-1,2,9,9a-tetrahydro-3H-fluoren-3-one;

(9SR,9aSR)-7-hydroxy-4-methyl-9-propyl-1,2,9,9a-tetrahydro-3H-fluoren-3-one;

9a-butyl-8-chloro-7-hydroxy-4-(trifluoromethyl)-1,2,9,9a-tetrahydro-3H-fluoren-3-one;

4-acetyl-9a-butyl-8-chloro-7-hydroxy-1,2,9,9a-tetrahydro-3H-fluoren-3-one;

9a-butyl-8-chloro-4-cyano-7-hydroxy-1,2,9,9a-tetrahydro-3H-fluoren-3-one;

9a-butyl-4-ethyl-6-fluoro-7-hydroxy-8-methyl-1,2,9,9a-tetrahydro-3H-fluoren-3-one;

9a-butyl-8-chloro-6-fluoro-7-hydroxy-4-methyl-1,2,9,9a-tetrahydro-3H-fluoren-3-one;

9a-butyl-8-chloro-4-ethyl-6-fluoro-7-hydroxy-1,2,9,9a-tetrahydro-3H-fluoren-3-one;

4-bromo-9a-butyl-8-chloro-6-fluoro-7-hydroxy-1,2,9,9a-tetrahydro-3H-fluoren-3-one;

9a-butyl-8-chloro-6-fluoro-7-hydroxy-4-(trifluoromethyl)-1,2,9,9a-tetrahydro-3H-fluoren-3-one;

2-hydroxy-5-methylgibba-1(10a),2,4,4b-tetraen-6-one;

4-bromo-9a-butyl-3-oxo-2,3,9,9a-1H-fluoren-7-yl pivalate;

7-hydroxy-4,9a-dimethyl-1,2,9,9a-tetrahydro-3H-fluoren-3-one;

9a-ethyl-7-hydroxy-4-methyl-1,2,9,9a-tetrahydro-3H-fluoren-3-one;

7-hydroxy-4-methyl-9a-propyl-1,2,9,9a-tetrahydro-3H-fluoren-3-one;

7-hydroxy-9a-isobutyl-4-methyl-1,2,9,9a-tetrahydro-3H-fluoren-3-one;

9a-butyl-4-ethyl-7-hydroxy-1,2,9,9a-tetrahydro-3H-fluoren-3-one;

9a-butyl-7-hydroxy-4-propyl-1,2,9,9a-tetrahydro-3H-fluoren-3-one;

4,9a-dibutyl-7-hydroxy-1,2,9,9a-tetrahydro-3H-fluoren-3-one;

9a-butyl-4-chloro-7-hydroxy-1,2,9,9a-tetrahydro-3H-fluoren-3-one;

9a-butyl-7-hydroxy-4-iodo-1,2,9,9a-tetrahydro-3H-fluoren-3-one;

9a-butyl-7-hydroxy-4-trifluoromethyl-1,2,9,9a-tetrahydro-3H-fluoren-3-one;

9a-butyl-7-hydroxy-4-phenyl-1,2,9,9a-tetrahydro-3H-fluoren-3-one;

9a-butyl-4-(2-furyl)-7-hydroxy-1,2,9,9a-tetrahydro-3H-fluoren-3-one;

7-hydroxy-9a-(3-iodopropyl)-4-methyl-1,2,9,9a-tetrahydro-3H-fluoren-3-one;

7-hydroxy-4-methyl-9a-(2-methyl-1-propenyl)-1,2,9,9a-tetrahydro-3H-fluoren-3-one;

9a-butyl-4-{4-[2-(dimethylamino)ethoxy]phenyl}-7-hydroxy-1,2,9,9a-tetrahydro-3H-fluoren-3-one hydrochloride;

9a-butyl-4-{4-[2-(diethylamino)ethoxy]-phenyl}-7-hydroxy-1,2,9,9a-tetrahydro-3H-fluoren-3-one hydrochloride;

9a-butyl-7-hydroxy-4-{4-[2-(1-pyrrolidinyl)ethoxy]phenyl}-1,2,9,9a-tetrahydro-3H-fluoren-3-one hydrochloride;

9a-butyl-7-hydroxy-4-{4-[2-(4-morpholinyl)ethoxy]phenyl}-1,2,9,9a-tetrahydro-3 H-fluoren-3-one hydrochloride;

9a-butyl-4-{4-[3-(dimethylamino)propoxy]-phenyl}-7-hydroxy-1,2,9,9a-tetrahydro-3H-fluoren-3-one hydrochloride;

9a-butyl-7-hydroxy-4-{4-[3-(1-piperidinyl)propoxy]phenyl}-1,2,9,9a-tetrahydro-3H-fluoren-3-one hydrochloride;

(3E)-9a-butyl-7-hydroxy-4-methyl-1,2,9,9a-tetrahydro-3H-fluoren-3-one O-methyloxime;

(2SR,9aSR)-9a-butyl-2-ethyl-7-hydroxy-4-methyl-1,2,9,9a-tetrahydro-3H-fluoren-3-one;

(2SR,9aSR)-9a-butyl-7-hydroxy-4-methyl-2-propyl-1,2,9,9a-tetrahydro-3H-fluoren-3-one;

(2SR,9aSR)-4,9a-dibutyl-7-hydroxy-2-propyl-1,2,9,9a-tetrahydro-3H-fluoren-3-one;

(2SR,9aSR)-4-bromo-9a-butyl-7-hydroxy-2-propyl-1,2,9,9a-tetrahydro-3H-fluoren-3-one;

(2SR,9aSR)-2,9a-dibutyl-7-hydroxy-4-methyl-1,2,9,9a-tetrahydro-3H-fluoren-3-one;

(2SR,9aSR)-9a-butyl-7-hydroxy-2,4-dimethyl-2-propyl-1,2,9,9a-tetrahydro-3H-fluoren-3-one;

9a-butyl-7-hydroxy-4-methyl-2,2-dipropyl-1,2,9,9a-tetrahydro-3H-fluoren-3-one;

(2SR,9aSR)-9a-butyl-2,7-dihydroxy-4-methyl-2-propyl-1,2,9,9a-tetrahydro-3H-fluoren-3-one;

4-bromo-9a-butyl-2,2-diethyl-7-hydroxy-1,2,9,9a-tetrahydro-3H-fluoren-3-one;

(2SR,9aSR)-7-hydroxy-2,4,9a-trimethyl-1,2,9,9a-tetrahydro-3H-fluoren-3-one;

(2SR,9aSR)-7-hydroxy-4,9a-dimethyl-2-propyl-1,2,9,9a-tetrahydro-3H-fluoren-3-one;

(2SR,9aSR)-9a-butyl-8-chloro-2-ethyl-7-hydroxy-4-methyl-1,2,9,9a-tetrahydro-3H-fluoren-3-one;

8-chloro-9a-ethyl-7-hydroxy-4-methyl-1,2,9,9a-tetrahydro-3H-fluoren-3-one;

8-bromo-9a-ethyl-7-hydroxy-4-methyl-1,2,9,9a-tetrahydro-3H-fluoren-3-one;

9a-ethyl-7-hydroxy-4,8-dimethyl-1,2,9,9a-tetrahydro-3H-fluoren-3-one;

8-chloro-7-hydroxy-4-methyl-9a-propyl-1,2,9,9a-tetrahydro-3H-fluoren-3-one;

8-bromo-7-hydroxy-4-methyl-9a-propyl-1,2,9,9a-tetrahydro-3H-fluoren-3-one;

7-hydroxy-4,8-dimethyl-9a-propyl-1,2,9,9a-tetrahydro-3H-fluoren-3-one;

8-chloro-7-hydroxy-4-methyl-9a-[(1E)-1-propenyl]-1,2,9,9a-tetrahydro-3H-fluoren-3-one;

8-bromo-9a-butyl-7-hydroxy-4-methyl-1,2,9,9a-tetrahydro-3H-fluoren-3-one;

9a-butyl-7-hydroxy-4,8-dimethyl-1,2,9,9a-tetrahydro-3H-fluoren-3-one;

9a-butyl-7-hydroxy-4-methyl-8-nitro-1,2,9,9a-tetrahydro-3H-fluoren-3-one;

8-amino-9a-butyl-7-hydroxy-4-methyl-1,2,9,9a-tetrahydro-3H-fluoren-3-one;

9a-butyl-7-hydroxy-4-(4-hydroxyphenyl)-8-methyl-1,2,9,9a-tetrahydro-3H-fluoren-3-one;

9a-butyl-7-hydroxy-8-methyl-4-{4-[2-piperidinyl)-ethoxy]phenyl}-1,2,9,9a-tetrahydro-3H-fluoren-3-one;

4-bromo-7-hydroxy-9a-propyl-1H-fluorene-3,9(2H,9aH)-dione;

4,8-dibromo-7-hydroxy-9a-propyl-1H-fluorene-3,9(2H,9aH)-dione;

4-bromo-9a-butyl-7-hydroxy-6-methyl-1,2,9,9a-tetrahydro-3H-fluoren-3-one;

9a-butyl-8-chloro-4-methyl-3-oxo-2,3,9,9a-tetrahydro-1H-fluoren-7-yl pivalate;

9a-butyl-6,8-difluoro-7-hydroxy-4-methyl-1,2,9,9a-tetrahydro-3H-fluoren-3-one;

9a-butyl-4-ethyl-6,8-difluoro-7-hydroxy-1,2,9,9a-tetrahydro-3H-fluoren-3-one;

4-bromo-9a-butyl-6,8-difluoro-7-hydroxy-1,2,9,9a-tetrahydro-3H-fluoren-3-one;

8-bromo-9a-butyl-4-chloro-8-difluoro-7-hydroxy-1,2,9,9a-tetrahydro-3H-fluoren-3-one;

9a-butyl-4,8-dibromo-6-fluoro-7-hydroxy-1,2,9,9a-tetrahydro-3H-fluoren-3-one;

9a-ethyl-6-fluoro-7-hydroxy-4-methyl-1,2,9,9a-tetrahydro-3H-fluoren-3-one;

9a-ethyl-6,8-difluoro-7-hydroxy-4-methyl-1,2,9,9a-tetrahydro-3H-fluoren-3-one;

8-chloro-9a-ethyl-6-fluoro-7-hydroxy-4-methyl-1,2,9,9a-tetrahydro-3H-fluoren-3-one;

8-bromo-9a-ethyl-6-fluoro-7-hydroxy-4-methyl-1,2,9,9a-tetrahydro-3H-fluoren-3-one;

9a-ethyl-6-fluoro-7-hydroxy-4,8-dimethyl-1,2,9,9a-tetrahydro-3H-fluoren-3-one;

4,9a-diethyl-6,8-difluoro-7-hydroxy-1,2,9,9a-tetrahydro-3H-fluoren-3-one;

4-bromo-8-chloro-9a-ethyl-6-fluoro-7-hydroxy-1,2,9,9a-tetrahydro-3H-fluoren-3-one;

4-bromo-8-chloro-9a-(cyclopentylmethyl)-6-fluoro-7-hydroxy-1,2,9,9a-tetrahydro-3H-fluoren-3-one;

9a-ethyl-5-fluoro-7-hydroxy-4-methyl-1,2,9,9a-tetrahydro-3H-fluoren-3-one;

8-bromo-9a-ethyl-5-fluoro-7-hydroxy-4-methyl-1,2,9,9a-tetrahydro-3H-fluoren-3-one;

9a-ethyl-6,7-dihydroxy-4-methyl-1,2,9,9a-tetrahydro-3H-fluoren-3-one;

8-bromo-9a-ethyl-6,7-dihydroxy-4-methyl-1,2,9,9a-tetrahydro-3H-fluoren-3-one;

9a-ethyl-6-hydroxy-4-methyl-1,2,9,9a-tetrahydro-3H-fluoren-3-one;

9a-ethyl-6-hydroxy-4-vinyl-1,2,9,9a-tetrahydro-3H-fluoren-3-one;

4-allyl-9a-ethyl-6-hydroxy-1,2,9,9a-tetrahydro-3H-fluoren-3-one;

7-amino-4-bromo-9a-butyl-1,2,9,9a-tetrahydro-3H-fluoren-3-one;

7-amino-4,8-dibromo-9a-ethyl-1,2,9,9a-tetrahydro-3H-fluoren-3-one;

or a pharmaceutically acceptable salt or stereoisomer thereof.

7. A pharmaceutical composition comprising a compound according to claim 1 and a pharmaceutically acceptable carrier.

8. A pharmaceutical composition made by combining a compound according to claim 1 and a pharmaceutically acceptable carrier.

9. A process for making a pharmaceutical composition comprising combining a compound according to claim 1 and a pharmaceutically acceptable carrier.

10. A method of treating hot flashes in a mammal in need thereof by administering to the mammal a therapeutically effective amount of a compound according to claim 1.

11. The compound of claim 6 which is 9a-ethyl-7-hydroxy-4-methyl-1,2,9,9a-tetrahydro-3H-fluoren-3-one or a pharmaceutically acceptable salt or stereoisomer thereof.

12. The compound of claim 6 which is 9a-butyl-7-hydroxy-4-methyl-1,2,9,9a-tetrahydro-3H-fluoren-3-one or a pharmaceutically acceptable salt or stereoisomer thereof.

13. The compound of claim 6 which is 4-bromo-9a-butyl-7-hydroxy-1,2,9,9a-tetrahydro-3H-fluoren-3-one or a pharmaceutically acceptable salt or stereoisomer thereof.

14. The compound of claim 6 which is 9a-butyl-8-chloro-7-hydroxy-4-methyl-1,2,9,9a-tetrahydro-3H-fluoren-3-one or a pharmaceutically acceptable salt or stereoisomer thereof.

15. The compound of claim 6 which is 9a-butyl-8-chloro-4-cyano-7-hydroxy-1,2,9,9a-tetrahydro-3H-fluoren-3-one or a pharmaceutically acceptable salt or stereoisomer thereof.

16. The compound of claim 6 which is 9a-ethyl-6-fluoro-7-hydroxy-4,8-dimethyl-1,2,9,9a-tetrahydro-3H-fluoren-3-one or a pharmaceutically acceptable salt or stereoisomer thereof.

17. The compound of claim 6 which is 4-bromo-8-chloro-9a-ethyl-6-fluoro-7-hydroxy-1,2,9,9a-tetrahydro-3H-fluoren-3-one or a pharmaceutically acceptable salt or stereoisomer thereof.

18. The compound of claim 6 which is 4-bromo-9a-butyl-8-chloro-6-fluoro-7-hydroxy-1,2,9,9a-tetrahydro-3H-fluoren-3-one or a pharmaceutically acceptable salt or stereoisomer thereof.

19. The compound of claim 6 which is 9a-butyl-8-chloro-6-fluoro-7-hydroxy-4-(trifluoromethyl)-1,2,9,9a-tetrahydro-3H-fluoren-3-one or a pharmaceutically acceptable salt or stereoisomer thereof.

20. The compound of claim 6 which is 4-bromo-8-chloro-9a-(cyclopentylmethyl)-6-fluoro-7-hydroxy-1,2,9,9a-tetrahydro-3H-fluoren-3-one or a pharmaceutically acceptable salt or stereoisomer thereof.

21. A pharmaceutical composition comprising a compound of claim 1 and an organic bisphosphonate or a cathepsin K inhibitor, or a pharmaceutically acceptable salt or mixture thereof.

22. The composition of claim 21 wherein the bisphosphonate is selected from alendronate, clodronate, etidronate, ibandronate, incadronate, minodronate, neridronate, risedronate, piridronate, pamidronate, tiludronate, zoledronate, pharmaceutically acceptable salts, esters or mixtures thereof.

23. The composition of claim 22 wherein the bisphosphonate is alendronate.

24. A method of treating hot flashes comprising administering to a mammal in need thereof a compound of claim 1 and an organic bisphosphonate or a cathepsin K inhibitor, or a pharmaceutically acceptable salt or mixture thereof.

25. The method of claim 24 wherein the bisphosphonate is selected from alendronate, clodronate, etidronate, ibandronate, incadronate, minodronate, neridronate, risedronate, piridronate, pamidronate, tiludronate, zoledronate, pharmaceutically acceptable salts, esters or mixtures thereof.

26. The method of claim 25 wherein the bisphosphonate is alendronate.

27. 4-bromo-9a-butyl-8-chloro-6-fluoro-7-hydroxy-1,2,9,9a-tetrahydro-3H-fluoren-3-one or a pharmaceutically acceptable salt or stereoisomer thereof.

* * * * *